:::
United States Patent [19]

Hale et al.

[11] Patent Number: 5,607,691
[45] Date of Patent: Mar. 4, 1997

[54] COMPOSITIONS AND METHODS FOR ENHANCED DRUG DELIVERY

[75] Inventors: Ron L. Hale, Woodside; Amy Lu, Los Altos; Dennis Solas, San Francisco; Harold E. Selick, Belmont; Kevin R. Oldenburg, Fremont; Alejandro C. Zaffaroni, Atherton, all of Calif.

[73] Assignee: Affymax Technologies N.V., Middlesex, England

[21] Appl. No.: 449,188

[22] Filed: May 24, 1995

Related U.S. Application Data

[63] Continuation of Ser. No. 164,293, Dec. 9, 1993, abandoned, which is a continuation-in-part of Ser. No. 77,296, Jun. 14, 1993, abandoned, which is a continuation-in-part of Ser. No. 898,219, Jun. 12, 1992, abandoned, and a continuation-in-part of Ser. No. 9,463, Jan. 27, 1993, abandoned.

[51] Int. Cl.$^6$ ............................ A61K 9/70; A61K 31/00
[52] U.S. Cl. .................. 424/449; 604/20; 514/1; 514/2; 514/26; 514/183; 514/169; 514/553; 514/556
[58] Field of Search ...................... 424/22, 448, 449, 424/485, 486; 604/20; 514/1, 2, 26, 169, 183, 553, 556

[56] References Cited

U.S. PATENT DOCUMENTS

| | | | |
|---|---|---|---|
| 3,472,931 | 10/1969 | Stoughton | 424/180 |
| 4,006,218 | 2/1977 | Sipos | 424/54 |
| 4,144,328 | 3/1979 | Vainshtein et al. | 424/180 |
| 4,195,172 | 3/1980 | Falkowski et al. | 536/17 R |
| 4,294,958 | 10/1981 | Falkowski et al. | 536/17 |
| 4,427,660 | 1/1984 | Schiffman et al. | 424/177 |
| 4,454,065 | 6/1984 | Gilvarg et al. | 260/112 R |
| 4,588,580 | 5/1986 | Gale et al. | 424/21 |
| 4,645,502 | 2/1987 | Gale et al. | 604/89 |
| 4,727,151 | 2/1988 | Bodor | 546/174 |
| 4,788,062 | 11/1988 | Gale et al. | 424/449 |
| 4,816,258 | 3/1989 | Nedberg et al. | 424/448 |
| 4,846,826 | 7/1989 | Shaw et al. | 604/890.1 |
| 4,900,555 | 2/1990 | Cheng et al. | 424/449 |
| 4,904,475 | 2/1990 | Gale et al. | 424/449 |
| 4,908,027 | 3/1990 | Enscore et al. | 604/890.1 |
| 4,927,408 | 5/1990 | Haak et al. | 604/20 |
| 4,963,367 | 10/1990 | Ecanow | 424/485 |
| 4,978,337 | 12/1990 | Theeuwes | 604/85 |
| 5,011,686 | 4/1991 | Pang | 424/94.1 |
| 5,013,653 | 5/1991 | Huston et al. | 435/69.7 |
| 5,028,435 | 7/1991 | Katz et al. | 424/484 |
| 5,053,227 | 10/1991 | Chiang et al. | 424/484 |
| 5,149,539 | 9/1992 | Ledger et al. | 424/449 |
| 5,219,564 | 6/1993 | Zalipsky et al. | 424/78.17 |
| 5,223,261 | 6/1993 | Nelson et al. | 424/443 |
| 5,246,967 | 9/1993 | Zezza | 514/547 |
| 5,270,472 | 12/1993 | Taglialatela et al. | 560/251 |

FOREIGN PATENT DOCUMENTS

| | | | |
|---|---|---|---|
| 0031722 | 7/1981 | European Pat. Off. | C07H 17/08 |
| 0331391 | 9/1989 | European Pat. Off. | A61K 45/00 |
| 0351173 | 1/1990 | European Pat. Off. | C07H 17/08 |
| 0385610 | 9/1990 | European Pat. Off. | A61K 39/295 |
| 0559625 | 9/1993 | European Pat. Off. | C07C 229/22 |
| 8801615 | 3/1988 | WIPO | C07C 103/30 |
| 9008128 | 7/1990 | WIPO | |
| 9106556 | 5/1991 | WIPO | C07H 21/00 |
| 9113631 | 9/1991 | WIPO | A61K 39/00 |
| 9114696 | 10/1991 | WIPO | C07H 17/00 |
| 9115259 | 10/1991 | WIPO | A61N 1/30 |
| 92/08459 | 5/1992 | WIPO | |
| 9217180 | 10/1992 | WIPO | A61K 31/505 |
| 92/22530 | 12/1992 | WIPO | |
| 9307883 | 4/1993 | WIPO | A61K 31/70 |
| 9317713 | 9/1993 | WIPO | A61K 47/48 |

OTHER PUBLICATIONS

Bodor, et al. Int. J. Pharm, 35(1–2) 47–59 1987 Improved Delivery Through Biological Membranes.
Pratt et al., 1990, Principles of drug action: The basis of pharmacology 203–227 Principles of drug action: The basis of pharmacology.
Russell–Jones et al., 1988, Proceed Intern. Symp. Control. Rel. Bioact. Mater. 85: 142–143 Vitamin B12: A novel carrier for orally presented antigens.
Bodde et al., 1989, Biochemical Society 17 (3): 197–199 Transdermal peptide delivery.
Sanderson et al., 1989, J. of Pharm. Sci. 78 (5): 361–364. Iontophoretic delivery of nonpeptide drugs: Formulation optimization for maximum skin permeability.
Harris, Physical Medicine Library vol. IV, Therapeutic electricity and ultraviolet radiation, pp. 146–149.
Foder et al., 1991, Science 251: 767–773 Light–Directed, spatially addressable parallel chemical synthesis.
Bioworld 29 Jan 92, 3 (20): p. 1 FDA approves Elan's nicotine patch.
Chien et al., 1989, J. Pharm. Sci. 78 (5): 376–383 Direct current iontophoretic transdermal delivery of peptide and protein drugs.
Srinivasan et al., 1989, J. of Pharm. Sci. 78(5): 370–375 Transdermal iontophoretic drug delivery : Mechanistic analysis and application to polypeptide delivery.
West, Textbook of Biochemistry, Ch. 6: 169–170 Lipids.
Chien et al., 5 May 1989, J. Pharm. Sci. 78 (5): 353–354 Iontophoretic (transdermal) delivery of drugs: Overview of historical development.
Fix et al., 1986, The American Physiological Society: G332–G340 Acylcarnitines: drug absorption–enhancing agents in the gastrointestinal tract.
Banga et al., 1988, J. Controlled Release 7: 1–24 Iontophoretic delivery of drugs: Fundamentals, developments and biomedical applications.
Bernstein, 92, Bioworld 3 (105): p.1 Patch developers extinguish suits.

(List continued on next page.)

*Primary Examiner*—Neil S. Levy
*Attorney, Agent, or Firm*—Lauren L. Stevens

[57] ABSTRACT

The present invention relates to methods of delivering pharmaceutical agents across membranes, including the skin layer or mucosal membranes of a patient. A pharmaceutical agent is covalently bonded to a chemical modifier, via a physiologically cleavable bond, such that the membrane transport and delivery of the agent is enhanced.

5 Claims, No Drawings

OTHER PUBLICATIONS

Behl et al., 1989, J. of Pharm. Sci. 78 (5): 355–360 Iontophoretic drug delivery: Effects of physicochemical factors on the skin uptake of nonpeptide drugs.

Benet et al., Pharmacokinetics: The dynamics of drug absorption, Distributuion, and elimination. Ch. 1: 3–10 Pharmacokinetics: The dynamics of drug absorption, distribution, and elimination.

Phipps et al., 1989, J. of Pharm. Sci. 78 (5): 365–369 Iontophoretic delivery of model inorganic and drug ions.

Ames et al., Feb. 1973, Proc. Natl. Acad. Sci. USA 70(2): 456–458 Illicit Transport: The Oligopeptide Permease.

Bodor et al., 18 Sep. 1992, Science 257: 1698–1700 A strategy for delivering peptides into the central nervous system by sequential metabolism.

Jacobson et al., 1986, Mol. Pharmacol. 29: 126–133 A fuctionalized congener approach to adenosine receptor antogonists: Amino Acid conjugates of 1,3–Dipropylxanthine.

Jacobson et al., 1987, J. Med. Chem. 30: 1529–1532 Binary Drugs: Conjugates of purines and a peptide that binds to both adenosine and substance P receptors.

COMPOSITIONS AND METHODS FOR ENHANCED DRUG DELIVERY

This is a Continuation of application Ser. No. 08/164,293, filed Dec. 9, 1993 now abandoned, which is a continuation-in-part of application Ser. No. 08/077,296, filed Jun. 14, 1993 which is a continuation-in-part of applications Ser. Nos. 07/898,219, filed Jun. 12, 1992 now abandoned, and 08/009,463, filed Jan. 27, 1993 now abandoned. Each of the above identified applications are incorporated herein by reference for all purposes.

BACKGROUND OF THE INVENTION

The present invention relates generally to methods for improving the transport and delivery of pharmaceutical agents across membranes. More particularly, the invention relates to methods for enhancing the transport and delivery of pharmaceutical agents through the addition of one or more chemical modifiers to the pharmaceutical agent.

The therapeutic efficacy of pharmaceutical or therapeutic agents relies on the delivery of adequate doses of a pharmaceutical agent to the site of action. Many modes of delivery have been developed, including, for example, enteral (oral), parenteral (intramuscular, intravenous, subcutaneous), and topical administration. In most instances the administration system is chosen for reliable dosage delivery and convenience.

Typically, parenteral administration is the most reliable means of delivering a pharmaceutical to a patient. See, Goodman et al., *Goodman and Gilman's Pharmacological Basis of Therapeutics*, Pergamon Press, Elmsford, N.Y. (1990) and Pratt et al. *Principles of Drug Action: The Basis of Pharmacology*, Churchill Livingstone, New York, N.Y. (1990). Each parenteral mechanism insures that a prescribed dosage of the pharmaceutical agent is inserted into the fluid compartment of the body where it can be transported. The disadvantage of these modes of delivery is that they require an invasive procedure. The invasive nature of administration is inconvenient, painful and subject to infectious contamination.

Enteral and topical administration are more convenient, generally non-painful, and do not predispose to infection; however, both are limited. The gastrointestinal and dermal surfaces present formidable barriers to transport and therefore, some pharmaceutical agents are not absorbed across these surfaces. Another drawback to patient directed modes of administration (enteral, topical and subcutaneous) is compliance. Pharmaceutical agents that have a short half-life require multiple daily doses. As the number of doses increases, patient compliance and therapeutic efficacy decrease. Simplified and/or less frequent administration schedules can aid in optimizing patient compliance. Wilson et al. (1991) *Harrison's Principles of Internal Medicine*, 12th Ed., McGraw-Hill, Inc., New York, N.Y.

The skin is an efficient barrier to the penetration of water soluble substances, and the rate of transdermal pharmaceutical agent absorption is primarily determined by the agent's lipid solubility, water solubility, and polarity. Highly polar or water soluble pharmaceutical agents are effectively blocked by the skin. Even very lipophilic pharmaceutical agents penetrate the dermis very slowly compared with the rate of penetration across cell membranes. See Pratt et al. supra.

Efforts to develop more effective and convenient modes of pharmaceutical administration have led to the development of transdermal delivery systems. Many current transdermal pharmaceutical agent delivery systems rely upon pharmaceutical agents that are absorbed when admixed with inert carriers. See Cooper et al. (1987) "Penetration Enhancers", in *Transdermal Delivery of Drugs*, Vol. II, Kyodonieus et al., Eds., CRC Press, Boca Raton, Fla. Few pharmaceutical agents fit this profile and those which do are not always predictably absorbed. Various forms of chemical enhancers, such as those enhancing lipophilicity, have been developed to improve transdermal transport when physically mixed with certain therapeutic agents and provide more predictable absorption. See for example, U.S. Pat. Nos. 4,645,502; 4,788,062; 4,816,258; 4,900,555; 3,472,931; 4,006,218; and 5,053,227. Carriers have also been coupled to pharmaceutical agents to enhance intracellular transport. See Ames et al. (1973) *Proc. Natl. Acad. Sci. USA*, 70:456–458 and (1988) *Proc. Int. Symp. Cont. Rel. Bioact. Mater.*, 15:142.

Electric gradients also have been used to enhance transdermal pharmaceutical agent delivery. See Chien et al. (1989) *Journal of Pharmaceutical Sciences*, 78(5):353–354 and Banga et al. (1988) *J. Controlled Release*, 7:1–14. This technique, known as iontophoresis, uses an electric field to enhance the rate of delivery of ionized pharmaceutical agents through the skin. Typically, devices are used which hold a pharmaceutical agent in a reservoir near the skin, generate an electric field surrounding the pharmaceutical agent-dermal interface, and drive the agent through the skin.

For iontophoretic delivery, the drug molecules must be in an ionized state with either a positive or negative charge. Nonionic drugs may also be delivered iontophoretically provided that a charge can be induced on them, for example, by adsorption of drug onto an ionic carrier or entrapment in an ionic micelle. See Banga (1988) *J. Controlled Release*, 7:1–24.

The rate of drug delivery in iontophoresis is directly proportional to the system current; the higher the current, the greater the driving force and pharmaceutical agent delivery. Ionic strength also affects the iontophoretic drug delivery rate. See Banga supra. Ionic strength is related to the concentration of various ions present in the solution of the pharmaceutical agent in the reservoir. Other factors that may affect the delivery rate include pH, concentration, extraneous ions, conductivity, and electronic factors.

SUMMARY OF THE INVENTION

There exists a significant need for nontoxic chemical modifiers which can reversibly bind to pharmaceutical agents and improve the delivery or transport through membranes, or other biological or physical properties, of the pharmaceutical agent. These chemical modifiers can also have beneficial therapeutic effects apart from their carrier function or can be degraded. The present invention fulfills these needs.

This invention provides for methods of modifying a pharmaceutical agent comprising covalently bonding a charged chemical modifier, via a physiologically cleavable bond, to the pharmaceutical agent, such that the delivery and/or transport of the agent through membranes, or other biological or physical property of the agent, are enhanced. The chemical modifier covalently bonded to the pharmaceutical agent forms a pharmaceutical agent-chemical modifier complex which is administered to a patient, wherein the chemical modifier is cleaved from the complex by a physiological process once the complex has been delivered, and the pharmaceutical agent is released within the patient in an active form. One or more chemical modifiers is covalently bonded to the agent and the modifiers can be positively or negatively charged. In some embodiments, a functionality modifier will also be covalently bonded to the pharmaceutical agent-chemical modifier complex, optionally via a spacer group.

This invention provides for chemical modifiers which are bound to pharmaceutical agents to enhance the transport, delivery, or other biological or physical properties of the pharmaceutical agent. Representative pharmaceutical agents include digitalis drugs; steroidal compounds; nonsteroidal anti-inflammatories; protein and peptide drugs; nucleotide-based drugs; and nitrogen heterocycles, including yohimbine, morphine, methotrexate, lorazepam, 6-mercaptopurine, and 5-fluorouracil. Representative modifiers include taurine, betaine, carnitine, oligomeric carnitine, choline, lysine, polylysine, E-methylated lysine, oligomeric methylated lysine, other methylated amino acids, trigonelline, stachydrine, betonicine, histones, protamines, histones, nucleotide-based chemical modifiers, cytochrome c, squalamine, chonemorphine, conessine, and other bi- or multi-functional quaternary ammonium salts.

This invention provides for methods for the delivery of a pharmaceutical agent, comprising the steps of:

a) binding one or more chemical modifiers to the pharmaceutical agent through physiologically cleavable covalent bonds thereby forming a pharmaceutical agent-chemical modifier complex;

b) administering to a therapeutically effective amount of the complex.

In a preferred embodiment, the pharmaceutical agent-chemical modifier complex is administered to the skin or mucousal membrane by applying an electric field to the interface of the complex and the skin or membrane, such that the electric field transdermally delivers the complex. The complex has an enhanced delivery or transport rate through membranes over the pharmaceutical agent alone.

Other methods for the delivery of a pharmaceutical agent are provided comprising the steps of:

a) administering to a patient's skin or mucosal membrane with a therapeutically effective amount of a pharmaceutical agent-chemical modifier complex, wherein the complex is formed by the binding of one or more chemical modifiers to a pharmaceutical agent through physiologically clearable covalent bonds; and b) delivering the complex through the skin or membrane.

In a preferred embodiment, an iontophoretic drug delivery device is utilized to delivery the complex through skin via application of an electric field.

Compositions are provided comprising a pharmaceutical agent covalently bonded to one or more charged chemical modifiers through physiologically cleavable bonds to form a pharmaceutical agent-chemical modifier complex, wherein the modifiers enhance the delivery and/or transport of the pharmaceutical agent through membranes, or other biological or physical property of the agent. This invention also provides a pharmaceutical formulation which comprises a pharmaceutically effective amount of a pharmaceutical agent-chemical modifier composition and acceptable physiological carriers or excipients thereof. The invention also provides pharmaceutical agent compositions containing a pharmaceutical agent in a complex with one or more chemical modifiers such as taurine, betaine, carnitine, oligomeric carnitine, choline, lysine, polylysine, E-methylated lysine, oligomeric methylated lysine, other methylated amino acids, histories, protamines, nucleotide-based chemical modifiers, cytochrome c, squalamine, chonemorphine, conessine, and quaternary ammonium salts which are useful in enhancing pharmaceutical agent transport and delivery.

DETAILED DESCRIPTION OF THE INVENTION

CONTENTS

I. Terminology

II. The Pharmaceutical Agent-Chemical Modifier Complex

A. The Pharmaceutical Agent
    i. General
    ii. Digitalis Drugs
    iii. Steroidal Compounds
    iv. Nonsteroidal Anti-inflammatories
    v. Protein and Peptide Drugs
    vi. Nucleotide-based Drugs
    vii. Heterocyclic Drugs
  B. The Chemical Modifier
    i. General
    ii. Positively Charged Chemical Modifiers
    iii. Examples of Chemical Modifiers
    iv. Negatively Charged Chemical Modifiers
    v. Nucleotide-based Chemical Modifiers
    vi. Screening Procedures
  C. Methods of Activation
  D. Methods of Linking
  E. Spacer Groups
  F. Optional Functionality Modifiers
  G. Bi- and Multi-functional Modifiers, Pharmaceutical Agents, and Spacer Groups III. Preparation of the Pharmaceutical Agent-Chemical Modifier Complex A. General
  B. Multi-Adducts
  C. Recombinant Approaches IV. Compositions of the Pharmaceutical Agent-Modifier Complex V. In Vitro Testing of Pharmaceutical Agent-Chemical Modifier Complexes VI. In Vivo Delivery of Pharmaceutical Agent-Chemical Modifier Complexes A. General
  B. Transdermal Delivery
    i. General
    ii. Passive Transdermal Drug Delivery
    iii. Iontophoresis
    iv. Topical Treatments
  C. Transmucosal Delivery
    i. Buccal Administration
    ii. Nasal Administration VII. Cleavage of the Complexes

I. TERMINOLOGY

Unless otherwise stated, the following terms used in the specification and claims have the meanings given below:

Pharmaceutical agent or drug" refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical agent" and "drug" encompass both the inactive drug and the active metabolite.

"Transport" and "delivery" refers to the passage of a substance across or through the skin (i.e., transdermal), including the epidermis and dermis, or across a mucosal membrane (i.e., gastrointestinal, sublingual, buccal, nasal, pulmonary, vaginal, corneal, and ocular membranes), where the substance can contact, and be absorbed into, the capillaries. In certain instances, the delivery and/or transport of the substance across other membranes will be effected.

"Buccal delivery" refers to any system or device for the oral administration of a drug to a patient that is held in the mouth and is used to deliver a drug through the buccal mucosa and into the patient's body. This term includes, but is not limited to, lozenges, capsules, and tablets.

"Enhanced delivery" refers both to the facilitation of the delivery of a pharmaceutical agent and an absolute increase in the molar volume of the pharmaceutical agent transported per unit time through a constant surface area utilizing an equimolar pool of transported material as compared to unenhanced delivery.

"Iontophoresis" or "iontophoretic" refers to the introduction of an ionizable chemical through skin or mucosal membranes by the application of an electric field to the interface between the ionizable chemical compound and the skin or mucosal membrane.

"Permeability" refers to the ability of an agent or substance to penetrate, pervade, or diffuse through a barrier, membrane, or a skin layer, for example, between the cells of the stratum corneum and/or through the shunt pathways, including the sweat ducts and the hair follicles and/or intracellularly.

"Chemical modifier" refers to a charged molecule capable of covalently bonding to a pharmaceutical agent, another modifier, and/or a spacer group. The term "chemical modifier" is meant to include both the charged molecule and its counterions, if any. The covalent bond between the modifier and agent is preferably reversible and can be cleaved in vivo by biological or physiological processes which release the agent in an active form.

"Spacer group" refers to a molecule capable of covalently bonding simultaneously to both a pharmaceutical agent and a chemical modifier, optionally via another spacer group(s), and which does not necessarily carry a charge.

"Functionality modifier" refers to a molecule capable of covalently bonding to a pharmaceutical agent, a chemical modifier, or a spacer group, optionally via a spacer group(s), which does not necessarily carry a charge, and which serves to affect or modify a chemical, physical, or biological property of a pharmaceutical agent-chemical modifier complex, for example, providing a means for detection, for modifying the excretion half-life, for targeting, for increasing avidity, for decreasing aggregation, for decreasing the inflammation and/or irritation accompanying the delivery of the pharmaceutical agent across membranes, and for facilitating receptor crosslinking. According to a preferred embodiment, the functionality modifier will carry a charge and thus, is also a chemical modifier.

"Pharmaceutical agent-modifier", "pharmaceutical agent-modifier complex", "pharmaceutical agent-chemical modifier", or "pharmaceutical agent-chemical modifier complex" refers to at least one chemical modifier covalently bound, optionally via a spacer group, to a pharmaceutical agent. Single or multiple chemical modifiers and according to some embodiments, single or multiple functionality modifiers, may be bound to a single pharmaceutical agent molecule to enhance the transport and delivery of the pharmaceutical agent. The chemical modifiers may be bound to different sites on the pharmaceutical agent molecule, bound to other chemical modifiers which in turn are bound to the pharmaceutical agent, or a combination of both. The term "pharmaceutical agent-chemical modifier complex" is meant to include both the charged molecule and any counterions. In other words, the net charge on the pharmaceutical agent-chemical modifier complex is zero.

Pharmaceutical agent-chemical modifier complexes may be schematically represented as pharmaceutical agent-[(spacer)$_x$-(chemical modifier)$_y$]$_z$ or A-(S$_x$-My)$_z$ wherein x is 0–10, y is 1–10 and z is 1–10 and A is the pharmaceutical agent, S is the spacer group, and M is the chemical modifier. In some embodiments, the pharmaceutical agent-chemical modifier complex will further comprise at least one functionality modifier.

"Model compound" refers to a compound which is relatively easy to synthesize and which can be used to validate or assess the methods described herein. More specifically, a model compound will comprise a "pharmaceutical agent"-chemical modifier complex in which the "pharmaceutical agent" is a substance not generally considered to be therapeutically effective in humans.

"Chemical functionality" refers to a chemically reactive moiety or group on the pharmaceutical agent, spacer group, functionality modifier, and/or chemical modifier through which the covalent bonding occurs to form the pharmaceutical agent-modifier complex.

"Physiologically cleavable bond" refers to a chemical bond which can be cleaved by physiological processes in a cell, an organ, the skin, a membrane, or the body of the patient. Cleavage can occur by enzymatic and nonenzymatic processes, such as by proteases, chemical hydrolysis, and the like.

"Penetration enhancer" refers to a substance which is used to increase the transdermal or transmembrane flux of a compound. A penetration enhancer is typically applied to the skin or mucous membrane in combination with the compound. Enhancers are believed to function by disrupting the skin or mucous membrane barrier or changing the partitioning behavior of the drug in the skin or mucous membrane.

"Protecting group" refers to a chemical group which generally exhibits the following characteristics: 1) the group must react selectively with the desired functionality in good yield to give a protected substrate that is stable to a future projected reaction; 2) the protecting group must be selectively removable from the protected substrate to yield the desired functionality; and 3) the protecting group must be removable in good yield by reagents that do not attack one or more of the other functional group(s) generated or present in the projected reaction. Examples of protecting groups can be found in Greene et al. *Protective Groups in Organic Synthesis,* 2nd Ed., John Wiley & Sons, New York (1991).

"Acyloxyalkyl amine" refers to the group —NH—CH$_m$R$_n$—O(CO)— where R is hydrogen, alkyl, aryl, aralkyl or heteroaryl and where m=0–2, n=0–2 and m+n=2. R may be a chemical modifier. In similar fashion, an "acyloxyalkylamide" is —(CO)—NR'—CH$_m$R$_n$—O(CO)— and an "acyloxyalkylamide" is —N(COR)—CH$_m$R$_n$'—O(CO)—, where R and R' are independently selected from the group consisting of hydrogen, alkyl, aryl, arylalkyl, and heteroaryl and where m=0–2, n=0–2 and m +n=2. R and R' may be chemical modifiers.

"Acyloxyalkyl carbamate" refers to the group —NR—(CO)O—CH$_m$R$_n$'—O(CO)— or —O—(CO)NR—

$CH_mR_n'$—O(CO)— where R and R' are independently hydrogen, alkyl, aryl, arylalkyl or heteroaryl and where m=0–2, n=0–2 and m+n=2. R and R' may be chemical modifiers.

"Acyloxyalkyl carbonyl" refers to the group —(CO)CH$_m$R$_n$—O(CO)— where R is hydrogen, alkyl, aryl, arylalkyl, or heteroaryl and where m=0–2, n=0–2 and m+n=2. R may be a chemical modifier.

"Acyloxyalkyl ester" refers to the group —CO$_2$—CH$_m$R$_n$—O(CO)— where R is hydrogen, alkyl, aryl, arylalkyl or heteroaryl and where m=0–2, n=0–2 and m+n=2. R may be a chemical modifier.

"Acyloxyalkyl ether" refers to the group —OCH$_m$R$_n$—O(CO)— where R is hydrogen, alkyl, aryl, arylalkyl or heteroaryl and where m=0–2, n=0–2 and m+n=2. R may be a chemical modifier.

"Acyloxyalkyl sulfonamide" refers to the group —SO$_2$—NR—CH$_m$R$_n'$—O(CO)— where R and R' are independently hydrogen, alkyl, aryl, arylalkyl or heteroaryl and where m=0–2, n=0–2 and m+n=2. R and R' may be chemical modifiers.

"Acyloxyalkyl thioether" refers to the group —SCH$_m$R$_n$—O(CO)— where R is hydrogen, alkyl, aryl, arylalkyl or heteroaryl and where m=0–2, n=0–2 and m+n=2. R may be a chemical modifier.

"Aldehyde" refers to the group —CHO.

"Alkoxycarbonyloxyalkyl ester" refers to the group —(CO)O—CH$_m$R$_n$—O(CO)OR' where R is hydrogen, alkyl, aryl, arylalkyl, or heteroaryl and where m=0–2, n=0–2 and m+n=2 and R'=alkyl or arylalkyl. R' or R may be a chemical modifier.

"Alkyl" refers to a cyclic, branched, or straight chain alkyl group containing only carbon and hydrogen. This term is further exemplified by groups such as methyl, heptyl, —(CH$_2$)$_2$—, and adamantyl. Alkyl groups can either be unsubstituted or substituted with one or more non-interfering substituents, e.g., halogen, alkoxy, acyloxy, hydroxy, mercapto, carboxy, benzyloxy, phenyl, benzyl, or other functionality which has been suitably blocked with a protecting group so as to render the functionality non-interfering. Each substituent may be optionally substituted with additional non-interfering substituents. The term "non-interfering" characterizes the substituents as not adversely affecting any reactions to be performed in accordance with the process of this invention.

"Amide" or "amido" refers to the groups —NR'(CO)R" and —(CO)NH$_m$R'$_n$, where R' and R" are independently selected from hydrogen, alkyl, aryl, arylalkyl, or heteroaryl and where m=0–2, n=0–2, and n+m=2.

"Aminal ester" refers to the group —N—(CRR')—O—(CO)—R" where R, R', and R" are independently hydrogen, alkyl, aryl, heteroaryl, or arylalkyl.

"Amino" refers to the group —NR'R", where R' and R" are independently hydrogen, alkyl, or aryl. If an amino group is to serve as a chemical functionality according to the present invention, either R' or R" must be hydrogen.

"Amino acid" refers to any of the naturally occurring amino acids, as well as synthetic analogs and derivatives thereof. a-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen, alkyl (e.g., as in glycine, alanine, valine, leucine, isoleucine, proline,), substituted alkyl (e.g., as in serine, cysteine, aspartic acid, asparagine, arginine, and lysine), arylalkyl (e.g., as in phenylalanine, histidine, and tryptophan), substituted arylalkyl (e.g., as in tyrosine and thyroxine), and heteroaryl (e.g., as in histidine). See, e.g., Harper et al. (1977) *Review Of Physiological Chemistry*, 16th Ed., Lange Medical Publications, pp. 21–24. One of skill in the art will appreciate that the term "amino acid" also includes β-, γ-, ε-, and ω-amino acids, and the like.

"Amino acid based drug" refers to a pharmaceutical agent or drug comprising an amino acid. Examples of amino-acid based drugs include, but are not limited to cephalosporins, proteins, and peptides.

"Anhydride" refers to the group —(CO)—O—(CO)—.

"Aryl" or "Ar" refers to a monovalent unsaturated aromatic carbocyclic group having a single ring (e.g., phenyl) or multiple condensed rings (e.g., naphthyl or anthryl), which can optionally be unsubstituted or substituted with hydroxy, lower alkyl, alkoxy, chloro, halo, mercapto, and other non-interfering substituents.

"Arylalkyl" refers to the groups —R—Ar and —R—HetAr, where Ar is an aryl group, HetAr is a heteroaryl group, and R is straight-chain or branched-chain aliphatic group. Examples of arylalkyl groups include benzyl and furfuryl.

"Carbamate" refers to the group —NH(CO)OR, —NR(CO)OR and —O(CO)NH$_m$R$_n$, where R is hydrogen, alkyl, aryl, arylalkyl, or heteroaryl and where m=0–2, n=0–2 and m+n=2.

"Carbonate" refers to the group —O(CO)O—.

"Carboxy" or "carboxylic acid" refers to the group —COOH.

"Disulfide" refers to the group —SS—.

"Enol ester" refers to the group —C=C—O(CO)—.

"Ester" refers to the group —(CO)O—R where R is alkyl, aryl, arylalkyl, or heteroaryl.

"Heteroaryl" or "HetAr" refers to a monovalent aromatic carbocyclic group having a single ring (e.g., pyridyl or furyl) or multiple condensed rings (e.g., indolizinyl or benzo[b]thienyl) and having at least one hetero atom, such as N, O or S, within the ring, which can optionally be unsubstituted or substituted with hydroxy, alkyl, alkoxy, halo, mercapto, and other non-interfering substituents.

"Heterocycle" or "heterocyclic" refers to a monovalent saturated, unsaturated, or aromatic carbocyclic group having a single ring or multiple condensed ring and having at least one hetero atom, such as N, O, or S, within the ring, which can optionally be unsubstituted or substituted with hdyroxy, alkyl, alkoxy, halo, mercapto, and other non-interfering substituents. Examples of nitrogen heterocycles include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline.

"Hydroxy or hydroxyl" refer to the group —OH.

"Hydroxymethyl ketone ester" refers to the group —(CO)—CH$_2$—O—(CO)R where R is alkyl, aryl, arylalkyl or heteroaryl. R may be a chemical modifier.

"Ketone or keto" refers to the group —(CO)—.

"N-Mannich base" refers to compounds formed through the reaction of amines with formaldehyde and certain reactive amide compounds. N-Mannich bases have moderate stability at acidic pH, but rapidly hydrolyse at physiological pH to liberate the free amino species. N-Mannich bases possess the group —NCH$_2$N—.

"Mercapto", "sulphydryl", or "thiol" refers to the group —SH.

"N-acylamide" refers to the group —(CO)—NR—(CO)— where R is hydrogen, alkyl, aryl, arylalkyl, or heteroaryl. R may be a chemical modifier.

"Nucleotide" refers to a phosphoric acid ester of a N-glycoside of a heterocyclic nitrogenous base and is meant to encompass both non-cyclic and cyclic derivatives. The phosphate can be present on position 2', 3', and/or 5'. Generally, the glycoside component will be a pentose, however, in some embodiments, hexoses will be employed. The nitrogenous base typically will be selected from the group consisting of adenine, guanine, hypoxanthine, uracil, cytosine, and thymine, and analogs or chemical modifications thereof.

"Nucleotide-based pharmaceutical agent" or "nucleotide-based drug" refer to a pharmaceutical agent or drug comprising a nucleotide, an oligonucleotide or a nucleic acid.

"Nucleotide-based chemical modifier" refers to a chemical modifier comprising a nucleotide, an oligonucleotide, or a nucleic acid.

"Nucleic acid" refers to either deoxyribonucleic acid (DNA) or ribonucleic acid (RNA), whether single-stranded or double-stranded, and any chemical modifications thereof. Such modifications include, but are not limited to, alternate linkages other than the conventional phosphodiester linkage, modifications at cytosine exocyclic amines, substitution of 5-bromouracil, backbone modifications, base analogs, methylations, unusual base-pairing combinations, and the like. Examples of alternate linkages include the methylphosphonates wherein one of the phosphorous-linked oxygens has been replaced by methyl; phosphorothioates, wherein sulfur replaces one of the oxygens; various amidates, wherein NH$_2$ or organic amine derivatives, such as morpholidates or piperazidates, replace an oxygen; carbonate and carbamate linkages; and linkages involving sulfur rather than oxygen as the linking substituent.

"N-sulfonylimidate" refers to the group —SO$_2$—N=C(OR')R where R and R' are independently hydrogen, alkyl, aryl, arylalkyl or heteroaryl. R and R' may be chemical modifiers.

"Oligonucleotide" generally refers to linear sequences of nucleotides, joined by phosphodiester bonds, typically prepared by synthetic means. Position 3' of each nucleotide unit is linked via a phosphate group to position 5' of the next unit. In the terminal units, the respective 3' and 5' positions can be free (i.e., free hydroxyl groups) or phosphorylated. Those oligonucleotides employed in the present invention will vary widely in length. Suitable oligonucleotides can be prepared by the phosphoramidite method described by Beaucage and Carruthers, *Tetra. Letts.* 22:1859–1862 (1981), or by the triester method according to Matteucci, et al., *J. Am. Chem. Soc.*, 103:3185 (1981), or by other methods, such as commercial automated oligonucleotide synthesizers. Oligonucleotide also is meant to include chemical modifications of the naturally occurring oligonucleotide skeleton. Such modifications include, but are not limited to, modifications at cytosine exocyclic amines, substitution of 5-bromouracil, backbone modifications, base analogs, methylations, and the like.

"Phosphate" refers to the group —OPO$_3$= as well as its monoester, —O(PO)(OR)O$^-$ where R is alkyl, aryl, arylalkyl or heteroaryl.

"Phosphate ester" refers to a compound having the general formula RO(PO)(OR')(OR"), where R, R' and R" are independently selected from hydrogen, alkyl, aryl, arylalkyl, and heteroaryl.

"Phosphodiester" refers to a phosphate ester in which two hydroxyl groups of the phosphoric acid are esterified with organic residues: R'O—PO2H—OR" where R' and R" are independently selected from the group consisting of hydrogen, alkyl, aryl, arylalkyl, or heteroaryl. Oligonucleotides and nucleic acids are typically phosphodiesters in which the 3' and 5' positions of neighboring pentose units are linked by esterification with a phosphate residue.

"Phosphoramidate" refers to a phosphodiester in which one or more of the hydroxyl groups is replaced with an amino group.

"Quaternary ammonium salt" refers to the positively charged group —N$^+$R'R"R"', where R', R", and R"' are independently alkyl or aryl.

"Sulfate" refers to the group —OSO$_3^-$.

"Sulfonamide" refers to the group —SO$_2$NH$_m$R$_n$ where R is hydrogen, alkyl, aryl, arylalkyl, or heteroaryl and where m=0–2, n=0–2 and m+n=2. R may be a chemical modifier.

"Thioester" refers to the group —(CO)S—R where R is alkyl, aryl, arylalkyl, or heteroaryl.

"Urea" refers to the group —NH(CO)—NH—.

"Pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system.

II. THE PHARMACEUTICAL AGENT-MODIFIER COMPLEX

In accordance with the present invention, novel methods for enhancing the transport and delivery of pharmaceutical agents in a controlled fashion are provided through the use of chemical modifiers. More generally, however, the present invention relates to methods of derivatizing pharmaceutical agents so as to improve a useful biological property of the pharmaceutical agent. For example, properties of the pharmaceutical agent that may be enhanced or altered using the methods of the present invention include its transport rate, its delivery rate, its serum half-life, and its biodistribution, including the enhancement of its pharmacokinetic and pharmacodynamic properties, such as its lipophilicity and/or its solubility, and its partition coefficient. The methods described herein also will find use for decreasing the inflammation and/or irritation accompanying the delivery of the pharmaceutical agent across membranes.

In addition, because diffusion through the blood-brain barrier is largely dependent on the lipid solubility of the substance, the methods of the present invention can be utilized to modify a pharmaceutical agent's ability to pass through the blood-brain barrier. Likewise, the agent's ability to transport through the placental barrier can also be altered using the compositions and methods described herein. Also provided are chemical modifiers that safely and reversibly add charge to pharmaceutical agents.

A. The Pharmaceutical Agent i. General

Preferred pharmaceutical agents that best can be modified for transmembrane transport are those effective at low concentrations, for example, less than 50 milligrams per day, or are topically administered. Marked improvements in pharmaceutical agent bioavailability can be expected for those pharmaceutical agents that are poorly absorbed enterally or undergo extensive first pass hepatic inactivation.

Pharmaceutical agents, according to the present invention, should possess (or be capable of being modified to possess) at least one chemical functionality that can be altered with chemical modifiers or that can be substituted with or otherwise covalently coupled to a charged group. Preferred forms of chemical functionality include hydroxy, carboxy, amino, ketone, mercapto, sulfonamide, and amide groups.

Exemplary pharmaceutical agents or drugs that may be delivered by the system of the present invention include analgesics, anesthetics, antifungals, antibiotics, antiinflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, corticoids (steroids), antidepressants, depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasoconstrictors, vasodilators, vitamins, xanthine derivatives, and the like.

Examples of pharmaceutical agents with recommended dosage levels of less than 50 mg/day and thus, preferred for modification with chemical modifiers according to the present invention so as to improve the delivery and/or transport of the agents through membranes include the compounds set forth in Table 1.

TABLE 1

Generic Names of Pharmaceutical Agents

| | |
|---|---|
| Medroxyprogesterone acetate | Cyclobenzaprine HCl |
| Stanozolol | Piroxicam |
| Methadone HCl | Triamcinolone acetonide |
| Alprazolam | Terbutaline sulfate |
| Lorazepam | Methylphenidate HCl |
| Glcopyrolate | Glipizide |
| Warfarin sodium | Amiloride HCl |
| Clonazepam | Bendroflumethiazide |
| Ergoloid mesylates | Polythiazide |
| Protriptyline HCl | Bumetanide |
| Glyburide | Desmopressin acetate |
| Nabilone | Triamcinolone |
| Thiethylperazine maleate | Somatrem |

TABLE 1-continued

Generic Names of Pharmaceutical Agents

| | |
|---|---|
| Cyproheptadine HCl | Digitoxin |
| Pergolide mesylate | Bromocriptine mesylate |
| Biperiden HCl | Carteolol HCl |
| Procyclidine HCl | Methyclothiazide |
| Trihexyphenidyl HCl | Deserpidine |
| Benztropine mesylate | Terazosin HCl |
| Selegiline HCl | Reserpine |
| Trimeprazine tartrate | Metolazone |
| Pimozide | Mecamylamine HCl |
| Haloperidol | Lisinopril |
| Thiothixene HCl | Desoxymetasone |
| Fluphenazine | Triamcinolone acetonide |
| Perphenazine | Amcinonide |
| Trifluoperazine HCl | Dexamethasone |
| | Desonide |
| | Halcinonide |
| | Hydrocortisone |
| | Pramoxine HCl |
| | Fluocinolone acetonide 21-acetate |
| Salicylic add | Yohimbine HCl |
| Enalapril maleate | Quazepam |
| Prazosin HCl | Dextrothyroxine Na |
| Rescinnamine | Misoprostol |
| Polythiazide | Mazindol |
| Guanfacine HCl | Menotropins |
| Pindolol | Clidinium bromide |
| Indapamide | Isopropamide iodide |
| Metolazone | Auranofin |
| Methyclothiazide | Diazepam |
| Calcifediol | Methylergonovine maleate |
| Dihydrotachysterol | Fluoxymesterone |
| Menadiol Na diphosphate | Oxybutynin chloride |
| Levothyroxine Na | Methysergide maleate |
| Liotrix | Nylidrin HCl |
| Thyroglobulin | |
| Erythromycin | Haloprogin |
| Clindamycin phosphate | Buspirone HCl |
| Estradiol | Famotidine |
| Mupirocin | Beclomethasone |
| Progesterone | triazolam |
| Digoxin | Diflorasone |
| Indomethacin | Clioquinol |
| Anthralin | Mometasone furoate |
| Butamben picrate | Chlorcyclizine |
| Pramoxine HCl | Acyclovir |
| Dyclonine HCl | Pravastatin |
| Polymyxin B sulfate | Lovastatin |
| Gentamicin sulfate | Alclometasone dipropionate |
| Difluorasne diacetate | Megestrol acetate |
| Clotrimazole | Methimazole |
| Fluoxetine | Vitamin B12 |
| Betamethasone Clioquinol | Midolazam |
| Oxiconazole nitrate | Prochlorperazine |
| Naftifine HCl | Flumazenil |
| Sulconazole nitrate | Propofol |
| Selegilene | MDL-72222 |
| Sincalide | RS-42358 (investigational antiemetic, Syntex) |
| Tamoxifen | |
| Terprazosin | Dolasetron |
| Thiothixene | BMY-25801-01 (investigational antiemetic, Bristol-Myers) |
| Felodipene | |
| Ipratroprium bromide | LY 303366, LY 295337, LY 303208, and LY 302146 (investigational antifungal agents, Eli Lilly and Co.) |
| Colchicine | |
| Omeprazole | |
| Buprenorphine | |
| Sumatriptan | |
| Low molecular weight heparins | FR 901379 (investigational antifungal agent, Fujisawa Pharmaceutical Co., Japan) |
| Cisapride | |
| Parlodel | L-731,373, L-705,589, and L-733,560 (investigational antifungal agents, Merck Research Labs) |
| Trimetrexate | |
| Sufentanyl | |
| Domperidone | |
| Ororax | Ceftirizine |
| Tropisetron | Gentamycin |
| Granisetron | Iloprost |

TABLE 1-continued

| Generic Names of Pharmaceutical Agents | |
|---|---|
| Ondansetron | Mestinon |
| Oxazepam | Ritodrine |
| Piretanide | Clonidine |
| Torasemide | Droperidol |
| Dazopride | | ii. Digitalis Drugs

Preferred examples of pharmaceutical agents include the digitalis drugs, such as digoxin, digitoxin, digoxigenin, and digitoxigenin. These drugs are all primarily used as cardiac agents. However, they differ widely in their pharmacokinetics properties.

Digoxin (3β,5β,12β-3-[(O-2,6-dideoxy-β-D-ribohexopyranosyl(1→4)-O-2,6-dideoxy-β-D-ribo-hexopyranosyl-(1→4)-2,6-dideoxy-β-D-ribo-hexopyranosyl)oxy]-12,14-dihydroxycard-20(22)-enolide) and digitoxin (3β,5β-3-[(O-2,6-dideoxy-β-D-ribo-hexopyranosyl(1→4)-O-2,6-dideoxy-β-D-ribo-hexopyranosyl-(1→4)-2,6-dideoxy-β-D-ribohexopyranosyl)oxy]-14-hydroxycard-20(22)-enolide) are two digitalis compounds available as pharmaceutical agents.

Both digoxin and digitoxin are glycosides with three digitoxose residues attached. The amount of each compound absorbed depends largely on its polarity, which is a function of the net electronic charge on the molecule. The more nonpolar or lipid soluble, the better is the absorption, because of the greater permeability of lipid membrane of the intestinal mucosa for lipid-soluble substances. The nonpolar, lipophilic digitoxin is completely absorbed. Other digitalis glycosides are not as well absorbed. For example, nonpolar digoxin is over 90% bound to tissue proteins. Digoxin also crosses both the blood-brain barrier and the placenta.

Digitoxin differs from the other commonly used digitalis glycosides not only in its firm binding to protein but also because it is metabolized in the liver, with the only active metabolite being digoxin. The portion of digitoxin that is bound to protein is in equilibrium with free digitoxin in the serum. Thus, as more and more of the free digitoxin is metabolized, there is proportionately less bound digitoxin. Digitoxin is the most slowly secreted of the digitalis compounds.

Digoxin possesses five secondary hydroxyl and one tertiary hydroxyls, whereas digitoxin has four secondary and one tertiary hydroxyl groups. The tertiary hydroxyl is not readily esterified. However, one or more of the secondary hydroxyls may serve as a chemical functionality to form linkages to chemical modifiers or spacer groups.

Cleavage of the tridigitoxose moieties from digoxin and digitoxin yields digoxigenin and digitoxigenin, respectively. Digoxigenin (3,12,14-trihydroxycard-20(22)-enolide) contains two secondary hydroxyls and digitoxigenin (3,14-dihydroxycard-20(22)-enolide) contains one secondary hydroxyl which may be used to form linkages with chemical modifiers or spacer groups.

iii. Steroidal Compounds

Steroidal compounds form another preferred class of pharmaceutical agent. An example of a steroidal pharmaceutical agent is testosterone (17 β-hydroxyandrost-4-en-3-one), the principal male steroid. Its main therapeutic use is in the treatment of deficient endocrine function of the testes. Testosterone contains a single hydroxyl group, the 17 β-hydroxyl group, which may be used to form linkages with chemical modifiers or spacer groups.

Estradiol (estra-1,3,5(10)-triene-3,17β-diol) is also a preferred steroidal pharmaceutical agent. Estradiol and its ester derivatives are indicated for the treatment of symptoms of menopause and other conditions that cause a deficiency of endogenous estrogen production. The two hydroxyl groups of estradiol serve as chemical functionalities for forming bonds with chemical modifiers or spacer groups.

Progesterone is also a preferred steroidal pharmaceutical agent. Progesterone is used primarily to suppress or synchronize estrus as well as to control habitual abortion and diagnose and treat menstrual disorders. The enone and ketone groups may be utilized to form bonds with chemical modifiers or spacer groups.

Additional preferred steroidal pharmaceutical agents include 3-hydroxy-5α-pregnan-20-one (with a hydroxyl group and a ketone as chemical functionalities), 3-β-hydroxy-pregn-5-ene-20-one (with a hydroxyl and a ketone group as chemical functionalities), and related compounds.

iv. Nonsteroidal Anti-inflammatory Drugs

Piroxicam (4-hydroxy-2-methyl-N-2-pyridinyl-2H-1,2-benzothiazine-3-carboxamide 1,1-dioxide) and indomethacin (1-(4-chlorobenzoyl)-5-methoxy-2-methyl-1H-indole-3-acetic acid) are nonsteroidal anti-inflammatory, analgesic, and antipyretic drugs used in the treatment of osteoarthritis and rheumatoid arthritis. The phenolic hydroxyl group of piroxicam serves as a chemical functionality and can be linked to a chemical modifier or spacer group. Indomethacin possesses a carboxy group as its chemical functionality.

v. Protein and Peptide Drugs

Protein and peptide drugs, as well as other amino acid-based drugs, may also be used as pharmaceutical agents according to the present invention. The problems associated with conventional delivery strategies for protein and peptide drugs are widely appreciated. Oral administration of these drugs is generally impractical due to degradation and nonabsorption in the gastrointestinal tract. Thus, the parenteral route remains the principal delivery route.

Protein and peptide drugs are capable of either covalently binding to a chemical modifier and so can serve as pharmaceutical agents according to the present invention. For example, most protein and peptide drugs possess either an amino, carboxy, hydroxy, or mercapto group that can be used to bind covalently to a chemical modifier or spacer group. According to this aspect of the invention, particularly preferred as protein and peptide drugs include those which contain either a cysteine or a lysine residue. The mercapto group of cysteine and the E-amino group of lysine can be used as chemical functionality to bind to a chemical modifier or spacer group. See, also copending application Serial No. (Attorney docket No. 11509-92), filed May 24, 1993.

In the case of certain protein and peptide drugs, additional chemical functionality can be introduced into the drug by site-directed mutagenesis. For example, protein and peptide drugs which are not amenable to coupling with a chemical modifier can be modified using recombinant DNA techniques. These modifications could entail the replacement of an existing amino acid of the drug with an amino acid or other group which can be easily coupled to a chemical modifier or the addition of amino acid(s) or other group(s) which can be easily coupled to a chemical modifier. In some instances, the net charge, charge distribution, or charge localization of the protein itself is modified using recombinant techniques (infra) thus, eliminating the necessity of additional bonding to a chemical modifier.

Amino acid-based drugs, such as the cephalosporins, will typically have a molecular weight less than about 5000, and preferably, less than about 2500, and more preferably, less than about 1000. Protein and peptide drugs typically have a molecule weight of at least about 100 daltons, and more typically a molecular weight in the range of about 200 to 40,000 daltons. Specific examples of peptides and proteins in this size range include, but are not limited to, those found in Table 2.

TABLE 2

Examples of Peptide and Protein Drugs

| | |
|---|---|
| Luteinizing hormone-releasing hormone | Somatostatin |
| Goserelin | Bradykinin |
| Buserelin | Somatotropin |
| Triptorelin | Platelet-derived growth factor |
| Gonadorelin | Asparaginase |
| Nafarelin | Bleomycin sulfate |
| Leuprolide | Chymopapain |
| Growth hormone-releasing factor | Cholecystokinin |
| Insulin | Chorionic gonadotropin |
| Calcitonin (e.g., eel, salmon, human) | Corticotropin (ACTH) |
| | Erythropoietin |
| Calcitonin gene related peptide | Glucagon |
| | Hyaluronidase |
| Endorphin (alpha, beta, and gamma) | Interferons, e.g., alpha, beta, and gamma |
| Thyrotropin-releasing hormone | Interleukins, e.g., IL-1 receptor antagonist; IL-10; CSIF (cytokine synthesis inhibitory factor); IL-11; IL-6; IL-4; and IL-2 |
| NT-36 (N-[[(s)-4-oxo-2-azetidinyl]carbonyl]-L-histidyl-L-prolinamide) | |
| Liprecin | Menotropins |
| Pituitary hormones (e.g., HGH, HMG, HCG, desmopressin acetate, etc.) | Urofollitropin (Follicle stimulating hormone, FSH) |
| Follicle luteoids | Leutinizing hormone (LH) |
| aANF growth factor releasing factor (GFRF) | LH-releasing hormone (LHRH) |
| Melanocyte-stimulating hormone (alpha, beta, and gamma) | Gonadotropin releasing hormone |
| | Oxytocin |
| Vasopressin | Streptokinase |
| ACTH analogs | Tissue plasminogen activator |
| Atrial natriuretic peptide | Urokinase |
| ANP clearance inhibitors | Bradykinin potentiator B |
| Angiotensin II antagonists | Bradykinin potentiator C |
| Bradykinin antagonists | Brain-derived neurotrophic factor |
| CD4 | |
| Ceredase | Cystic fibrosis transmembrane conduct regulator (CFTR) |
| Colony stimulating factors | |
| Enkephalins | |
| FAB fragments | |
| IgE peptide suppressors | Chorionic gonadotropin |
| Insulin-like growth factors | Ciliary neurotrophic factor (CNTF) |
| Neurotrophic factors | |
| Parathyroid hormone agonists and antagonists | Corticotropin-releasing factor (CFR) |
| Prostaglandin antagonists | Granuloycte colony stimulating factor, filgrastim. (G-CSF) |
| Pentigetide | |
| Protein C | |
| Protein S | Granulocyte macrophage colony stim. factor. sargramostrim. (GM-CSF) |
| Renin inhibitors | |
| Thymosin a-1 | |
| Thrombolytics | Multilineage colony stimulating factor (CSF) |
| Tumor necrosis factor | |
| Vaccines | Macrophage-specific colony stimulating factor (CSF-1) |
| Vasopressin antagonist analogs | Colony stimulating factor 4 (CSF-4) |
| a-1 Anti-trypsin | |
| Adenosine deaminase | Epidermal growth factor (EGF) |
| Amylin | |
| Atrial natriuretic peptide | Enkephalin leu |
| β-Glucocerebrosidase | Enkephalin met |
| Bone morphogenesis protein 2 | Factor IX |
| Bombesin | Factor VIII |
| Bactericidal/permability increasing protein | Follicular gonadotropin releasing peptide |
| Hirudin | G-1128 |

TABLE 2-continued

Examples of Peptide and Protein Drugs

| | |
|---|---|
| IEV inhibitor peptide | Gastrin-releasing peptide |
| Inhibin-like peptide | Glucagon |
| Insulinotropin | Growth hormone releasing factor (GRF) |
| Lipotropin | |
| Macrophage-derived neutrophil chemotaxis factor | Heparin binding neurotrophic factor (HBNF) |
| Magainin I/II | |
| Melatonin, tryptophan hydroxylase | Fibroblast growth factor (FGF) |
| Midkine (MK) | Somatostatin |
| Neurophysin | Somatotropin |
| Neurotrophin-3 | (20 kd and 22 kd forms) |
| Nerve growth factor (NGF) | |
| Oxytocin | (extracellular, Cu/Zn, and manganese-containing) |
| Phospholipase A2 | |
| Sauvagine | Thymidine kinaise (TK) |
| Soluble IL-1 receptor | Thymosin alpha one |
| | TNF receptor, soluble |
| | TPA (alteplase, tissue plasminogen activator) |
| | Transforming growth factor beta |
| | TRH (TSH-releasing hormone) |
| | Thyroid stimulating hormone (TSH) |
| | Vasopressin |
| | Vasotocin |

In an illustrative embodiment, the protein or peptide drug is one of the highly related sequences of alpha interferon 2 (IFN-α2). IFN-α2a (sold by Roche as Roferon A) and INF-α2b (sold by Schering as Intron A) are 19 kilodalton (kDa) proteins of 165 amino acids. These proteins contain two pairs of disulfide linked cysteines and include 20 basic and 22 acidic residues for a net positive charge of approximately −1.69 at neutral pH. IFN has been used as an antiproliferative agent in the treatment of renal cell carcinoma, hairy cell leukemia, Kaposi's sarcoma, melanoma, and T-cell lymphoma, as well as an antiviral agent in the treatment of non-A,B-hepatitis, genital warts, Epstein-Barr virus, CMV, AIDS, and rhinovirus.

An additional example of a preferred peptide pharmaceutical agent is parathyroid hormone. See copending application U.S. Ser. No. 07/965,677 which is hereby incorporated by reference. Parathyroid hormone (PTH) is a linear polypeptide consisting of 84 amino acids. See Harper et al., Eds., *Review of Physiological Chemistry*, 16th Ed., Lange Medical Publications, Los Altos, Calif. (1977) p. 468. However, a fragment consisting of about 34 amino acid residues from the N-terminal has been isolated and found to display the full biological activity of PTH. See Potts et al., in *Parathyroid Hormone and Thyrocalcitonin (Calcitonin)*, R. V. Talmage, et al., Eds. Excerpta Medica, New York (1968). The sequence of the polypeptide varies slightly among mammalian species. According to the present invention, PTH is meant to include human parathyroid hormone, as well as the other variants and the 34 amino acid fragment. PTH contains a variety of chemical functionalities (e.g., hydroxyl groups from serine residues, carboxylic acid groups from aspartic acid residues, and amino groups from glutamine, lysine, and arginine residues) which may potentially be used to bind to chemical modifiers.

PTH serves as a regulatory factor in the homeostatic control of calcium and phosphate metabolism. See, e.g., Parsons, et al. "Physiology and Chemistry of Parathyroid Hormone" in *Clinics in Endocrinology and Metabolism*, I. MacIntyre, Ed. Saunders, Philadelphia (1972) pp. 33–78.

The main therapeutic use for PTH is in the treatment of osteoporosis. PTH has also been used as a blood calcium regulator.

Calcitonin is also a preferred peptide pharmaceutical agent. Calcitonin is a polypeptide containing 32 amino acid residues. See Harper et al., Eds., *Review of Physiological Chemistry*, 16th Ed., Lange Medical Publications, Los Altos, Calif. (1977), p. 469, which is incorporated herein by reference. The amino acid sequence differs among mammalian and fish species. According to the present invention, calcitonin is meant to include all calcitonin, including that of humans, mammals, and fish, as well as other variants. Calcitonin contains several chemical functionalities (e.g., hydroxly groups from serine residues, mercapto groups from cysteine residues, amino groups from lysine and amide groups from glutamine, and asparagine, and guanidino groups from arginine residues) which may potentially be used to bind to chemical modifiers. Calcitonin is a calcium regulating hormone and has been used in the treatment of osteoporosis, hypercalcemia, and Paget's disease.

An additional preferred protein drug is the cytokine IL-10. Il-10 is produced by the TH2 helper subset, B cell subsets and LPs-activated monocytes. IL-10 inhibits several immune functions that are relevant to the skin immune response and thus, the development of the irritation and inflammation that is sometimes associated with the transdermal or iontophoretic delivery of drugs. More specifically, the release of IFN-α, which initiates the cascade of cellular activation leading to the skin's immune response, is inhibited by IL-10. IL-10 also suppresses the synthesis of numerous proinflammatory cytokines by macrophages, as well as the proliferation of antigen-specific T cell proliferation by down regulating class II MHC expression.

Thus, the present invention also contemplates the simultaneous or sequential transdermal, either passively or iontophoretically, delivery of a drug that elicits inflammation or irritation with a pharmaceutical agent-chemical modifier complex wherein the pharmaceutical agent is IL-10, or an analog thereof. The complex is delivered in an amount sufficient to prevent the inflammation and irritation generally associated with delivery of the other drug.

Other preferred protein and peptide drugs and amino acid-based pharmaceutical agents include G-CSF, a colony stimulating factor that stimulates production of granulocytes, particularly neutrophils; GM-CSF, a colony stimulating factor that stimulates production of granulocytes/macrophages/monocytes; human growth factor; insulin, a hormone (protein) naturally secreted by the β cells of the pancreas (when stimulated by glucose and the parasympathetic nervous system); antibodies (subfragments); EPO, a glycoprotein hormone produced in the kidneys which stimulates the bone marrow to produce red blood cells; the interleukins; interferon-gamma, a cytokine protein produced by vertebrate cells following a virus infection and possessing potent antiviral effects; Vasotec®, a antihypertensive (Enalapril maleate, Merck, Sharp & Dohme, West Point, Pa.) Capoten®, a antihypertensive (Captopril, E. R. Squibb & Sons, Inc., Princeton, N.J.); Rocephin®, an antiinfective (ceftriaxone sodium, Roche); Augmentin®, an antiinfective (Smith Kline & French Laboratories, Philadelphia, Pa.); Ceclor®, an antiinfective (Cefaclor, 3-chloro-7-D-(2-phenylglycinamido)-3-cephem-4-carboxylic acid, Eli Lilly and Company, Indianapolis, Ind.); Sandimmune®, an immunosuppressive (cyclosporine, a cyclic polypeptide consisting of 11 amino acids, Sandoz Pharmaceuticals Corporation, East Hanover, N.J.); Premaxin®, an antiinfective (Imipenem-cilastatin sodium, Merck); Fortaz®, an antiinfective (ceftazidime, Glaxo Pharmaceuticals, Research Triangle Park, N.C.); Amoxil, an antiinfective (amoxicillin, Beecham Laboratories, Bristol, Tenn.); Humulin®, an antidiabetic (human insulin recombinant DNA origin, Lilly); Epogen®, an erthyropoiesis enhancer (Epoetin alfa, a 165 amino acid glycoprotein manufactured by recombinant DNA technology with the same biological effects as endogenous erythropoietin, Amgen Inc., Thousand Oaks, Calif.); and Procrit®, an erthyropoiesis enhancer (Epoetin alfa, Ortho Biotech, Raritan, N.J.).

vi. Nucleotide-based Drugs

Heretofore, nucleotide-based drugs have had limited success as therapeutic agents, in part, because of problems associated with their stability and delivery. Nucleotide-based pharmaceutical agents frequently contain a phosphodiester bond which is sensitive to degradation by nucleases. Such degradation would be a significant impediment to the use of an oligonucleotide or nucleic acid as a pharmaceutical agent that depends upon the integrity of the sequence for its recognition specificity. Thus, naturally occurring oligonucleotides and nucleic acids often must be chemically modified to render them resistant to nucleases which would degrade them in vivo, or even in vitro unless care is taken to choose appropriate conditions.

The nucleotide-based drugs of the present invention include aptamers, antisense compounds, and triple helix drugs. Typically, a hydroxyl group of a sugar residue, an amino group from a base residue, or a phosphate oxygen of the nucleotide will be utilized as the needed chemical functionality to couple the nucleotide-based drug to the chemical modifier. However, one of skill in the art will readily appreciate that other chemical functionalities can be prepared by conventional techniques. For example, the hydroxyl group of the sugar residue can be converted to a mercapto or amino group using techniques well known in the art.

The nucleotide-based drugs typically will have a molecular weight greater than about 350 and may range up to about 100 bases. Examples of nucleotide-based drugs include di- and trinucleotides, such as GS 375, a dinucleotide analog with potential therapeutic activity against the influenza virus (Gilead Sciences, Inc., Foster City, Calif.), aptamers, antisense compounds, and triple helix drugs.

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Aptamers possess chemical functionality and thus, can covalently bond to chemical modifiers and/or serve as chemical modifiers, according to the methods described herein.

Although a wide variety of molecular targets will be capable of forming non-covalent but specific associations with aptamers, including small molecules drugs, metabolites, cofactors, toxins, saccharide-based drugs, nucleotide-based drugs, glycoproteins, and the like, generally the molecular target will comprise a protein or peptide, including serum proteins, kinins, eicosanoids, cell surface molecules, and the like. Examples of aptamers include Gilead's antithrombin inhibitor GS 522 and its derivatives (Gilead Science, Foster City, Calif.). See also Macaya et al. (1993) *Proc. Natl. Acad. Sci. USA* 90:3745–9; Bock et al. (1992) *Nature* (London) 355:564–566 and Wang et al. (1993) *Biochem.* 32:1899–904.

Aptamers specific for a given biomolecule can be identified by using techniques known in the art. See, e.g., Toole et al. (1992) PCT Publication No. WO 92/14843; Tuerk and Gold (1991) PCT Publication No. WO 91/19813; Weintraub and Hutchinson (1992) PCT Publication No. 92/05285; and Ellington and Szostak (1990) *Nature* 346:818. Briefly, these techniques typically involve the complexation of the molecular target with a random mixture of oligonucleotides. The aptamer-molecular target complex is separated from the uncomplexed oligonucleotides. The aptamer is recovered from the separated complex and amplified. This cycle is repeated to identify those aptamer sequences with the highest affinity for the molecular target.

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript which is essential for pre-mRNA processing, or to a sequence within the gene itself. This paradigm for genetic control is often referred to as antisense or antigene inhibition.

Antisense compounds are oligonucleotides that are designed to bind and disable or prevent the production of the mRNA responsible for generating a particular protein. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching et al. *Proc. Natl. Acad. Sci. U.S.A.* 86:10006–10010 (1989); Broder et al. *Ann. Int. Med.* 113:604–618 (1990); Loreau et al. *FEBS Letters* 274:53–56 (1990); Holcenberg et al. WO91/11535; U.S. Ser. No. 07/530,165 ("New human CRIPTO gene"); WO91/09865; WO91/04753; WO90/13641; WO 91/13080, WO 91/06629, and EP 386563).

Antisense compounds can provide a therapeutic function by inhibiting in vivo the formation of one or more proteins that cause or are involved with disease. Antisense compounds complementary to certain gene messenger RNA or viral sequences have been reported to inhibit the spread of disease related to viral and retroviral infectious agents (See, for example, Matsukura et al. (1987) Proc. Natl. Acad. Sci. USA 84:7706, and references cited therein).

Others have reported that oligonucleotides can bind to duplex DNA via triple helix formation and inhibit transcription and/or DNA synthesis. Triple helix compounds (also referred to as triple strand drugs) are oligonucleotides that bind to sequences of double-stranded DNA and are intended to inhibit selectively the transcription of disease-causing genes, such as viral genes, e.g., HIV and herpes simplex virus, and oncogenes, i.e., they stop protein production at the cell nucleus. These drugs bind directly to the double stranded DNA in the cell's genome to form a triple helix and thus, prevents the cell from making a target protein. See, e.g., PCT publications Nos. WO 92/10590, WO 92/09705, WO91/06626, and U.S. Pat. No. 5,176,996.

The site specificity of oligonucleotides (e.g., antisense compounds and triple helix drugs) is not significantly affected by modification of the phosphodiester linkage or by chemical modification of the oligonucleotide terminus. Consequently, these oligonucleotides can be chemically modified; enhancing the overall binding stability, increasing the stability with respect to chemical degradation, increasing the rate at which the oligonucleotides are transported into cells, and conferring chemical reactivity to the molecules. The general approach to constructing various oligonucleotides useful in antisense therapy has been reviewed by vander Krol et al. (1988) *Biotechniques* 6:958–976 and Stein et al. (1988) *Cancer Res.* 48:2659–2668.

Accordingly, aptamers, antisense compounds and triple helix drugs also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, e.g., Campbell et al. (1990) *J. Biochem. Biophys. Methods* 20:259–267). Phosphoramidate derivatives of oligonucleotides also are known to bind to complementary polynucleotides and have the additional capability of accommodating covalently attached ligand species and will be amenable to the methods of the present invention. See, for example, Froehler et al. (1988) *Nucleic Acids Res.* 16(11):4831.

In some embodiments the aptamers, antisense compounds and triple helix drugs will comprise O-methylribonucleotides (EP Publication No. 360609). Chimeric oligonucleotides may also be used (Dagle et al. (1990) *Nucleic Acids Res.* 18: 4751). For some applications, antisense oligonucleotides and triple helix may comprise polyamide nucleic acids (Nielsen et al. (1991) *Science* 254:1497 and PCT publication No. WO 90/15065) or other cationic derivatives (Letsinger et al. (1988) *J. Am. Chem. Soc.* 110:4470–4471). Other applications may utilize oligonucleotides wherein one or more of the phosphodiester linkages has been substituted with an isosteric group, such as a 2–4 atom long internucleoside linkage as described in PCT publication Nos. WO 92/05186 and 91/06556, or a formacetal group (Matteucci et al. (1991) *J. Am. Chem. Soc.* 113:7767–7768) or an amide group (Nielsen et al. (1991) *Science* 254:1497–1500).

In addition, nucleotide analogs, for example wherein the sugar or base is chemically modified, can be employed in the present invention. "Analogous" forms of purines and pyrimidines are those generally known in the art, many of which are used as chemotherapeutic agents. An exemplary but not exhaustive list includes 4-acetylcytosine, 5-(carboxyhydroxylmethyl) uracil, 5-fluorouracil, 5-bromouracil, 5-carboxymethylaminomethyl- 2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, β-D-mannosylqueosine, 5′methoxycarbonylmethyluracil, 5-methoxyuracil, 2-methylthio-$N^6$-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine. In addition, the conventional bases by halogenated bases. Furthermore, the 2'-furanose position on the base can have a non-charged bulky group substitution. Examples of non-charged bulky groups include branched alkyls, sugars and branched sugars.

Terminal modification also provides a useful procedure to modify cell type specificity, pharmacokinetics, nuclear permeability, and absolute cell uptake rate for oligonucleotide pharmaceutical agents. For example, substitutions at the 5' and 3' ends include reactive groups which allow covalent crosslinking of the nucleotide-based pharmaceutical agent to other species and bulky groups which improve cellular uptake. See, e.g., *Oligodeoxynucleotides: Antisense Inhibitors of Gene Expression,* (1989) Cohen, Ed., CRC Press; *Prospects for Antisense Nucleic Acid Therapeutics for Cancer and AIDS,* (1991), Wickstrom, Ed., Wiley-Liss; *Gene Regulation: Biology of Antisense RNA and DNA,* (1992) Erickson and Izant, Eds., Raven Press; and *Antisense RNA and DNA,* (1992), Murray, Ed., Wiley-Liss. For general methods relating to antisense compounds, see Antisense RNA and DNA, (1988), D. A. Melton, Ed., Cold Spring Harbor Laboratory, Cold Spring Harbor, N.Y.).

Antisense polynucleotides of various lengths may be delivered, although such antisense polynucleotides typically comprise a sequence of at least about 15 consecutive nucleotides. Examples of antisense compounds include G 1128 (Genta, Inc., San Diego, Calif.), OL(1)p53 (Lynx Pharmaceuticals), Ampligen (Hemm Pharmaceuticals), Isis 1082 and Isis 2105 (Isis Pharmaceuticals, Carlsbad, Calif.). Typically, the triple helix drug will comprise a DNA oligonucleotide in the range of about 20 to 40 bases.

vii. Heterocyclic Drugs

Heterocyclic drugs, and particularly those containing at least one nitrogen heterocyclic ring can be employed as pharmaceutical agents in the methods described herein. For example, yohimbine is an indole alkaloid that blocks α-2-adrenergic receptors. Its peripheral effects are to increase cholinergic activity at the same time that it decreases adrenergic activity. This combination has led to the use of yohimbine in the treatment and diagnostic classification of certain types of male erectile impotence. Yohimbine, the methyl ester of yohimbic acid, possesses a free hydroxyl group which may serve as the necessary chemical functionality for binding to a chemical modifier or spacer group. Yohimbic acid, which contains both a free hydroxyl group and a carboxy group as potential chemical functionalities, is also a preferred pharmaceutical agent.

Morphine (7,8-didehydro-4,5-epoxy-17-methyl-(5a,6a)-morphinan-3,6-diol sulfate (2:1), pentahydrate) is the most important alkaloid of opium. Morphine exerts its primary effect on the central nervous systems and organs containing smooth muscle. Morphine, as other opiods, acts as an agonist interacting with stereospecific and saturable binding sites/receptors in the brain, spinal cord and other tissues.

The central nervous system effects of intravenously administered morphine sulfate are influenced by its ability to cross the blood-brain barrier. The delay in the onset of analgesia following epidural or intrathecal injection may be attributed to its relatively poor lipid solubility (i.e., an oil/water partition coefficient of 1.42) and its slow access to the receptor sites. The hydrophilic character of morphine may also explains its retention in the central nervous system and its slow release into the systemic circulation. By altering morphine's lipid solubility and/or hydrophilic character through coupling with chemical modifier(s) according to the methods of the present invention, the bioavailability and bioactivity morphine can be modified. More specifically, the introduction of a charged chemical modifier should effectively prevent morphine from crossing the blood-brain barrier. Thus, the morphine-chemical modifier complex should serve as a peripheral acting analog. Morphine possesses two hydroxyl groups which can be coupled to chemical modifiers.

Methotrexate (formerly Amethopterin, N-[4-[[(2,4-diamino-6-pteridinyl)-methyl]methylamino]benzoyl]-L-glutamic acid) is an antimetabolite used in the treatment of certain neoplastic diseases, severe psoriasis, and adult rheumatoid arthritis. Methotrexate inhibits dihydrofolic acid reductase and therefore interferes with DNA synthesis, repair, and cellular replication. Methotrexate possesses several chemical functionalities, including carboxy groups and amino groups, which can be bound to chemical modifiers according to the present invention.

Lorazepam (7-chloro-5-(o-chlorophenyl)-1,3-dihydro-3-hydroxy-2H-1,4-benzodiazepin-2-one) is a benzodiazepine with antianxiety and sedative effects. The mean half-life for lorazepam is about 16 hours when given intravenously or intramuscularly. Lorazepam is rapidly conjugated at the 3-hydroxyl group into its major metabolite, lorazepam glucuronide, which is excreted in the urine. This metabolite has no demonstrable central nervous system activity in animals. Lorazepam possesses a free hydroxyl group and an amino group which can be derivatized according to the methods described herein.

6-Mercaptopurine (1,7-dihydro-6H-purine-6-thione monohydrate) is one of large series of purine analogues which interfere with nucleic acid biosynthesis and has been found active against human leukemias. See, e.g., Hitchings and Elion (1954) *Ann. NY Acad. Sci.* 60:195–199. Clinical studies have shown that the absorption of an oral dose of mercaptopurine in man is incomplete and variable averaging approximately 50% of the administered dose. 6-Mercaptopurine contains a free mercapto group and an amino group for bonding to chemical modifiers.

5-Fluorouracil is another preferred pharmaceutical agent. 5-Fluorouracil (5-fluoro-2,4 (1H,3H)-pyrimidinedione) is an antineoplastic antimetabolite. There is evidence that the metabolism of fluorouracil in the anabolic pathway blocks the methylation reaction of deoxyuridylic acid to thymidylic acid. In this manner, fluorouracil interferes with the synthesis of DNA and to a lesser extent inhibits the formation of RNA. Fluorouracil distributes into tumors, intestinal mucosa, bone marrow, liver, and other tissues throughout the body. In spite of its limited lipid solubility, fluorouracil diffuses readily across the blood-brain barrier. Fluorouracil is effective in the palliative management of carcinoma of the colon, rectum, breast, stomach, and pancreas. Fluorouracil possesses two amino groups which can bond to chemical modifiers according to the present invention.

Another preferred heterocyclic drug is theophylline, a xanthine bronchodilator, pulmonary vasodilator, and smooth muscle relaxant. Theophylline is used for the symptomatic relief and/or prevention of asthma and the reversible bronchospasm associated with chronic bronchitis and emphysema. Theophylline possesses an amino functionality for coupling with a chemical modifier.

Nalidixic acid is also a heterocyclic drug which can be delivered using the methods described herein. Nalidixic acid is an antibacterial agent with activity against gram negative bacteria and is rapidly absorbed from the gastrointestinal tract. Nalidixic acid possesses an amino group, a keto group, and a carboxy group as chemical functionality.

Melatonin, a tryptamine derivative, is a hormone of the pineal gland and is also produced by extrapineal tissues. melatonin has been postulated as the mediator of photic-induced antigonadotrophic activity in photoperiodic mammals. Melatonin has been used in the treatment of psychiatric disorders. Melatonin possesses amino functionality for coupling with chemical modifiers.

Nicotinic acid or niacin functions in the body as a component of two hydrogen transporting coenzymes. In addition to its functions as a vitamin, nicotinic acid exerts several distinctive pharmacological effects which vary according to the dosage level employed. Nicotinic acid, in large doses, causes a reduction in serum lipids. Nicotinic acid is a nitrogen heterocycle having a hydroxyl group.

B. The Chemical Modifier i. General

The chemical modifier is preferably susceptible to in vivo cleavage from the pharmaceutical agent-chemical modifier complex, such that the agent is in an active form and the modifier becomes a non-toxic compound or is rapidly degraded. Preferably, the modifier will be a naturally occurring substance. In certain instances, the modifier is a biologically-active molecule or a second pharmaceutical agent.

Chemical modifiers, according to the present invention, comprise either permanently charged organic compounds or organic compounds which carry an ionic charge by virtue of the conditions of pH which exist during transmembrane or transdermal delivery. According to some embodiments, the net ionic charge of a chemical modifier (e.g., chemical modifiers comprising proteins or peptides) can be either increased or decreased by varying the conditions of pH during delivery.

Although chemical modifiers function primarily to alter the charge characteristics of a pharmaceutical agent (e.g., by the addition, deletion, or redistribution of charge), they also can serve to modify the solubility parameters of the pharmaceutical agent. For example, more than one chemical modifiers can be coupled to a charged pharmaceutical agent to produce a complex having the same net charge as the pharmaceutical agent, but exhibiting different water or lipid solubility due to the introduction of the additional hydrophilic or lipophilic groups of the chemical modifiers.

Chemical modifiers possess at least one chemical functionality which can be covalently bonded to a pharmaceutical agent, optionally via a spacer group. Examples of chemical functionality include hydroxy, carboxy, amino, ketone, mercapto, sulfonamide, amide groups and the like.

ii. Positively Charged Chemical Modifiers

In a preferred embodiment, the chemical modifier carries a positive charge. The positive charge typically arises by virtue of covalent bonds, such as in a quaternary ammonium group. According to one aspect of this embodiment, the charged complex is prepared by the covalent attachment of an uncharged moiety in such a manner as to generate a charge. The complex can be dissociated under physiological conditions. For example, an a-haloalkyl carbonates or esters can be reacted with a pharmaceutical agent having a tertiary amino group to provide a pharmaceutical agent-chemical modifier complex having a quaternary ammonium group. Chemical or enzymatic hydrolysis of the carbonate or ester bond is followed by spontaneous elimination of the alkyl aldehyde and regeneration of the active pharmaceutical agent.

This general method for enhancing the delivery and transport of pharmaceutical agents can be utilized with a variety of pharmaceutical agents having tertiary amine groups. In a preferred embodiment, the pharmaceutical agent comprises deprenyl, as illustrated below:

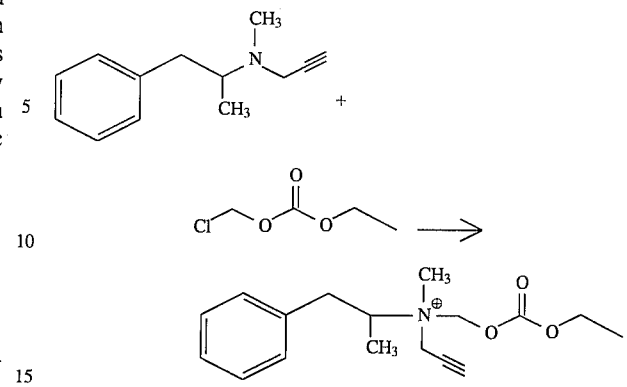

In another embodiment, the chemical modifier acquires a positive charge only after the modifier is complexed with the pharmaceutical agent. For example, the pharmaceutical agent-chemical modifier complex may obtain a positive charge via protonation in the delivery buffer or formulation due to the pH conditions which exist during drug delivery.

iii. Examples of Chemical Modifiers

An example of a chemical modifier containing a quaternary ammonium group is choline (2-hydroxy-N,N,N-trimethylethanaminium, available from Aldrich Chemical Co., Milwaukee, Wis.). Choline carries a positive charge and possesses a hydroxyl group as a chemical functionality. The hydroxyl group may be utilized, for example, to form ester or carbonate linkages with carboxy or hydroxyl groups, respectively, of pharmaceutical agents or to form carbamates with amine groups of pharmaceutical agents. Homologs of choline, such as 3-hydroxy-N,N,N-trimethylpropaminium chloride, may also serve as chemical modifiers. These homologs of choline differ from choline in the number of carbon atoms. Like choline, homologs of choline possess both a hydroxyl group and an amino group as chemical functionality.

Additional preferred chemical modifiers are carnitine and its homologs. Carnitine (3-carboxy-2-hydroxy-N,N,N-trimethyl-1-propanaminium hydroxide, inner salt, available from Aldrich Chemical Co.) is a nontoxic, naturally occurring amino acid. See Fix et al. (1986) *Am. J. Physiology* 251:G332–G340. As in the case of choline, the N,N,N-trimethylammonium group of carnitine serves to impart a positive charge to the molecule.

Carnitine possesses two types of chemical functionality with which it can bond to a pharmaceutical agent. For example, the hydroxyl of carnitine may be reacted with a carboxy group of a pharmaceutical agent. Alternatively, the carboxy group of carnitine may be utilized to form, for example, either ester, thioester, or amide linkages with hydroxy, mercapto, or amino groups of a pharmaceutical agent.

Homologs of carnitine, such as 4,4-dimethylamino-3hydroxybutyric acid or 6,6-dimethylamino-3-hydroxyhexanoic acid, may also serve as chemical modifiers. The dimethylamino group of these chemical modifiers can be alkylated to form a quaternary ammonium salt either before or after the chemical modifier is coupled to a pharmaceutical agent. These homologs of carnitine differ from carnitine in their number of carbon atoms. Like carnitine, homologs of carnitine possess both a hydroxyl group and a carboxy group with which they can form bonds to pharmaceutical agents.

Oligomers of carnitine (polyesters) may also be employed as chemical modifiers. The molecular weight of the oligomer is usually between 100–2000. Typically 2 to 10 carnitine molecules are used to construct the polyester.

A further carnitine derivative which may function as a chemical modifier is thiocarnitine. Thiocarnitine is the mercapto analog to carnitine and thus, possesses a mercapto group and a carboxylic acid group as chemical functionality.

Lysine (2,6-diaminohexanoic acid, available from Aldrich Chemical Co.) and particularly its $N^\epsilon$-methylated homologs, especially $N^\epsilon$-trimethyllysine, may also be used as chemical modifiers. Hereinafter, lysine shall be understood to refer to lysine and to its $N^\epsilon$-methylated homologs, including $N^\epsilon$-trimethyllysine and its $\partial$-hydroxyl derivative. As in the case of carnitine, lysine possesses two functionalities with which it can bind to a pharmaceutical agent. Specifically, either the amino or carboxy groups of lysine may be exploited to form linkages with pharmaceutical agents. The amino group, for example, may be converted to an amide through reaction with a carboxy group of the pharmaceutical agent or to a carbamate by reaction with the chloroformate derivative of a hydroxy-containing pharmaceutical agent. Alternatively, the carboxy group of lysine may be transformed into either an ester, thioester or amide through reaction with a hydroxy, mercapto, or amino group of a pharmaceutical agent. In addition, derivatives of lysine may be used as chemical modifiers. In a preferred embodiment, the $\partial$-hydroxyl derivative which provides a third functionality for selective modification may be used as a chemical modifier.

In a preferred embodiment, the chemical modifier exhibits therapeutic effects apart from its carrier function. An example of a therapeutic chemical modifier is oligomeric or polymeric lysine (polylysine). Polylysine possesses antiviral and antibacterial activities, as well as a specific affinity for tumor cells in cancerous tissue. Ryser, H. J.-P. and Shen, W.-C. (1986) in "Targeting of Drugs with Synthetic Systems," G. Gregoriadis, J. Senior and G. Poste, Eds., pp. 103–121, Plenum Publishing Corp. New York. Polylysine has also been shown to enhance the uptake into cells of conjugated proteins such as albumin and peroxidase. Shen, W.-C. and Ryser, H. J.-P, (1978) *Proc. Natl. Acad. Sci. USA* 75:1872–1876. An additional desirable chemotherapeutic property of poly(L-lysine) is its facile degradation by intercellular trypsin. Polylysine contains amino and carboxy groups. Typically, 2 to 10 lysines are used to form the polyamide. The molecular weight of the oligomer is usually between 200–2000. The polymerization of lysine may be accomplished by methods well known by those skilled in the art.

In addition, polylysine derivatives containing specific protease cleavage sites may serve as chemical modifiers. An example of such a derivative is $(Lys)_n$-Phe-Pro-Arg, where "$Lys_n$" represents polylysine; "Phe" refers to phenylalanine; "Pro" refers to proline, and "Arg" refers to arginine. This polylysine derivative may be cleaved by the serine proteinase thrombin.

Other amino acids such as ornithine (2,5-diaminopentanoic acid, available from Aldrich Chemical Co.) and its $N^\partial$-methylated homologs, serine, threonine, and tyrosine may also be used as chemical modifiers in an analogous manner. In addition, folate or folic acid (N-[4-[[2(2- amino-1,4-dihydro -4-oxo-6-pteridinyl)methyl]amino]benzoyl]-L-glutamic acid) possesses amino and carboxy groups which can be coupled to pharmaceutical agents and/or derivatized to introduce positive charge. Folate is internalized by cells by receptor-mediated endocytosis and it has been reported that covalently conjugating folic acid to a macromolecule, such as BSA, bovine IgG, bovine RNase, and horseradish peroxidase, allows for the delivery of the conjugates into many living cells by the cellular uptake system for folate. See Leamon and Low (1991) *Proc. Natl. Acad. Sci. USA* 88:5572–5576 and Anderson et al. (1992) *Science* 255:410–411.

Another example of a chemical modifier is betaine (1-carboxy-N,N,N-trimethylmethanaminium hydroxide inner salt, available from Aldrich Chemical Co.). Betaine possess a carboxylic acid as chemical functionality and carries a permanent positive charge from the quaternary ammonium group. Homologs of betaine such as N,N,N-trimethyl-4-aminobutyric acid may also serve as chemical modifiers.

Other preferred chemical modifiers include betonicine (trans-2-carboxy-4-hydroxy-1,1-dimethylpyrrolidinium hydroxide, inner salt), stachydrine (2-carboxy-1,1-dimethylpyrrolidinium hyroxide inner salt), and trigonelline (3-carboxy-1-methylpyridinium hyroxide inner salt). Each of these compounds possesses a quaternary ammonium group, as well as chemical functionality capable of coupling to pharmaceutical agents.

Further examples of chemical modifiers include histones. Several classes of these highly conserved proteins exist. The smallest histone is H4 with 103 amino acids and a net charge of approximately +18 at neutral pH. The largest histone H1 carries a charge of approximately +46 at neutral pH over approximately 207 residues. Histone H1 is rich in lysine groups. These lysine groups contain amino groups which may be used to bind to pharmaceutical agents or spacer groups. Histones H2A and H2B also contain lysine groups, and thus, amino groups as chemical functionality. Histones H3 and H4 are rich in arginine. The arginine residue provides an amino group which may be bonded to spacer groups or pharmaceutical agents. Moreover, one variant of the histone H3 contains a free cysteine residue that may be used to couple with spacer groups or pharmaceutical agents. Similarly the protamines are a group of proteins that contain basic amino acids and can serve as chemical modifiers.

Anther lysine rich protein which can be employed as chemical modifiers according to the methods described herein is cytochrome c, a heme protein in which the active prosthetic group is a derivative of iron protoporphyrin IX. Cytochrome c occurs in the cells of all aerobic organisms and can be found in animal cells in the mitochondrial protein-lipid complex. See Margoliash and Schejter (1966) *Advan. Protein Chem.* 21:113, Structure and Function of Cytochromes, Okunuki et al. (eds.), University Park Press: Baltimore (1968). Cytochrome c can be iontophoretically transported readily across human or mouse skin. See (1993) "Electrotransport: A Technology whose Time Has Come".

Other lysine rich proteins; proteins that complex metal ions, and particularly iron, such as siderophores, enterobactin, HBED (N,N'-bis(2-hydroxybenzyl)ethylenediamine-N, N'-diacetic acid), and ferrioxamines (see, e.g., Kirk-Othmer Encyclopedia of Chemical Technology, 3rd Ed., Vol. 13, pages 782–786); proteins with covalently attached heme or porphyrin groups; and other compounds covalently attached to heme or porphyrin groups will also find use as chemical modifiers in the methods described herein.

Aminosteroids also can be employed as chemical modifiers. For example, squalamine, an antimicrobial about as potent as ampicillin, possesses three quaternary ammonium groups, a sulfate group, as well as a hydroxyl group. Moreover, the mechanism of squalamine's activity may at least partially be due to a disruption of the lipid bilayer in membranes. Thus, squalamine could serve as a penetration enhancer, as well as a chemical modifier and/or a pharmaceutical agent.

In addition, the naturally occurring plant steroid, chonemorphine ((3β,5α,20S)-$N^{20}$,$N^{20}$-dimethylpregnane-3,2-diamine) possesses two amino groups, one of which can be derivatized to produce the corresponding ammonium salt, while the other can be coupled to a pharmaceutical agent. See Janot et al. (1962) *Bull. Soc. Chim. France* 111; and Chien et al. (1965) *J. Org. Chem.* 29:315. Likewise, conessine (3β-(dimethylamino)con-5-enine) is a naturally occurring plant steroid having two amino groups and can find use as a chemical modifier according to the methods described herein.

iv. Negatively Charged Chemical Modifiers

In another embodiment of the present invention, chemical modifiers carry negative charges. The negative charge typically arises from a sulfate group, a phosphate group, or a carboxy group. The sulfate and carboxy groups will provide a single negative charge, whereas the phosphate group may impart either a single or double negative charge.

Naturally occurring, multi-functional aminosulfonic acids, including taurine and cysteic acid, can also serve as negatively charged modifiers. Taurine is a particularly versatile chemical modifier in that it can provide either a negative or positive charge. Taurine (2-aminoethanesulfonic acid, available from Aldrich Chemical Co.) acquires a negative charge by deprotonation of its sulfonic acid group to form the corresponding sulfonate salt. Taurine also possesses an amino group as chemical functionality. This amino group may be converted to the corresponding ammonium salt to provide a positive charge. Similarly, cysteic acid (3-sulfoalanine, available from Aldrich Chemical Co.) which possesses both amino and carboxy functionalities in addition to the sulfonic acid group, may provide either positive or negative charge.

In addition, sulfate salts may be produced through the reaction of a hydroxyl containing compound with sulfur trioxide and its amine and ether adducts, chlorosulfonic acid, sulfonic acid, or sulfuric acid. See, e.g., Barton and Ollis, *Comprehensive Organic Chemistry*, Pergamon Press, New York (1979).

Phosphates may be produced through the reaction of a hydroxyl containing pharmaceutical agent, chemical modifier or spacer group with phosphonyl halides, orthophosphoric acid, or phosphorus pentoxide. See, e.g., Barton and Ollis, *Comprehensive Organic Chemistry*.

Preferred examples of negatively charged pharmaceutical agent-modifier complexes include digitoxigenin-3-sulfate, triethylammonium salt; digitoxin-4'''-sulfate, triethylammonium salt; and the like.

v. Nucleotide-based Chemical Modifiers

One aspect of this invention contemplates the covalent binding of nucleotide-based chemical modifiers to pharmaceutical agents. Nucleotides are phosphate esters of glycosides of heterocyclic bases and are the structural units of both oligonucleotides and nucleic acids. Each phosphate functionality found in a nucleotide, oligonucleotide, or nucleic acid potentially is capable of imparting a negative charge to the molecule.

Typically, a hydroxyl group of a sugar residue, an amino group from a base residue, or a phosphate oxygen of the nucleotide will be utilized as the needed chemical functionality to couple the nucleotide-based chemical modifier to the pharmaceutical agent. However, one of skill in the art will readily appreciate that chemical modifiers with other chemical functionalities can be prepared by conventional techniques. For example, the hydroxyl group of the sugar residue can be converted to a mercapto or amino group using techniques well known in the art. In a preferred embodiment, the chemical modifier exhibits therapeutic effects apart from its carrier function and comprises an antisense compound or triple helix drug.

Typically, the nucleotide-based chemical modifier will be covalently coupled to the pharmaceutical agent via a spacer group. An illustrative embodiment calls for the use of the spacer group 3-maleimidobenzoic acid, as shown below. See, generally, Tung et al. (1991) *Bioconj. Chem.* 2:464. The 5'-terminal phosphate group of the oligonucleotide is modified to produce the corresponding aminoalkyl phosphate ester. The spacer group, 3-maleimidobenzoic acid, is then introduced via reaction of the amino group of the phosphate ester with 3-maleimidobenzoic acid N-hydroxysuccinimide ester. Pharmaceutical agents containing a mercapto group or a hydroxyl group can be covalently coupled to the spacer group through this functionality.

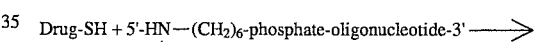

Drug-SH + 5'-HN—$(CH_2)_6$-phosphate-oligonucleotide-3' ⟶

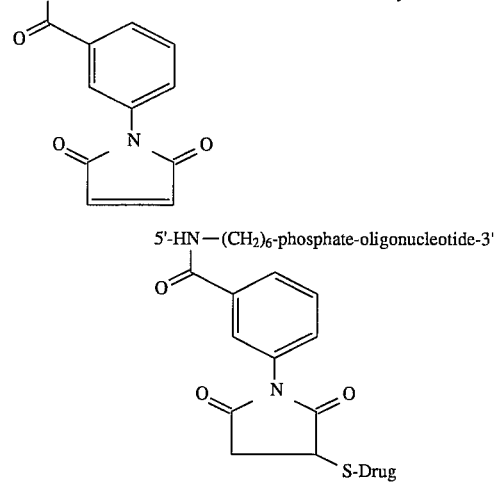

This coupling motif is particularly preferred for peptide and protein drugs containing cysteine residues which can be coupled to the spacer group through the mercapto functionality of the cysteine residue. See, e.g., Tung et al. (1991) *Bioconj. Chem.* 2:464.

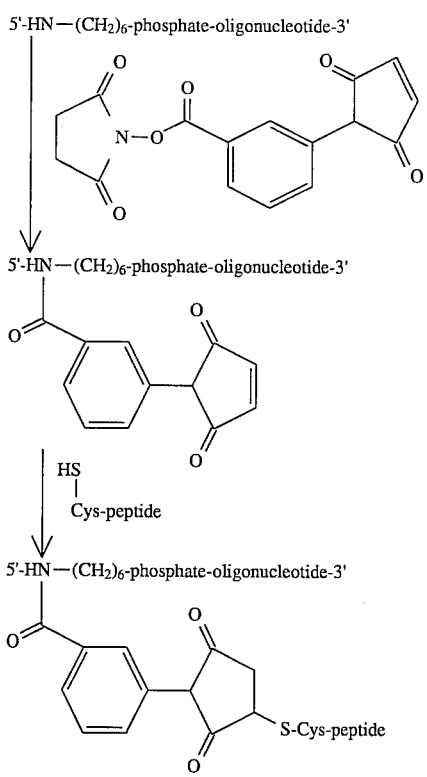

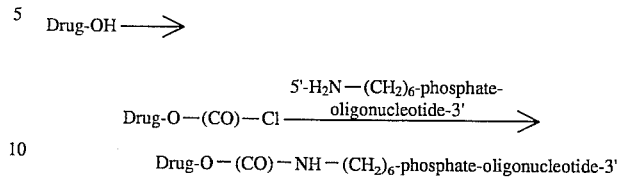

Alternatively, the 5'-terminal phosphate group of the oligonucleotide is modified to produce the corresponding mercaptoalkyl phosphate ester, as shown below. The mercapto group can be coupled directly to another mercapto group of a pharmaceutical agent (e.g., a mercapto group from a cysteine residue in a protein/peptide drug) via a disulfide linkage or the mercapto group can be coupled to a spacer group, such as 3-maleimidobenzoic acid, which has been previously been linked to a pharmaceutical agent (e.g., via a hydroxy, mercapto, or amino group of the pharmaceutical agent). See, generally, Eritja et al. (1991) Tetrahedron 4113.

Aminoalkyl phosphate derivatives of nucleotide-based chemical modifiers also can be covalently coupled to pharmaceutical agents containing carboxy groups or hydroxyl groups.

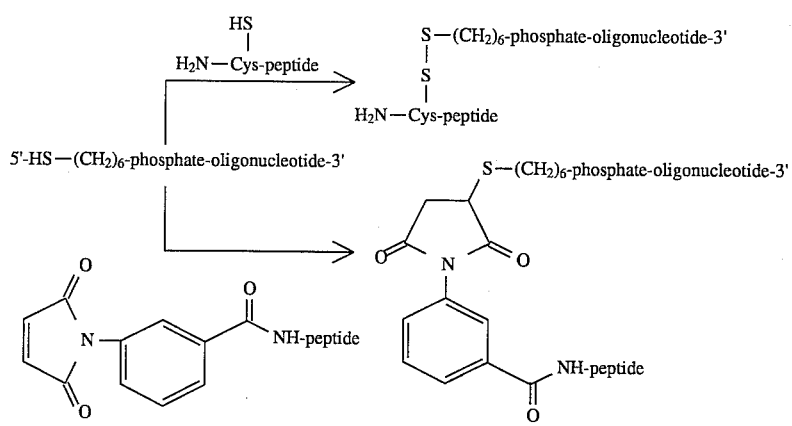

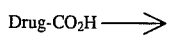

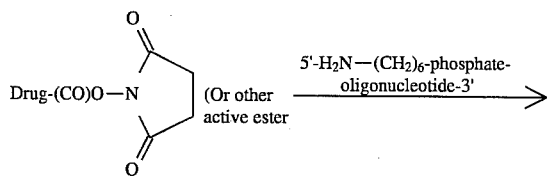

Typically, the chemical functionality of the pharmaceutical agent is activated prior to coupling with the chemical modifier (e.g., an activated ester is produced from the carboxy group or a chloroformate is formed from the hydroxyl group) as shown below.

Again, typically, the chemical functionality of the pharmaceutical agent is activated prior to coupling with the chemical modifier (e.g., an activated ester is produced from the carboxy group or a chloroformate is formed from the hydroxyl group) as shown below.

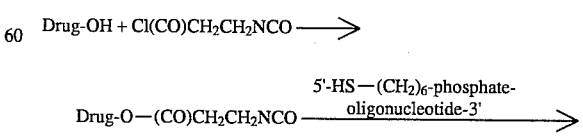

The use of a phosphate-based spacer is shown below. See, generally, Juby et al. (1991) *Tetrahedron Letters* 32:879. An orthogonally protected substrate-bound phosphate group is employed as the precursor to the spacer.

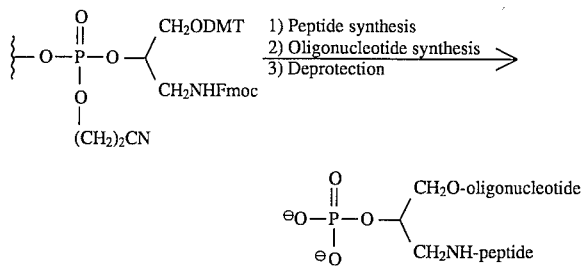

One protecting group of the precursor is removed to yield a reactive group that can be exploited for synthesis of the peptide/protein drug. The second protecting group is then removed to allow for oligonucleotide synthesis. Cleavage from the substrate yields a pharmaceutical agent-nucleotide-based chemical modifier complex wherein the pharmaceutical agent is a peptide/protein drug and the spacer comprises a negatively charged phosphate group. Similarly, a pharmaceutical agent-chemical modifier complex can be produced wherein the pharmaceutical agent is a nucleotide-based drug.

The most commonly used in vitro DNA amplification method is PCR. Alternate amplification methods include, for example, nucleic acid sequence-based amplification (Comptom (1991) *Nature* 350:91–92) and amplified antisense RNA (Van Gelder et al. (1988) *Proc. Natl. Acad. Sci. USA* 85:7652–7656), and the self-sustained sequence replication system (3SR) (Guatelli et al. (1990) *Proc. Natl. Acad. Sci. USA* 87:1874–1878).

vi. Screening Procedures

The optimal chemical modifier component for covalently binding to a given pharmaceutical agent can be identified using a variety of screening techniques, including the screening procedures set forth in copending application Ser. Nos. 07/762,522, 07/946,239, 07/778,223, 07/876,288, 07/946,239, and 07/963,321, Fodor et al. (1991) *Science* 251:767–773, PCT publication No. WO 92/10092, and PCT publication No. 92/05285, 92/12842, 92/12843, 91/19813, 91/17271, 91/19818, and 90/15070, each of which is expressly incorporated herein by reference.

Although a library of covalently linked pharmaceutical agent-chemical modifier complexes can be produced, generally a library comprising chemical modifiers will first be synthesized to screen for transport activity. Typically, this library will be synthesized in a solid-state format with each modifier bound to a substrate via a cleavable linker. The compound can then be cleaved from the substrate and screened in vitro as to their transport or other characteristics. Of course, depending on the property being analyzed, the screening can also be performed while the compounds are bound to the solid substrate.

The optimal modifiers can be amplified, for example, in the case of nucleotide-based chemical modifiers, by PCR or other means well known to those skilled in the art, to provide sufficient chemical modifier to be accurately sequenced. Once the optimal chemical modifier is identified, the screening procedure can be repeated to further optimize the composition of the pharmaceutical agent.

Typically, the chemical modifier array will be bound to a solid substrate. This format allows for the rapid and efficient synthesis and screening of the modifiers. In accordance with the present invention, solid phase substrates include synthesis resins (see, e.g., Merrifield (1963) *J. Am. Chem. Soc.* 85:2149–54; U.S. patent application Ser. No. 07/762,522, filed Sep. 18, 1991, U.S. patent application Ser. No. 946,239, filed Sep. 16, 1991; U.S. patent application Ser. No. 07/876, 792, filed Apr. 29, 1992; and Houghten, U.S. Pat. No. 4,631,211), rods (see, e.g., Geysen et al. (1984) *Proc. Natl. Acad. Sci. USA* 81:3998–4002 and Geysen et al. (1986) PCT publication No. WO 86/00991), glass slides (see Fodor et al., U.S. Pat. No. 5,143,854), and any additional support upon which oligonucleotides, peptides, or other organic compounds can be synthesized. Thus, the solid substrate can be composed of any of a wide variety of materials, for example, polymers, plastics, resins, polysaccharides, silicon or silica-based materials, carbon, metals, inorganic glasses, and membranes.

Generally, conventional polymer synthesis techniques can be utilized to produce the chemical modifier collections. These polymer synthesis techniques generally are based on the sequential addition of monomer units or building blocks. This assembling of oligomers from many types of subunits requires using the appropriate coupling chemistry for a given set of monomer units or building blocks. Any set of building blocks that can be attached to one another in a step-by-step fashion can serve as the monomer set. The attachment can be mediated by chemical, enzymatic, or other means, or by a combination of these. The resulting chemical modifiers can be linear, cyclic, branched, or assume various other conformations as will be apparent to those skilled in the art.

Techniques for the solid state synthesis of oligonucleotides are described, for example, in *Oligonucleotide Synthesis: A Practical Approach*, (ed. M. J. Gait) IRL Press at Oxford University Press (1990). Other techniques include those of U.S. Pat. No. 5,143,854, U.S. Pat. No. 5,164,491, and copending application Ser. No. 07/978,944. Techniques for solid state synthesis of polypeptides are described, for example, in Solid Phase Peptide Synthesis: A Practical Approach, (eds. E. Atherton and R. C. Sheppard) IRL Press at Oxford University Press (1989) and in Merrifield, *J. Amer. Chem. Soc.* 85:2149–2156 (1963). Peptide coupling chemistry is also described in *The Peptides*, Vol. 1, (eds. Gross, E., and J. Meienhofer), Academic Press, Orlando (1979), which is incorporated herein by reference). Other techniques include those of Geysen et al., *J. Imm. Meth.*, (1987) 102:259–274; Houghten et al., *Nature* (1991)354:84–86.Procedures for the synthesis of cyclic oligomers and substrate-bound oligomers with reversed polarity can be found in copending application Ser. No. 07/978, 940. Substrate-bound oligomer collections having a random monomer composition can be produced using the techniques described in copending application Ser. No. 07/946,239. In some embodiments, advanced techniques for synthesizing polymer arrays are utilized such as those described in copending application Ser. No. 07/796,243, or light-directed, spatially-addressable techniques disclosed in Pirrung et al., U.S. Pat. No. 5,143,854, such techniques being referred to herein for purposes of brevity as VLSIPS™ (Very Large Scale Immobilized Polymer Synthesis) techniques.

Some embodiments will exploit a soluble array of chemical modifiers or pharmaceutical agent-chemical modifier complexes. These soluble collections can be prepared directly or, in some embodiments, a solid support is used to synthesize a library or array of chemical modifiers or complexes of diverse length and composition. The members of the library are cleaved from the support prior to use.

C. Methods of Activation

Generally, prior to forming the linkage between the chemical modifier, the pharmaceutical agent and optionally, the spacer group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the chemical modifier or pharmaceutical agent can be activated through treatment with phosgene to form the corresponding chloroformate. In addition, if the hydroxyl functionality is part of a sugar residue, then the hydroxyl group can be activated through reaction with di-(n-butyl)tin oxide to form a tin complex.

Carboxy groups may be activated by conversion to the corresponding acyl halide. This reaction may be performed under a variety of conditions as illustrated in March, supra pp. 388–89. In a preferred embodiment, the acyl halide is prepared through the reaction of the carboxy containing group with oxalyl chloride.

D. Methods of Linking

Typically, the pharmaceutical agent is linked covalently to a chemical modifier using standard chemical techniques through their respective chemical functionalities. Optionally, the chemical modifier or pharmaceutical agent can be coupled to the pharmaceutical agent through one or more spacer groups. The spacer groups can be equivalent or different when used in combination. Likewise, if more than one chemical modifier is used to produce the pharmaceutical agent-chemical modifier complex, then the chemical modifiers can be equivalent or different.

The pharmaceutical agent-modifier complex is prepared by linking a pharmaceutical agent to a chemical modifier (or optionally to a spacer group which has been or will be attached to a chemical modifier) via their respective chemical functionalities. Preferably, the pharmaceutical agent (e.g., chemical functionality 1) is joined to the chemical modifier, optionally via a spacer group, (e.g., chemical functionality 2) via the linkages shown in Table 3. Those of skill in the art will recognize that one can first attach the spacer either to the chemical modifier or to the pharmaceutical agent. The chemical functionalities shown in Table 3 can be present on the pharmaceutical agent, spacer, or chemical modifier, depending on the synthesis scheme employed.

TABLE 3

| Chemical Functionality 1 | Chemical Functionality 2 | Linkage |
| --- | --- | --- |
| Hydroxy | Carboxy | Ester |
|  | Hydroxy | Carbonate |
|  | Amine | Carbamate |
|  | SO₃ | Sulfate |
|  |  | Phosphate |
|  | Carboxy | Acyloxyalkyl ether |
|  | Ketone | Ketal |
|  | Aldehyde | Acetal |
|  | Hydroxy | Anhydride |
| Mercapto | Mercapto | Disulfide |
|  | Carboxy | Acyloxyalkyl thioether |
|  | Carboxy | Thioester |
| Carboxy | Amino | Amide |
|  | Mercapto | Thioester |
|  | Carboxy | Acyloxyalkyl ester |
|  | Carboxy | Acyloxyalkyl amide |
| Amino |  | Acyloxyalkoxy |

TABLE 3-continued

| Chemical Functionality 1 | Chemical Functionality 2 | Linkage |
| --- | --- | --- |
|  |  | carbonyl |
|  | Carboxy | Anhydride |
|  | Carboxy | N-acylamide |
|  | Hydroxy | Ester |
|  | Hydroxy | Hydroxymethyl ketone ester |
|  | Hydroxy | Alkoxycarbonyl oxyalkyl |
| Amino | Carboxy | Acyloxyalkyl amine |
|  | Carboxy | Acyloxyalkyl amide |
|  | Amino | Urea |
|  | Carboxy | Amide |
|  | Carboxy | Acyloxyalkoxy carbonyl |
|  | Amide | N-Mannich base |
|  | Carboxy | Acyloxyalkyl carbamate |
| Phosphate oxygen | Hydroxy | Phosphate ester |
|  | Amine | Phosphoramidate |
|  | Mercapto | Thiophosphate ester |
| Ketone | Carboxy | Enol ester |
| Sulfonamide | Carboxy | Acyloxyalkyl sulfonamide |
|  | Ester | N-sulfonylimidate |

One skilled in the art will readily appreciate that many of these linkages may be produced in a variety of ways and using a variety of conditions. For the preparation of esters, see, e.g., March supra at 1157; for thioesters, see March, supra at 362–363, 491, 720–722, 829, 941, and 1172; for carbonates, see March, supra at 346–347; for carbamates, see March, supra at 1156–57; for amides, see March supra at 1152; for ureas and thioureas, see March supra at 1174; for acetals and ketals, see Greene et al. supra 178–210 and March supra at 1146; for acyloxyalkyl derivatives, see *Prodrugs: Topical and Ocular Drug Delivery*, K. B. Sloan, ed., Marcel Dekker, Inc., New York, 1992; for enol esters, see March supra at 1160; for N-sulfonylimidates, see Bundgaard et al., (1988) *J. Med. Chem.*, 31:2066; for anhydrides, see March supra at 355–56, 636–37, 990–91, and 1154; for N-acylamides, see March supra at 379; for N-Mannich bases, see March supra at 800–02, and 828; for hydroxymethyl ketone esters, see Petracek et al. (1987) *Annals NY Acad. Sci.*, 507:353–54; for disulfides, see March supra at 1160; and for phosphonate esters and phosphonamidates, see, e.g., copending application Ser. No. 07/943,805, which is expressly incorporated herein by reference.

A variety of ketal type linkages may be produced. Ketal type linkages that may be produced in the pharmaceutical agent-chemical modifier complexes of the present invention include, but are not limited to, imidazolidin-4-ones, see *Prodrugs*, supra; oxazolin-5-ones, see Greene et al. supra at 358; dioxolan-4-one, see Schwenker et al. (1991) *Arch. Pharm.* (Weinheim) 324:439; spirothiazolidines, see Bodor et al. (1982) *Int. J. Pharm.*, 10:307 and Greene et al. supra at 219 and 292; and oxazolidines, see March supra at 87 and Greene et al. supra at 217–218 and 266–267.

The processes for constructing or modifying nucleotides or nucleic acids are generally well known in the art. These processes are described in the patent and other literature. See, for example, U.S. Pat. Nos. 4,431,739 and 5,013,653. Additionally, nucleic acid construction principles can be exploited using various restriction enzymes which make sequence specific cuts in the nucleic acid to produce blunt ends or cohesive ends, DNA ligases, enzymatic addition of single-stranded ends to blunt-ended DNA, and construction of synthetic DNAs by assembly of short oligonucleotides.

A preferred linkage for peptide and protein pharmaceutical agents may be formed by the reaction of an aldehyde containing chemical modifier or spacer group with the terminal amino acid of the pharmaceutical agent. This cyclic derivative serves to stabilize the pharmaceutical agent towards enzymatic action, yet is easily hydrolyzed to release the peptide drug. This linkage is shown below wherein $R_1$, $R_2$, and $R_3$ are independently hydrogen, alkyl, arylalkyl, aryl, and heteroaryl. H. Bundgaard (1991) *Drugs of the Future*, 16(5):443–458.

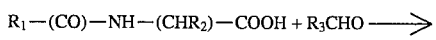

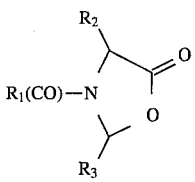

Preferred examples of pharmaceutical agent-chemical modifier complexes linked via an ester include: 3α-hydroxy-5α-pregnan-20-one 3α-(O-palmityl)-L-carnitine ester; 3β-hydroxy-5α-pregnan-20-one 3β-(O-acetyl)-L-carnitine ester; 3a-hydroxy-5a-pregnan-20-one 3a-(O-acetyl)-L-carnitine ester; 3β-hydroxy-5a-pregnan-20-one 3β-(O-acetyl)-D,L-carnitine ester; digitoxigenin-3-(O-acetyl-D,L-carnitine) ester, chloride salt; digitoxigenin-3-(O-acetyl-L-carnitine) ester, chloride salt; digitoxigenin-3-(O-palmityl-L-carnitine) ester, chloride salt; 2-(4-nitrophenyl)ethanol O-acetyl-L-carnitine ester, chloride salt; 17 β-estradiol-17β-(O-acetyl-L-carnitine) ester; O-(indomethacinyl)-(D,L)-norcarnitine, methyl ester; O-(indomethacinyl)norcholine; (indomethacinyl)choline iodide; O-indomethacinyl-(D,L-carnitine methyl ester), iodide salt; O-indomethacinyl-(L-carnitine hydrochloride); indomethacin 2-(N-(1-butyl)-N,N-dimethylaminoethyl ester, bromide salt; 3,17β-estradiol-17β-betaine ester, chloride salt; 5-fluorouracil-l-(4-trimethylaminobutyroyloxymethyl), chloride salt; 6-morphinyl sulphate-(4-N,N,N-trimethylammoniobutyrate) ester, and lorazepam-3-(O-acetylcarnitine) ester chloride salt.

A preferred example of a pharmaceutical agent-chemical modifier complex with a carbamate linkage is 17β-hydroxy-estra-1,3,5(10)-trien-3-yl 2-(N,N,N-trimethyl-amino)ethoxycarbonylmethyl carbamate, iodide salt.

Preferred examples of pharmaceutical agent-chemical modifier complexes with a carbonate linkage include: 3,17β-estradiol-3-choline carbonate, iodide salt; 3,17β-estradiol-17 β-choline carbonate, iodide salt; digitoxigenin-3-(O-choline chloride carbonate) ester; and digitoxin-4'''-(choline chloride) carbonate ester.

Preferred examples of pharmaceutical agent-chemical modifier complexes using a spacer group include: 3-hydroxy-estra-1,3,5(10)-trien-17 β-yl 2-(N,N,N-triethylamino)ethoxy-carbonylmethyl carbamate, iodide salt; indomethacin 2-[N-(6'-N',N'-dimethylamino)hexanamido]ethyl ester; indomethacin 2-[N-methyl-N-(6'-N',N'-dimethylamino)hexanamido]ethyl ester; indomethacin 2-[N-(6'-N',N',N'-trimethylamino)-hexanamido]ethyl ester, iodide salt; indomethacin 2-[N-methyl-N-(6'-N',N',N'-trimethylamino)hexanamido]ethyl ester, iodide salt; piroxicam-O-(6-aminocaproate) acetyl-L-carnitinamide; indomethacin 2-(N-(2-hydroxyethyl)-N,N-dimethyl) aminoethyl ester, bromide salt; 3-hydroxy-estra-1,3,5(10)-trien-17β-yl 6-(O-acetylcarnitinato )hexyl carbonate; digitoxin-4'''-6-[O-(acetylcarnitinamido)hexyl]carbonate ester; 3-hydroxy-estra-1,3,5,(10)-trien-17 β-yl 6-(O-acetyl-carnitinamido)hexyl carbonate; progesterone 3-{2O-[6-O-(O-acetylcarnitinyl)deca-noyl]-glycolic acid} enol ester; testosterone-17-betainoyloxymethylcarbonyloxymethyl carbonate, iodide salt; digoxin-12-{N-[6-(N',N',N'-trimethylamino)hexanoyloxymethyl]-glycinoyloxymethyl} carbonate-3''',4'''-cyclic carbonate, bromide salt; digoxin-4'''-4-(4-trimethylaminobutyroyloxy-)butyrate bromide salt; indomethacin 6-(O-acetyl-L-carnitinamido)hexanoyloxymethyl ester, chloride salt; digoxin-4'''-6-O-palmitoylcarnitinamido)hexyl carbonate, chloride salt; digoxin-12-[1-(6-betaionoyloxyhexyl)]carbonate-3''',4'''-cyclic carbonate, chloride salt; digoxin 12-(6-trimethylamino-hexanoyloxymethyl carbonate)-3''',4'''-cyclic carbonate, bromide salt; 6-mercaptopurine-S-[6-(N,N,N-trimethylamino)hexanoyl-oxymethyl], iodide salt; and digoxin-12-[N-(5-carboxypentyl)-N,N-dimethylaminomethyl carbonate]-3''', 4'''-cyclic carbonate, bromide salt.

Examples of model compounds useful in evaluating the methods described herein include 2-(4-nitrophenyl)ethylamine 3-(O-acetyl)-L-carnitine amide, chloride salt; 2-(4-nitrophenyl)ethylamine choline carbamate, chloride salt; 2-(4-nitrophenyl)ethanol choline carbonate ester, chloride salt; 4-(4-nitrophenyl)cyclohexanol choline carbonate ester, iodide salt; 2-[4-(4-methoxyphenyl)butyramido]ethyl O-acetyl-L-carnitinate, chloride salt; 2-[4-(4-methoxyphenyl)butyramido]ethyl O-acetyl-L-carnitinthioate, chloride salt; 2-(4-nitrophenyl)ethanol 6-(O-acetyl-L-carnitinamido))-hexanoate ester, chloride salt; 1-(4-nitrophenyl)-2-propanol 6-(O-acetyl-L-carnitinamido))-hexanoate ester, chloride salt; 2-(4-nitrophenyl)ethanol 3-(O-acetyl-L-carnitinamido))-propanoate ester, chloride salt; and 1-(4-nitrophenyl)-2-propanol 6-(O-acetyl-L-carnitinamido))-hexanol carbonate ester, chloride salt.

E. Spacer Groups

One or more spacer groups optionally may be introduced between the chemical modifier and the pharmaceutical agent. Spacer groups contain at least two chemical functionalities and, as opposed to chemical modifiers, do not carry a charge. Typically, one chemical functionality of the spacer group bonds to a chemical functionality of the chemical modifier, while the other chemical functionality of the spacer group is used to bond to a chemical functionality of the pharmaceutical agent. Examples of chemical functionalities of spacer groups include hydroxy, mercapto, carbonyl, carboxy, amino, ketone, and mercapto groups. Spacer groups may also be used in combination. When a combination of spacer groups is used, the spacer groups may be different or equivalent.

Preferred spacer groups include 6-aminohexanol, 6-mercaptohexanol, 10-hydroxydecanoic acid, glycine and other amino acids, 1,6-hexanediol, β-alanine, 2-aminoethanol, cysteamine (2-aminoethanethiol), 5-aminopentanoic acid, 6-aminohexanoic acid, 3-maleimidobenzoic acid, phthalide, α-substituted phthalides, the carbonyl group, aminal esters, and the like.

The spacer can serve to introduce additional molecular mass and chemical functionality into the pharmaceutical agent-chemical modifier complex. Generally, the additional mass and functionality will affect the serum half-life and other properties of the pharmaceutical agent-chemical modifier complex. Thus, through careful selection of spacer groups, pharmaceutical agent-chemical modifier complexes with a range of serum half-lives can be produced.

Table 4 lists the serum half-lives for several model compounds and two representative pharmaceutical agent-chemical modifier complexes using an in vitro assay system described in the Experimental section below. Of course, the serum half-lives will vary in vivo depending upon the age and health condition of the patient. Each complex comprises a model compound or a pharmaceutical agent, a spacer group, and a chemical modifier. Many of the model compounds utilize 4-nitrophenyl(ethanol, propanol, or cyclohexanol) or 4-nitrophenylethylamine as the "model" pharmaceutical agent. A more complete listing of serum half-lives may be found in the Experimental section below.

As can be seen in Table 4, the number of carbons in a spacer group has an effect on the serum half-life of the complex. For example, 2-(4-nitrophenyl)ethanol 6-(O-acetyl-L-carnitinamido)hexanoate ester, chloride salt, which utilizes 6-aminohexanoic acid as its spacer group has a serum half-life of 7.9 seconds. By changing the spacer group to β-alanine to produce 2-(4-nitrophenyl)ethyl 3-(O-acetyl-L-carnitinamido)propanoate, one can extend the half-life to 5.5 minutes.

In addition, the nature of the linkage used to couple the spacer group to the chemical modifier or pharmaceutical agent may affect the serum half-life. For example, 1-(4-nitrophenyl)-2-propanol 6-(O-acetyl-L-carnitinamido)-hexanoate ester contains 6-aminohexanoic acid as its spacer group. This spacer group is linked to the pharmaceutical agent via an ester linkage. The half-life for 1-(4-nitrophenyl)-2-propanol 6-(O-acetyl-L-carnitinamido)hexanoate ester is 21.4 minutes. If the spacer group is changed to 6-aminohexanol and the spacer group is linked to the pharmaceutical agent via a carbonate linkage, then the serum half-life becomes 3.5 minutes.

TABLE 4

| Compound | In vitro Half-Life |
|---|---|
| 2-(4-nitrophenyl)ethanol 6-(O-acetyl-L-carnitinamido))-hexanoate ester, chloride salt | 7.9 sec |
| 2-(4-nitrophenyl)ethanol 6-morpholino hexanoate | 27.8 sec |
| 2-(4-nitrophenyl)ethanol 4-morpholino benzoate | 45.7 sec |
| 1-(4-nitrophenyl)-2-propanol 6-(O-acetyl-L-carnitinamido))-hexanoate ester, chloride salt | 21.4 min |
| 2-(4-nitrophenyl)ethanol 3-(O-acetyl-L-carnitinamido))-propanoate ester, chloride salt | 5.5 min |
| 2-(4-nitrophenyl)ethanol choline carbonate ester, chloride salt | <2 sec |
| 1-(4-nitrophenyl)-2-propanol 6-(O-acetyl-L-carnitinamido))-hexanol carbonate ester, chloride salt | 3.5 min |
| 4-(4-nitrophenyl)cyclohexanol choline carbonate ester, iodide salt | 19.6 sec |
| 2-(4-nitrophenyl)ethylamine choline carbamate, chloride salt | 86 hr |
| 2-(4-nitrophenyl)ethylamine 3-(O-acetyl)-L-carnitine amide, chloride salt | 26.1 hr |

TABLE 4-continued

| Compound | In vitro Half-Life |
|---|---|
| *progesterone 3-{2-O-[6-O—(O-acetylcarnitinyl)-decanoyl]-glycolic acid} enol ester | 28.9 min |
| *3-hydroxy-estra-1,3,5-trienyl-17β-yl-6-(O-acetyl-L-carnitinato)hexyl carbonate, chloride salt | 4 hr |

*Modified pharmaceutical agent

F. Optional Funcitonality Modifiers

Although discussion has thus far focussed on the coupling of a charged chemical modifier to a pharmaceutical agent, in some embodiments, other functionality modifiers can be coupled to the pharmaceutical agent or the pharmaceutical agent-chemical modifier complex. A functionality modifier is a chemical entity which possesses at least one chemical functionality which can be covalently bound to the pharmaceutical agent-chemical modifier complex (optionally via a spacer group), which does not necessarily carry a charge, and which serves to affect or modify a chemical, physical, or biological property of the complex, including providing a means for detection, for increasing the excretion half-life of the pharmaceutical agent, for targeting the pharmaceutical agent, for increasing avidity, for decreasing aggregation, for decreasing the inflammation and/or irritation accompanying the delivery of the pharmaceutical agent across membranes, and for facilitating receptor crosslinking. Thus, chemical modifiers constitute a species within the broader class of functionality modifiers.

In theory, the functionality modifier can be bound to either the pharmaceutical agent, a chemical modifier, or a spacer group. Typically, when both a chemical modifier and a functionality modifier are used, because the chemical modifier is cleaved from the pharmaceutical agent-chemical modifier complex after membrane transport, the functionality modifier will be covalently coupled to the pharmaceutical agent or the spacer group.

An example of a functionality modifier which serves to provide a means for detection is a radiolabeling site, including radiolabeled chelates for cancer imaging or radiotherapy and for assessing dose regiments in different tissues, such as kemptide.

Other functionality modifiers are capable of extending the excretion half-life of a pharmaceutical agent. Typically, these modifiers will find use with peptide and protein drugs or other pharmaceutical agents with short excretion half-lives. Generally, this modifier will comprise a moiety capable of binding to a serum protein, such as human serum albumin. Typically those moieties will be bound to plasma more than 60%, preferably more than 70%, more preferably more than 80%, and most preferably more than 90%, as measured by the procedures known in the art. Examples of such effector groups include naproxen, fluoxetine, oxazepam, nitrazepam, phenylbutazone, nortriptyline, methadone hydrochloride, lorazepam, imipramine, haloperidol, flurazepam, doxycycline, ditonin, diflunisal, diazoxide, diazepam, nordazepam, desipramine, dapsone, clofibrate, amantadine, chlorthalidone, clonazepam, chlorpropamide, chlorpromazine, chlorpheiramine, chloroquine, carbamazepine, auranofin, amitriptyline, amphotericin B, piroxicam, warfarin, pimozide, doxorubicin, pyrimethamine, amidoarone, protriptylene, desipramine, nortriptyline, oxazepam, nitrazepam, and tetrahydrocannabinols.

Alternatively, the excretion half-life functionality modifier will comprise a circulating carrier protein, for example, an antibody, or antigen-binding fragment, or genetically-engineered binding protein derived therefrom. See, e.g., Huston et al. (1988) *Biochem.* 85:5879–5883. The antibody, fragment, or derivative thereof should have a relatively long half-life in the circulation, generally on the order of about 1–24 hours, and preferably about 12–24 hours. Because the half-lives of antibody fragments are generally shorter than that of intact antibodies, it may be necessary to increase the half-life of the fragments by attaching polyethylene glycol or polyamino acid chains to the fragment.

In some embodiments, the functionality modifier will serve as a "targeting" modifier and serve to increase tissue or organ specificity, increase the local concentration of drug in the target tissue, or intracellular or transcellular targeting of the active drug. Typically, this type of "targeting" modifier will comprise a peptide that binds to a cell surface receptor and preferably, peptides that bind to an internalized receptor, such as transferrin. The simultaneous use of two different targeting modifiers could result in greater specificity as well as high avidity.

The targeting modifier can also serve to "target" or direct the pharmaceutical agent-chemical modifier complex inside a cell, i.e., to achieve internalization of the complex. Internalization of a ligand at the surface of cells can result if the substance is univalent and the receptor-ligand interaction leads to the formation of endocytotic vesicles. In general, however, internalization is greatly enhanced if the ligand is multivalent. Multiple receptor molecules are thereby bound to the ligand molecule and formation of an endocytotic vesicle follows rapidly.

Internalization of a drug via the endocytic route offers several advantages. First, endocytotic vesicles generally fuse with acidic vesicles wherein ligand-receptor dissociation occurs at low pH. In addition, acid vesicles contain diverse hydrolytic enzymes including esterases and proteases. These factors can be exploited for the dissociation or cleavage of the pharmaceutical agent-chemical modifier complex. Finally, fusion of endocytotic vesicles with intracellular acid vesicles does not always occur, especially in cells such as epithelial cells (and some endothelial cells) that engage in transcellularly directed molecular trafficking. For example, the directed movement of peptides across gut epithelial cells involves several pathways, including the directed movement of vesicles from the gut lumen to the basal cell surface (transcytosis). At this surface, fusion of the vesicles with the basal cell plasma membrane releases the vesicle contents into the extracellular space allowing their subsequent transfer into the gut microcirculation or lymph. The transcytotic movement of endocytotic vesicles across the endothelial cells constituting the blood-brain barrier is a similar process, yielding a net flux of endocytosed molecules from the blood to the brain compartment.

Hence, direction of a pharmaceutical agent to an intracellular vesicle compartment via receptor-mediated endocytosis can represent a route for drug effects on the epithelial/endothelial cell, as well as a route for drug transport across otherwise drug impermeable cell monolayers. A cell internalization modifier typically will comprise a receptor specific targeting modifier, for example, folic acid or folate, which is implicated in receptor mediated endocytosis (clathrin pits). Alternatively, the modifier could comprise a membrane active molecule, such as the peptide melittin, for the transport of small, hydrophobic drugs across the cell membrane. Membrane active peptides, such as derivatives of domain II of Pseudomonas exotoxin, can be used to transport the pharmaceutical agent-chemical modifier complex from vesicles into the cytoplasm.

Functionality modifiers can also serve to increase the avidity of receptor binding. Typically a dimerization peptide, such as the peptide linker SKVILF will be used. Formation of the high-avidity dimer will occur preferentially on tissues with high receptor concentration and thus, will also provide additional specificity for tissues with high receptor densities.

A receptor crosslinking functionality modifier is essentially a targeting modifier. Crosslinking of cell surface receptors is a useful ability for a pharmaceutical agent in that crosslinking is often a required step before receptor internalization. Thus, the crosslinking modifier can be used as a means to incorporate a pharmaceutical agent into a cell. In addition, the presence of two receptor binding sites (i.e., targeting modifiers) gives the pharmaceutical agent increased avidity.

A similar effect can also be obtained with an avidity modifier. In this case, each pharmaceutical agent will have a targeting modifier and an avidity modifier (i.e., a dimerization peptide). The dimerization of two peptides will effectively form one molecule with two targeting modifiers, thus allowing receptor crosslinking. With this bimolecular approach to crosslinking, the concentration dependence will be greater and increased targeting and crosslinking specificity can be obtained for tissues with high receptor density.

Alternatively, a functionality modifier may serve to prevent aggregation. Specifically, many peptide and protein pharmaceutical agents form dimers or larger aggregates which may limit their permeability or otherwise affect properties related to dosage form or bioavailability. For example, the hexameric form of insulin can be inhibited through the use of an appropriate functionality modifier and thus, result in greater diffusability of the monomeric form of insulin.

G. Bi- and Multi-functional Modifiers, Pharmaceutical Agents, and Spacer Groups Many chemical modifiers and pharmaceutical agents, such as carnitine, lysine, and yohimbic acid, and all spacer groups possess more than one chemical functionality. For example, either the hydroxyl or carboxy of carnitine may be exploited to produce esters of carnitine and a pharmaceutical agent. Likewise, either the amino or carboxy groups of lysine may serve as its chemical functionality. Similarly, yohimbic acid possesses a hydroxyl group and a carboxy group with which it may bind to a chemical modifier.

Bi- and multi-functional chemical modifiers and multi-functional spacer groups are particularly preferred in that they provide an additional means of altering the physicochemical properties, and hence, the pharmacokinetics and transmembrane delivery of the pharmaceutical agent-chemical modifier complex through derivatization of the extra functionality. The derivatization may occur either prior to or after coupling of the chemical modifier or spacer group to the pharmaceutical agent.

Carnitine is a particularly preferred bifunctional chemical modifier because of the ease with which its derivatization may be accomplished. For example, the hydroxyl group of carnitine may be utilized in a reaction with fatty acids of varying chain lengths. The carboxy group may then be exploited to form a bond with a pharmaceutical agent. An example of a pharmaceutical agent-chemical modifier complex containing a derivatized carnitine is digitoxigenin-3-

(O-palmitoyl-L-carnitine) ester, chloride salt which contains the palmitoyl derivative of carnitine. These derivatives provide great flexibility in synthesizing compounds of the invention that have the delivery, transport, hydrophobic character, and optimum half-life one desires.

Persons skilled in the art will appreciate that it may be necessary to block or protect selectively one functionality of a chemically bi- or multi-functional chemical modifier, pharmaceutical agent, or spacer group in order to exploit the other functionality effectively. Functionalities which may need to be protected include, but are not limited to, hydroxy, mercapto, amino, and carboxy groups.

A variety of protecting groups may be used to block or protect a chemical functionality. The choice of protecting group will depend on many factors including sensitivity of the molecule to reaction conditions and other functionality in the molecule. In addition, the protecting group may be chosen for its effect on serum half-life of the resulting pharmaceutical agent-chemical modifier complex. Examples of protecting groups and techniques for protection and deprotection can be found in Greene et al. *Protective Groups in Organic Synthesis,* 2nd Ed., John Wiley & Sons: New York (1991), which is incorporated herein by reference.

III. PREPARATION OF THE PHARMACEUTICAL AGENT-CHEMICAL MODIFIER COMPLEX

A. General

The pharmaceutical agent-chemical modifier complex may be produced using either chemical or biochemical techniques. Biochemical techniques are used primarily in the case of protein drugs and include recombinant expression methods.

Typically, the pharmaceutical agent is linked to a chemical modifier using standard chemical techniques through their respective chemical functionalities. Optionally, the chemical modifier or pharmaceutical agent may be coupled to a spacer group prior to formation of the pharmaceutical agent-chemical modifier complex. Schematically, the complex may be represented as pharmaceutical agent-$[(\text{spacer})_x$-(chemical modifier)$_y]_z$ or A-$(S_x\text{-}M_y)_z$ wherein x is 0–10, y is y-10 and z is 1–10 and A is the pharmaceutical agent, S is the spacer group and M is the chemical modifier. The spacer groups may be equivalent or different when used in combination. Likewise, if more than one chemical modifier is used to produce the pharmaceutical agent-chemical modifier complex, the chemical modifiers may be equivalent or different. In some embodiments, at least one functionality modifier will also be covalently linked, optionally via a spacer group(s), to the pharmaceutical agent, chemical modifier, and/or spacer group.

The ratio of pharmaceutical agent to chemical modifier can be about 1:10 (i.e., y is 10). to about 1:5 (i.e., y is 5), and most preferably, about 1:1 (i.e., y is 1). Typically, the pharmaceutical agent-chemical modifier complex will have a molecular weight of less than about 50,000, more often less than about 25,000 daltons, and most preferably, less than about 15,000 daltons.

B. Multi-Adducts

If the pharmaceutical agent has more than one chemical functionality, it can be coupled to more than one chemical modifier. A bis-adduct will result if the pharmaceutical agent binds to two molecules of a single chemical modifier.

Alternatively, a pharmaceutical agent may bind with several different chemical modifiers. One skilled in the art will appreciate that this might best be accomplished through a sequential coupling scheme. For example, one of the chemical functionalities of the pharmaceutical agent is first selectively protected. A chemical modifier is then joined to the remaining chemical functionalities of the pharmaceutical agent. The protecting group on the pharmaceutical agent is removed to release the chemical functionality which may then be coupled to a second chemical modifier.

Preferred examples of bis adducts include piroxicam-N, O-bis(choline chloride) carbonate ester; pregn-5-ene-3,20-dione 3,20-bis(glycerol-(O-acetyl-L- carnitinate))ketal; digoxin 3',3'',12-tris-(6-trimethylaminohexanoyloxymethyl carbonate)-3''',4'''-cyclic carbonate, tribromide salt; 5-fluorouracil-1,3-bis-(2-trimethylaminoethoxycarbonyloxymethyl), diiodide salt; and 6-mercaptopurine-S,9-bis-[6-(N,N,N-trimethylamino)hexanoyl-oxymethyl], diiodide salt.

C. Recombinant Approaches

Many protein drugs (including INF-$\alpha 2$) or chemical modifiers are manufactured in recombinant expression systems. These recombinant systems allow for the introduction or deletion of charged (positively or negatively) residues from the protein thus, allowing for enhanced transport and delivery of the modified protein through membranes without requiring the attachment of a separate chemical modifier. For example, one mode of addition of charged residues is as N- or C-terminal tails. These could be designed to be labile to proteases in the skin or serum, effecting the removal of the charged tail after delivery.

A further aspect of this embodiment would relate to the use of propeptide sequences as target sites for mutagenesis to enhance the electrotransport of proteins. For example, mature insulin results from two discreet processing steps, from preproinsulin to proinsulin to mature insulin. The conversion of proinsulin to the mature form is accompanied by the proteolytic removal of the 35 amino acid C-chain. The amino acid residues within this removable C-chain that are nonessential for processing and folding can be modified, e.g., by increasing or decreasing the net charge or by altering the charge localization or distribution, to enhance the delivery and transport of proinsulin and hence, insulin, through membranes. Upon delivery; the prodrug (i.e., proinsulin) is converted to the active drug (i.e., insulin) by cleavage of the "chemical modifier" (i.e., the removable C-chain). This approach will also find use with other proteins and peptides having a pro-form, such as thymosin alpha 1 which results from the processing of its precursor form, prothymosin.

In addition, fusion protein consisting of the pharmaceutical agent covalently bound to various highly charged peptides can be produced. This can be achieved by fusing the cloned gene encoding the pharmaceutical agent to a segment that encodes a charged peptide residue containing several charged (positively or negatively) amino acids. These charged peptide residues would be rich in lysine, arginine and/or histidine. The net charge on the residues, as well as the charge distribution and localization, can be varied. To facilitate purification of such fusion proteins, the actual genetic constructs engineered for expression may incorporate oligonucleotides encoding the recognition sequence from maltose binding protein joined to the desired fusion protein by a bond that can be cleaved after passage through a column of immobilized maltose. See U.S. application Ser.

No. 07/876,288, filed Apr. 29, 1992, which is incorporated herein by reference.

Alternatively, protein drugs or chemical modifiers which contain a plurality of charged residues may be engineered to delete some of these residues. Likewise, the charge distribution and localization of the protein drugs or chemical modifiers can be altered. Thus, using recombinant expression techniques and the addition or deletion of charged residues, it is possible to tailor the drug's biological properties, including its transmembrane transport and delivery rates.

Enzymes also can be employed as a means for modifying protein and peptide drugs to enhance their delivery and transport through membranes. According to one embodiment, the enzyme will comprise an esterase, i.e., an hydrolase that can convert an ester into an acid residue and an alcohol residue. The acid may be a carboxylic, a phosphoric, or a sulfuric acid; and the ester may be an alcoholic or a thiol ester. According to this embodiment, a protein or peptide drug (i.e., the acid residue) is contacted with an esterase, such as cholinesterase, and a large excess of the alcohol residue, such as choline. A large excess of the alcohol residue is utilized to drive the equilibrium towards ester formation thus, incorporating the alcohol residue. If the alcohol residue is charged (i.e., a chemical modifier), then ester formation will result in the introduction of charge to the protein or peptide drug and hence, the enhancement of the drug's transport and delivery through membranes.

More generally, this method will be applicable with any enzyme capable of posttranslational modification of a protein and can result in either the introduction of positive charge or the deletion of negative charge. Examples of these enzymes include, but are not limited to, those enzymes responsible for the following amino acid modifications: hydroxylation of proline and lysine residues to form the hydroxyproline and hydroxylysine residues in Collagen; phosphorylation of serine to phosphoserine, carboxylation of glutamate to $\gamma$-carboxyglutamate; the introduction of amide groups to C-terminal residues, e.g., glycinamide; the methylation, acetylation or phosphorylation of the $\epsilon$-amino group of lysine; glycosylation; and the attachment of prosthetic groups, e.g., the attachment of carbohydrates to glycoproteins.

The processes for manipulating, amplifying, and recombining DNA which encode amino acid sequences of interest are generally well known in the art, and therefore, not described in detail herein. Methods of identifying and isolating genes encoding proteins of interest, or for constructing such genes, are well understood and developed. These processes are described in the patent and other literature. See, for example, U.S. Pat. Nos. 4,431,739 and 5,013,653.

Accordingly, DNA construction principles can be exploited using known construction techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short oligonucleotides, cDNA synthesis techniques, and synthetic probes for isolating genes having a particular function. Various promoter sequences and other regulatory DNA sequences used in achieving expression, and various types of host cells are also known and available. Conventional transfection techniques, and equally conventional techniques for cloning and subcloning DNA may also be used and are known to those of skill in the art. Various types of vectors may be used such as plasmids and viruses including animal viruses and bacteriophages. The vectors may exploit various marker genes which impart to successfully transfected cells a detectable phenotypic characteristic that can be used to identify which of a family of cells has successfully incorporated the recombinant DNA of the vector. The production of various proteins of interest may be achieved by expressing fused protein which is collected, purified, and then cleaved to remove the extraneous portion of the molecule.

IV. COMPOSITIONS OF THE PHARMACEUTICAL AGENT-MODIFIER COMPLEX

As applied to the improvement of a pharmaceutical agent's delivery and transport through membranes, the invention provides pharmaceutical agent-chemical modifier complexes with a charge-to-mass ratio that allows the complex to be delivered in therapeutically effective amounts. Typically, the charge-to-mass ratio of such a complex will be equal to or exceed one charge per 5000 daltons. Preferably, the charge-to-mass ratio will be equal to or exceed one charge per 2500 daltons. Most preferably, the charge-to-mass ratio will be equal to or exceed one charge per 1000 daltons.

The pharmaceutical agent-modifier complex can be admixed with an acceptable physiological carrier, such as water, aqueous alcohols, propylene glycol, dimethylsulfoxide, to make a composition suitable for contact with the various membranes and transport and delivery through these membranes. Well known techniques for choosing appropriate carriers and formulating the proper mixtures are exemplified in Banga et al. supra; Lattin et al. (1991) *Ann. N.Y. Acad. Sci.* 618:450; and *Remington's Pharmaceutical Science,* 15th Ed., Mack Publishing Company, Easton, Pa. (1980) and Goodman and Gillman supra, which are incorporated herein by reference.

In addition to the pharmaceutical agent-chemical modifier complex, the composition may contain other materials such as dyes, pigments, inert fillers, or other permeation enhancers, excipients, and conventional components of pharmaceutical products or transdermal therapeutic systems as known in the art.

V. IN VITRO TESTING OF PHARMACEUTICAL AGENT-CHEMICAL MODIFIER COMPLEXES

The activity of the pharmaceutical agent-modifier complex may be ascertained through studies of the hydrolytic or enzymatic conversion of the complex to the unbound pharmaceutical agent. Generally, good correlation between in vitro and in vivo activity is found using this method. See, e.g., Phipps et al. (1989) *J. Pharm. Sciences* 78:365. The rates of conversion may be readily determined, for example by spectrophotometric methods or by gas-liquid or high pressure liquid chromatography. Half-lives and other kinetic parameters may then be calculated using standard techniques. See, e.g., Lowry et al. *Mechanism and Theory in Organic Chemistry,* 2nd Ed., Harper & Row, Publishers, New York (1981).

In addition, the in vitro skin permeation rate of a pharmaceutical agent-chemical modifier complex can be measured using flow-through diffusion cells. Typically these cells will have an active area of 1 $cm^2$ and a receiving volume of 3 ml. The receptor fluid, generally isotonic saline, is pumped into and through the cells, by a peristaltic pump. Samples are collected in glass vials arranged in an automatic fraction collector. Human, mouse, or porcine skin is placed on the lower half of the diffusion cell with the stratum corneum facing the donor compartment. The transdermal device is placed on the stratum corneum and the amount of drug permeating across the skin (μg/cm$^2$.hr) is calculated from the cumulative release. Alternatively, a solution of the complex can be placed into the donor compartment and the amount of transported drug can be calculated.

The electrotransport behavior of the charged complex in comparison with the pharmaceutical agent may also be assessed using the above analytical techniques and gel or capillary electrophoresis. In general, if a complex shows faster mobility during electrophoresis than the unmodified pharmaceutical agent, then the complex merits further study for improved iontophoretic transdermal deliverability. Preparation measurements may also be performed on excised skin in conventional diffusion cell tests. See Lattin et al. supra.

VI. IN VIVO DELIVERY OF PHARMACEUTICAL AGENT-CHEMICAL MODIFIER COMPLEXES

A. General

Methods of derivatizing pharmaceutical agents so as to modify a property of the pharmaceutical agent are described herein. Examples of properties that can be modified include membrane transport rate, delivery rate, serum half-life, and biodistribution, including the enhancement of pharmacokinetic and pharmacodynamic properties, such as lipophilicity and/or solubility, and partition coefficient. Thus, the complexes described herein will find use in the treatment of a variety of diseases, including but not limited to those described below. For example, pharmaceutical agents can be designed to prevent expression of diverse potential target genes, including oncogenes, fungal genes, and any other gene known to be activated specifically in the skin. These pharmaceutical agents can then be delivered directly to melanomas, Kaposi sarcomas, psoriasis lesions, and fungal infected skin, and the like. The complexes described herein will find use in the treatment of viral, fungal, and bacterial infections of the skin and mucous membranes, including genital warts caused by the human papilloma virus and infections caused by Herpes viruses. In addition, the present invention provides for the delivery of therapeutic compositions of pharmaceutical agent-chemical modifier complexes directly to block mediators of inflammation, including cytokines, growth factors, cell adhesion molecules or their ligands and receptors thereof, as well as key enzymes in pathways leading to inflammation. More specifically, these blocking actions include preventing the expression of cytokines (such as IL-1), growth factors (such as TGF-α and EGF), or cell adhesion molecules (such as ELAM and ICAM); or the receptors for cytokines (such as IL-1), growth factors, or cell adhesion molecules. Key enzymes whose expression may be blocked include protein kinase C and phospholipase A or C. Thus, according to one aspect of this invention, topical or transdermal formulations of the complexes described herein are applied directly knees or other joints to alleviate inflammation and the like.

In yet another aspect, the complexes described herein can be used to treat conditions in which improper immune or inflammatory responses have been implicated such as psoriasis (e.g., by blocking the expression of IL-1, TGFα, amphiregulin, or IL-6); atopic dermatitis and eczema (e.g., by blocking the overexpression of IgE); rheumatoid arthritis; allergic rhinitis (e.g., by blocking the expression of IL-4); and the likc. In an additional aspect, the complexes described herein can be used to treat certain cancers of the skin and mucous membranes, such as melanoma, mycosis fungoides, and squamous cell carcinoma (including of the cervix), for example, by blocking the expression of certain factors which promote cell growth and/or adhesion and which are believed to be involved in metastasis.

Additionally, the methods described herein can find use in the amelioration of side effects associated with a given pharmaceutical agent. Specifically, introduction of a charged chemical modifier to the 12-position of digoxin has been found to substantially decrease the cytotoxicity of digoxin. The following compounds have been found to be less cytotoxic than digoxin:

| Position | Substituent | Half Life |
|---|---|---|
| 12 | $(CH_3)_3N^+(CH_2)_3(CO)O—$ | 4 days |
| 12, 3', 3" | $(CH_3)_3N^+(CH_2)_5(CO)OCH_2O(CO)O—$ | 14 hours |
| 3', 3" | $(CH_3)_3N^+(CH_2)_5(CO)OCH_2O(CO)O—$ | 10 hours |
| 12 | $(CH_3)_3N^+(CH_2)_5(CO)OCH_2O(CO)O—$ | 2.8 hours |

B. Transdermal Delivery i. General

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1–3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

ii. Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

iii. Iontophoresis

According to some embodiments, the therapeutic composition will be delivered by a standard iontophoretic device. In general, iontophoresis is an introduction, by means of electric current, of ions of soluble salts into the tissues of the body. More specifically, iontophoresis is a process and technique which involves the transfer of ionic (charged) species into a tissue (for example through the skin of a patient) by the passage of a electric current through an electrolyte solution containing ionic molecules to be delivered (or precursors for those ions), upon application of an appropriate electrode polarity. That is, ions are transferred into the tissue, from an electrolyte reservoir, by application of electromotive force to the electrolyte reservoir. In iontophoretic systems, the rate of release is primarily controlled by the voltage or current.

If the electrotransport method is iontophoresis, generally the active electrode includes the therapeutic species as a charged ion, or a precursor for the charged ion, and the transport occurs through application of the electromotive force to the charged therapeutic species. If other electrotransport phenomenon are involved, then the therapeutic species will be delivered in an uncharged form, transfer being motivated, however, by electromotive force. For example, the applied current may induce movement of a non-therapeutic species, which carries with it water into the subject. The water may have dissolved therein the therapeutic species. Thus, electrotransport of the non-therapeutic charged species induces movement of the therapeutic but non-charged species.

Through iontophoresis, either positively charged pharmaceutical agent-chemical modifier complexes or negatively charged complexes can be readily transported through the skin and into the patient. This is done by setting up an appropriate potential between two electrode systems (anode and cathode) in electrical contact with the skin. If a positively charged drug is to be delivered through the skin, then an appropriate electromotive force can be generated by orienting the positively charged drug species at a reservoir associated with the anode. Similarly, if the ion to be transferred across the skin is negatively charged, then an appropriate electromotive force can be generated by positioning the drug in a reservoir at the cathode. Of course, a single system can be utilized to transfer both positively charged and negatively charged drugs into a patient at a given time; and, more than one cathodic drug and/or more than one anodic drug may be delivered from a single system during a selected operation. For general discussions of iontophoresis, see, e.g., Tyle (1989) *J. Pharm. Sci.* 75:318; Burnette, Iontophoresis (Chapter 11) in *Transdermal Drug Delivery* Hadgraft and Guy (eds.) Marcel Dekker, Inc.: New York, N.Y.; Phipps et al. (1988) *Solid State Ionics* 28–30:1778–1783; Phipps et al. (1989) *J. Pharm. Sciences* 78:365–369; and Chien et al. (1988) *J. Controlled Release* 7:1–24, the full disclosures of which are incorporated herein by reference.

A wide variety of iontophoresis devices are presently known. See, e.g., Phipps et al. U.S. Pat. No. 4,744,788; Phipps et al. U.S. Pat. No. 4,747,819; Tapper et al. European Patent Application Publication No. 0318776; Jacobsen et al. European Patent Application Publication No. 0299631; Petelenz et al. U.S. Pat. No. 4,752,285; Sanderson et al. U.S. Pat. No. 4,722,726; Phipps et al. U.S. Pat. No. 5,125,894; and Parsi U.S. Pat. No. 4,731,049, Badzinski et al. (1993) U.S. Pat. No. 5,207,752; Gyory et al. (1993) U.S. Pat. No. 5,203,768; Gyory et al. (1992) U.S. Pat. No. 5,162,042; Phipps (1992) PCT Publication No. WO 92/17239; Landrau et al. (1992) PCT Publication No. WO 92/15365; Gyory et al. (1992) Canadian Patent Publication 2,042,994; Gyory et al. (1992) U.S. Pat. No. 5,158,537; Gyory et at. (1992) PCT Publication No. WO 92/07618; Myers et al. (1992) U.S. Pat. No. 5,147,297; Gyory et al. (1992) U.S. Pat. No. 5,147,297; Gyory et al. (1991) Canadian Patent Publication No. 2,015,597; Gyory et al. (1992) U.S. Pat. No. 5,084,006; Gyory et al. U.S. Pat. No. 5,162,043; Haak et al. (1992) U.S. Pat. No. 5,167,616; Gyory et al. (1990) PCT Publication No. 90/09413; Theeuwes et al. (1992) U.S. Pat. No. 5,080,646; Theeuwes et al. (1992) U.S. Pat. No. 5,147,296; Theeuwes et al. (1992) U.S. Pat. No. 5,169,382; Theeuwes et al. (1992) U.S. Pat. No. 5,169,383; Theeuwes (1990) U.S. Pat. No. 4,978,337; Moodie et al. (1992) U.S. Pat. No. 5,125,894; Haak et al. (1990) U.S. Pat. No. 4,927,408; the full disclosures of each which are incorporated herein by reference.

In typical, conventional, electrotransport devices, for example iontophoresis devices, two electrodes are generally used. Both electrodes are disposed so as to be in intimate electrical contact with some portion (typically skin) of the subject (human or animal) typically by means of two remote electrolyte-containing reservoirs, between which current passes as it moves between the skin and the electrodes. One electrode, generally referred to herein as the "active" electrode, is the electrode from which the pharmaceutical agent-chemical modifier complex is delivered or driven into the body by application of the electromotive force. The other electrode, typically referred to as an "indifferent" or "ground" electrode, serves to close the electrical circuit through the body. In some instances both electrodes may be "active", i.e. drugs may be delivered from both. Herein the term electrode, or variants thereof, when used in this context refers to an electrically conductive member, through which a current passes during operation.

A variety of electrode materials, ranging from platinum to silver-silver chloride, are available for these devices. The primary difference in these materials is not in their ability to generate an electric potential across the skin, but rather in certain nuances associated with their performance of this function. For example, platinum electrodes hydrolyze water, thus liberating hydrogen ions and subsequently, changes in pH. Obviously, changes in pH can influence the ionization state of therapeutic agents and their resulting rate of iontophoretic transport. Silver-silver chloride electrodes, on the other hand, do not hydrolyze water. However, these electrodes require the presence of chloride ion which may compete for current-induced transport.

Electrotransport devices generally require a reservoir as a source of the species (or a precursor of such species) which is to be moved or introduced into the body. The reservoir typically will comprise a pool of electrolyte solution, for example an aqueous electrolyte solution or a hydrophilic, electrolyte-containing, gel or gel matrix, semi-solid, foam, or absorbent material. Such pharmaceutical agent-chemical modifier complex reservoirs, when electrically connected to the anode or the cathode of an iontophoresis device, provide a source of one or more ionic species for electrotransport.

Many iontophoresis devices employ a selectively permeable membrane. The composition of this membrane will vary with the particular needs of the system and will depend upon the composition of the electrolyte reservoir, i.e., the nature of the pharmaceutical agent or pharmaceutical agent-chemical modifier complex, the transference of current out of the reservoir, and the desired selectivity to transport of particular types of charged and uncharged species. A microporous polymer or hydrogel such as is known in the art can be utilized. See, e.g., U.S. Pat. No. 4,927,408.

Suitable permeable membrane materials can be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethanepolyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Generally, buffers will also be incorporated into the reservoir to maintain the reservoir environment at the same charge as the electrode. Typically, to minimize competition for the electric current, a buffer having the opposite charge to the drug will be employed. In some situations, for example, when the appropriate salt is used, the drug may act as its own buffer.

Other variables which may effect the rate of transport include drug concentration, buffer concentration, ionic strength, nonaqueous cosolvents, and any other constituents in the formulation. In general, to achieve the highest transport efficiency, the concentration of all ionic species, save the pharmaceutical agent-chemical modifier complex itself, is minimized.

In conjunction with the patient's skin in electrical communication with the electrodes, the circuit is completed by connection of the two electrodes to a source of electrical energy as a direct current; for example, a battery or a source of appropriately modified alternating current. As an example, if the ionic substance to be driven to the body is positively charged, then the positive electrode (the anode) will be the active electrode and the negative electrode (the cathode) will serve to complete the circuit. If the ionic substance to be delivered is negatively charged, then the negative electrode (cathode) will be the active electrode and the positive electrode (anode) will be the indifferent electrode.

Chemical enhancers and electroporation can also be utilized to alter the iontophoretic transport rate. For example, the coapplication of oleic acid to the skin causes a large decrease in the skin impedance or resistance which is inversely related to permeability or transport. See Potts et al. (1992) *Solid State Ionics* 53–56:165–169. Thus, instead of the current passing primarily through the shunt pathways (e.g., the follicles and sweat ducts), the ions constituting the current can more uniformly permeate the lipid milieu of the stratum corneum at a lower current density. Thus, the epidermis, as well as the peripheral neurons surrounding the hair follicles and sweat ducts, will be able to experience the electrical stimulation.

The backing or enclosure of the drug delivery system is intended primarily as a mechanical support for the reservoir or matrix. In the simplest case, the matrix is exposed directly to the skin or membrane of the host, and the backing is a strip or patch capable of being secured to the skin, typically with the matrix acting as an adhesive. In such constructions, the backing will usually be impermeable to the complex. This impermeability inhibits the loss of the complex. Suitable backing materials will generally be thin, flexible films or fabrics such as woven and non-woven fabrics and polymeric films, such as polyethylene, polypropylene, and silicone rubber; metal films and foils; and the like.

The delivery device can be held in place with the adhesive of the matrix, with an adhesive along the perimeter of the matrix, with tape or elastic, or any other means, so long as the device allows the pharmaceutical agent-chemical modifier complex to be transported through the skin. The device can be placed on any portion of the skin or dermal surface, such as the arm, abdomen, thigh, and the like. Furthermore, the device can be in various shapes and can consist of one or more complexes and/or transport areas. Other items can be contained in the device, such as other conventional components of therapeutic products, depending upon the desired device characteristics.

Owing to differences in available iontophoretic devices the procedure for use can vary. The manufacturer's instructions should be followed for appropriate pharmaceutical agent delivery. Body fluid or blood levels of the uncomplexed pharmaceutical agent will be determined to measure the effectiveness of the transport and bioconversion.

In the conventional topical treatment by iontophoresis, the direct current is applied through moist pad-type electrodes with size corresponding to that of the skin region to be treated. The interposition of a moist pad between the electrode plate and the skin is necessary for making a perfect contact, preventing any skin burns, overcoming skin resistance, and protecting the skin from absorbing any caustic metal compounds formed on the metal plate surface.

The drug is administered through an electrode having the same charge as the drug, and a return electrode opposite in charge to the drug is placed at a neutral site on the body surface. The operator then selects a current intensity below the pain threshold level of the patient and allows the current to flow for an appropriate length of time. Ions transferred through the skin are taken up by the micro-circulation at the dermal-epidermal junction, while the current proceeds through the skin tissues to the return electrode. The current intensity should be increased slowly, maintained for the length of time of the treatment, and then decreased slowly at the end of the treatment. The current must be within comfortable toleration of the patient, with a current density which is generally less than 0.5 mA/cm$^2$ of the electrode surface.

iv. Topical Treatments

One aspect of this invention provides for the topical delivery of therapeutic compositions of pharmaceutical agent-chemical modifier complexes of pharmaceutical agents. This treatment regimen is suitable either for the systemic administration of the pharmaceutical agent or for localized therapy, i.e., directly to pathological or diseased tissue.

Typically, the topical formulations will comprise a preparation for delivering the pharmaceutical agent-chemical modifier complex directly to the affected skin comprising the complex, typically in concentrations in the range of from about 0.001% to 10%; preferably, from about 0.01 to about 10%; more preferably, from about 0.1 to about 5%; and most preferably, from about 1 to about 5%, together with a non-toxic, pharmaceutically acceptable topical carrier. See Dermatological Formulations: Percutaneous Absorption, Barry (ed.), Marcel Dekker Inc., (1983). For standard dosages of conventional pharmaceutical agents, see, e.g., *Physicians Desk Reference* (1992 Edition); and American Medical Association (1992) *Drug Evaluations Subscriptions*.

Topical preparations can be prepared by combining the pharmaceutical agent-chemical modifier complex with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

Dosage forms for the topical administration of a complex of this invention include powders, sprays, ointments, pastes, creams, lotions, gels, solutions, patches and inhalants. The active compound may be mixed under sterile conditions with a pharmaceutically- acceptable carrier, and with any preservatives, buffers, or propellants which may be required.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

C. Transmucosal Delivery

Although much of the discussion herein has centered on techniques for transdermal delivery, the methods of the present invention are also applicable to the enhanced transport and delivery of pharmaceutical agents through mucosal membranes, such as gastrointestinal, sublingual, buccal, nasal, pulmonary, vaginal, corneal, and ocular membranes. See, e.g., Mackay et al. (1991) *Adv. Drug Del. Rev,* 7:313–338. Specifically, there are many similarities between skin and mucosal membranes. For example, the membrane of the buccal cavity is non-keratinized. However, the buccal membrane is similar to the skin because both are stratified with the former consisting of polygonal cells at the basal membrane leading to squamous cells at the surface.

Transmucosal (i.e., sublingual, buccal and vaginal) drug delivery provides for an efficient entry of active substances to systemic circulation and reduce immediate metabolism by the liver and intestinal wall flora. Transmucosal drug dosage forms (e.g., tablet, suppository, ointment, gel, pessary, membrane, and powder) are typically held in contact with the mucosal membrane and disintegrate and/or dissolve rapidly to allow immediate systemic absorption.

i. Buccal Administration

For delivery to the buccal or sublingual membranes, typically an oral formulation, such as a lozenge, tablet, or capsule will be used. The method of manufacture of these formulations are known in the art, including but not limited to, the addition of the pharmaceutical agent-chemical modifier complex to a pre-manufactured tablet; cold compression of an inert filler, a binder, and either a pharmaceutical agent-chemical modifier complex or a substance containing the complex (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmaceutical agent-chemical modifier complex into the mouth and through the buccal mucosa.

ii. Nasal/Pulmonary Administration

For delivery to the nasal and/or pulmonary membranes, typically an aerosol formulation will be employed. The term "aerosol" includes any gas-borne suspended phase of the pharmaceutical agent-chemical modifier complex which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the pharmaceutical agent-chemical modifier complex suspended in air or other carrier gas, which may be delivered by insufflation from an inhaler device, for example.

For solutions used in making aerosols, the preferred range of concentration of the pharmaceutical agent-chemical modifier complex is 0.1–100 milligrams (mg)/milliliter (ml), more preferably 0.1–30 mg/ml, and most preferably, 1–10 mg/ml. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Iones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Solutions of the pharmaceutical agent-chemical modifier complex may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

VII. CLEAVAGE OF THE COMPLEXES

The pharmaceutical agent is coupled to the chemical modifier via a covalent bond. This covalent bond may be non-reversible, partially reversible, or preferably, reversible. The degree of reversibility corresponds to the ability of the pharmaceutical agent-chemical modifier complex to hydrolyze in vivo.

Preferably, the bond will be reversible (i.e., easily hydrolyzed) or partially reversible (i.e., partially or slowly hydrolyzed). Cleavage of the bond can occur through biological or physiological processes. Sometimes the physiological processes will cleave bonds at other locations within the complex (e.g., removing an ester group or other protecting group that is coupled to an otherwise sensitive chemical functionality) before cleaving the bond between the pharmaceutical agent and chemical modifier, resulting in partially degraded complexes; or multiple cleavages will occur, for example, between the spacer and agent and then the spacer and modifier.

For rapid activation of the complex after transport, circulating enzymes in the plasma can be used to cleave the chemical modifier from the pharmaceutical agent. These enzymes can include non-specific aminopeptidases and esterases, dipeptidyl carboxy peptidases, proteases of the blood clotting cascade, and the like.

Alternatively, cleavage may be brought about by nonenzymatic processes. For example, chemical hydrolysis may be initiated by differences in pH experienced by the complex following delivery. In such a case, the pharmaceutical agent-chemical modifier complex may be characterized by a high degree of chemical lability at physiological pH of 7.4, while exhibiting higher stability at an acidic or basic pH in the reservoir of the delivery device. Examples of a pharmaceutical agent-chemical modifier complex which may be cleaved in such a process are those with N-Mannich base linkages.

Conversion of the complex to the pharmaceutical agent may also involve a combination of both enzymatic and nonenzymatic processes.

In most cases, cleavage of the complex will occur during or shortly after transport through the skin or mucosa. However, in certain instances, cleavage is not desired until the complex reaches the pharmaceutical agent's site of action. Furthermore, in some cases, particularly with peptide and protein drugs produced via recombinant expression techniques, one may not desire cleavage of the complex. Of course, alternatively, these peptide and protein drugs can be engineered to have specific protease cleavage sites.

The invention will be more fully described and understood with reference to the following examples. These examples are provided by way of illustration only and not by way of limitation. Those skilled in the art will readily appreciate a variety of noncritical parameters which could be changed or modified to yield essentially similar results.

EXPERIMENTAL

EXAMPLE 1

Preparation of Chemical Modifiers

Preparation of D,L-4-dimethylamino-3-hydroxybutyric acid (D,L-norcarnitine)

Norcarnitine was prepared according to the procedure of Keller et al. (1963) *J. Medicinal Chem.*, 6:202. Thus, a solution of D,L-4-amino-3-hydroxybutyric acid (4.51 grams (g), 37.9 millimoles (mmol)) in water (225 milliliters (ml)) was degassed by purging with argon and then 37% aqueous formaldehyde (6.12 g) and 10% palladium-on-carbon catalyst (6.05 g) were added. The mixture was then shaken in a Parr hydrogenation apparatus under hydrogen gas at 38–40 pounds per square inch (psi) for one hour. The catalyst was removed by filtration over Celite twice with methanol rinsing. The filtrate was evaporated and the residue redissolved in methanol (30 ml) and filtered through more Celite. This filtrate was concentrated under reduced pressure. Ethyl acetate was added. The solution was then concentrated under reduced pressure to remove the last traces of methanol. The residual syrup crystallized to give 4.4 g of solid product, melting point (mp) 147°–48° C. (lit. 145°–47° C.).

EXAMPLE 2

Protection of Chemical Functionality 2.1 Preparation of O-acetyl-L-carnitine hydrochloride To a solution of L-carnitine hydrochloride (20.1 g, 101.7 mmol) in trifluoroacetic acid (28 ml) was added acetyl chloride (40 ml, 584.4 mmol). The reaction mixture was heated in an oil bath at 40°–46° C. for 20 hours and then concentrated on a rotary evaporator at 40° C. The residual viscous oil was diluted with acetone (50 ml) and concentrated to dryness again. The residue was then diluted with acetone (60 ml) and ethyl ether (180 ml) and cooled to 4° C. for one hour. The resulting precipitate was separated by filtration and triturated with boiling acetone (70 ml). After cooling to room temperature, ether (140 ml) was added and the mixture was cooled to 4° C. The solid was filtered, washed with ether and dried in a vacuum oven at 50° C. to give 18.0 g of product (75% yield, mp 188°–189° C., lit. 192°–194° C.).

2.2 Preparation of O-palmityl-L-carnitine hydrochloride

To a solution of L-carnitine hydrochloride S(8.03 g, 40.6 mmol) in trifluoroacetic acid (12 ml) was added palmitoyl chloride (27 g, 100 mmol). The oily mixture was stirred in an oil bath at 40°–46° C. overnight. The solvent was removed on the rotary evaporator and the residue was suspended in a mixture of acetone (90 ml) and ether (160 ml). The solid was then filtered and washed with ether (300 ml). The solid was further purified by twice boiling with acetone (100 ml), cooling and filtering, and finally rinsed with acetone/ether and dried in vacuo to give 15.37 g (35.3 mmol, 87% yield. mp 164°–174° C., dec. 185° C.).

2.3 Preparation of D,L-4-dimethylamino-3-hydroxybutyric acid (D,L-norcarnitine) methyl ester The methyl ester of D,L-4-dimethylamino-3-hydroxybutyric acid (D,L-norcarnitine) was prepared by treatment of a methanol solution of this acid with ethereal diazomethane. The structure was verified by NMR.

EXAMPLE 3

Activation of Chemical Functionality 3.1 Preparation of choline chloride chloroformate To a suspension of choline chloride (916 mg, 6.56 mmol) in anhydrous tetrahydrofuran (50 ml) was added a 1.93 molar (M) solution of phosgene in toluene (13 ml, 25 mmol) at room temperature. The mixture was stirred vigorously for 40 hours with protection from atmospheric moisture.

The resulting fluffy solid was filtered and rinsed with hexane and dried in vacuo to give 1.26 g (5.78 mmol, 88% yield). The infrared spectrum of the product showed strong absorption bands at 1780, 1140 and 1160 $cm^{-1}$.

3.2 Preparation of O-acetyl-L-carnitine chloride acid chloride

To a 0° C. suspension of O-acetyl-L-carnitine hydrochloride (2.4 g, 10 mmol) in dichloromethane (50 ml) containing a drop of dimethylformamide under an argon atmosphere was added oxalyl chloride (2 ml, 22.4 mmol). The ice bath was removed after five minutes and stirring was continued for an additional 75 minutes during which time a clear solution was formed. The solution was then concentrated on the rotary evaporator at 30° C. and the residue redissolved in dry dichloromethane (50 ml) and again evaporated. The resulting clear, slightly yellow solid was then dried at room temperature under high vacuum and used immediately for further reactions.

3.3 Preparation of O-palmityl-L-carnitine chloride acid chloride

O-Palmityl-L-carnitine chloride (436 mg, 1 mmol) was suspended in dichloromethane (7 ml) containing one drop of dimethylformamide and oxalyl chloride (250 microliters (μl) 2.87 mmol) was added with stirring at room temperature. The cloudy suspension became clear after 5–10 minutes and stirring was continued for one hour. The solution was concentrated under reduced pressure and the residue was dried under vacuum. The product was used immediately for further reactions.

3.4 Preparation of indomethacin acid chloride

Oxalyl chloride (220 μl, 2.5 mmol) was added to a solution of indomethacin (430 mg, 1.2 mmol) in dichloromethane (7 ml) containing one drop of dimethylformamide and the reaction mixture was stirred at room temperature for one hour. The solvent was evaporated and the solid residue was used without further purification.

3.5 Preparation of 3-benzyloxy-17β-hydroxy-estra-1,3,5(10)triene-17β-chloroformate To a solution of the 3-benzyl ether of estradiol (330 mg, 0.91 mmol) in tetrahydrofuran (20 ml) was added 5.6 ml of 1.93M solution of phosgene in toluene. The solution was stirred at room temperature for one hour and then rotary evaporated. The resulting off-white solid (377 mg) was used without further purification.

3.6 Preparation of the tin complex of digitoxin

A solution of digitoxin (765 mg, 1 mmol) and di-(n-butyl)-tin oxide (249 mg, 1 mmol) in methanol (16 ml) was heated at 70° C. for 1.5 hours and then evaporated to dryness. The residue was triturated with hexane and the hexane solution evaporated to dryness in vacuo. The product was used immediately without further purification.

EXAMPLE 4

Carbonate Linkages 4.1 Preparation of 3-digitoxigenin choline chloride carbonate ester Digitoxigenin (300 mg, 0.8 mmol) in pyridine (2.5 ml) was treated with (choline chloride) chloroformate (720 mg, 3.5 mmol) and a catalytic amount (5 mg) of 4-dimethylaminopyridine. The reaction mixture was vigorously stirred and sonicated to form a viscous paste and then stirred at 40° C. for 72 hours. The reaction mixture was diluted with dichloromethane (50 ml), filtered and the solid, mostly unreacted choline chloride, was washed with more dichloromethane (50 ml). The filtrate was evaporated to dryness and the residue heated with acetone (50 ml). The insoluble, oily material which remained after decanting the acetone, was further triturated with hot dichloromethane (2×30 ml). The dichloromethane solutions were combined and evaporated and the residue triturated with ether (2×30 ml). The remaining solid (102 mg, 0.19 mmol, 24% yield) gave a single major spot on thin-layer chromatography (silica gel, methanol/chloroform/water 3/7/0.5) and molecular mass of 504.4 ($M^+$-$Cl^-$) by FAB mass spectrometry.

4.2 Preparation of 4'''-digitoxin choline chloride carbonate ester

The tin complex of digitoxin (1.01 g) was dissolved in pyridine (2 ml) and choline chloride chloroformate (216 mg, 1.07 mmol) was added. Additional pyridine (3 ml) was added to form a gel-like suspension which was stirred overnight at about 35° C. Thin layer chromatography (TLC) (silica gel, developed first with chloroform/methanol, 9/1, and then chloroform/methanol/water, 7/3/0.5) indicated only a small amount of product had formed so an additional 160 mg (0.8 mmol) of the chloroformate was added and the mixture was stirred at room temperature for an additional two days. The reaction mixture was then filtered and the crude solid product (250 mg) was washed with dichloromethane. The combined filtrates were evaporated to give a second crop of crude product (1.0 g). The first crop was dissolved in about one ml of warm methanol and 2 ml of ether was added to precipitate a solid fraction A. Addition of another 5 ml of ether gave fraction B and further additions gave fractions C and D. Fraction C (50 mg) was the purest material but all fractions contained some residual unreacted choline chloride but no unreacted digitoxin. NMR (300 MHz) confirmed the structure of the major product and the presence of small amounts of choline chloride while mass spectrometry (FAB MS) gave a molecular ion at 894.5 ($M^+$ minus $Cl^-$). Additional fractions of similar purity were obtained from the second 1.0 g crop of solid by trituration with acetone followed by ether precipitation.

4.3 Preparation of 3-hydroxy-17β-estra-1,3,5(10)-trienyl N,N-dimethylaminoethyl carbonate ester A solution of the 3-benzyl ether 17β-chloroformate ester of 3,17β-estradiol (1.3 g, 2.8 mmol) in dichloromethane (10 ml) was added dropwise to a solution of N,N-dimethylaminoethanol (0.5 g, 5.6 mmol) in dichloromethane (10 ml) at room temperature with stirring. After one hour the solution was poured into saturated aqueous sodium bicarbonate and extracted with dichloromethane. The organic layer was dried over sodium sulfate and rotary evaporated to give 1.29 g (97% yield) of product. This material was dissolved in methanol (70 ml) and 10% palladium-on-carbon catalyst (750 mg) was added. The benzyl group was removed by stirring under a hydrogen atmosphere at room temperature for two hours. The catalyst was removed by filtration and the filtrate rotary evaporated to give 770 mg (77% yield) of desired product as confirmed by NMR.

4.4 Preparation of 2-(4-nitrophenyl)ethanol choline chloride carbonate ester

A solution of 2-(4-nitrophenyl)ethanol (125 mg, 0.75 mmol) in pyridine (92 ml) was cooled in an ice bath and solid choline chloride chloroformate (175 mg, 0.8 mmol) was added. The heterogeneous mixture was warmed to room temperature and sonicated to emulsify and stirring continued overnight. The mixture was evaporated to dryness and the residue triturated with ether and acetone. The solid was partially redissolved by chloroform (15 ml), filtered and the solvent evaporated. The residue was triturated with acetone to give the desired carbonate ester (24 mg, 9% yield). Additional material was present in the various solvent washes contaminated with choline chloride.

4.5 Preparation of 4-(4-nitrophenyl)cyclohexanol choline chloride carbonate ester Phosgene in toluene (1.93M, 11 ml, 21 mmol) was added to a solution of 4-(4-nitrophenyl)cyclohexanol (480 mg, 2.71 mmol) in tetrahydrofuran (20 ml) and the mixture stirred at room temperature for hours. Solvent was removed by evaporation to give 500 mg (81% yield) of the chloroformate derivative.

This material was added dropwise to a solution of 2-N,N-dimethylaminoethanol (317 mg, 4.2 mmol) in dichloromethane (10 ml). After stirring at room temperature for one hour the reaction mixture was washed with saturated sodium bicarbonate, dried over sodium sulfate, filtered and evaporated to give 500 mg (78% yield) of the carbonate ester.

The above material was dissolved in ether (40 ml) and methyl iodide (317 mg, 2.73 mmol) was added. After stirring overnight at room temperature the solid product was isolated by centrifugation, washed with ether and centrifuged again to give 621 mg (87% yield) of the desired choline carbonate derivative.

4.6 Preparation of cisapride carbonates

To a solution of butyric acid (1.76 g, 20 mmol) in dichloromethane (35 ml) was added tetrabutylammonium sulfate (680 mg, 2 mmol) and potassium bicarbonate (8.2 g) in water. To this solution was then added a solution of chloromethyl chlorosulfate (3.63 g) in dichloromethane (5 ml). The mixture was stirred at room temperature for one hour and the aqueous layer was extracted with dichloromethane (30 ml). The dichloromethane solutions were combined, dried (sodium sulfate), and concentrated in vacuo to yield crude chloromethyl butyrate (2.8 mg) which was purified by column chromatography (10.62 mmol, 53.1%).

To a solution of chloromethyl butyrate (920 mg, 5.9 mmol) in acetone (40 ml) was added sodium iodide (3.09 g). The mixture was stirred for 3 hours, concentrated invacuo, and dissolved in dichloromethane (50 ml). This solution was washed with saturated aqueous sodium chloride, aqueous sodium thiosulfate, and saturated aqueous sodium chloride, dried (sodium sulfate) and concentrated invacuo to yield iodomethyl butyrate (80%).

To a solution of cisapride (140 mg, 0.3 mmol) in acetonitrile (6 ml) was added iodomethyl butyrate (87 mg, 0.38 mmol). The reaction mixture was stirred at room temperature for 3 hours and then concentrated in vacuo. The residue was triturated with acetonitrile/ether to ield the crude ether (90%).

By following the procedures set forth above and substituting chloromethyl dodecanoate for chloromethyl butyrate, the corresponding ether was produced.

4.7 Preparation of methotrexate-bis-(4-trimethylammoniobutyroyloxymethyl ester), diiodide salt To a solution of methotrexate (364 mg, 0.8 mmol) in DMF (9 ml) was added cerium carbonate (521.3 mg, 1.6 mmol) and a mixture of 85:15 iodomethyl 4-iodobutyrate: iodomethyl 4-chlorobutyrate (630 mg, 1.85 mmol). The reaction was stirred at room tmperature until complete and concentrated in vacuo. The crude diester was purified by flash chromatography to yield the desired diester.

To a solution of the methotrexate diester prepared above (57 mg, 0.065 mol) in acetonitrile (6 ml) was added a solution of trimethylamine (1.5 ml, 1.25M in acetonitrile). The reaction mixture was stirred at room temperature for five hours and diluted with acetonitrile (5 ml). An additional aliquot of trimethylamine (2 ml, 1.25M in acetonitrile) was added and the reaction mixture was stirred at room temperature overnight. The mixture was concentrated in vacuo, and triturated with ether to yield the desired bis salt.

EXAMPLE 5

Carbamate Linkages 5.1 Preparation of 2-(4-nitrophenyl)ethylamine choline chloride carbamate A solution of 2-(4-nitrophenyl)ethylamine (245 mg, 1.5 mmol) and diisopropylethylamine in dimethylformamide (1 ml) was cooled in an ice bath and choline chloride chloroformate (322 mg, 1.6 mmol) was added. The reaction mixture was warmed to room temperature, diluted with dichloromethane (7 ml) and stirred overnight. An additional 23 ml of dichloromethane was added and the suspension centrifuged to isolate the solid product. This material was washed with dichloromethane and ether to give the desired product (351 mg, 71% yield).

5.2. Preparation of cisapride carbamates

A mixture of choline (2.235 mg, 16 mmol) and phosgene (32 ml, 1.93M in toluene) in THF (90 ml) was stirred at room temperature for 72 hours. The precipitate was filtered, washed with hexane, and dried in vacuo to yield choline chloride chloroformate (3.0 g).

To a solution of cisapride (2 mg, 0.2 mmol) in anhydrouse DMF (2 ml) was added pyridine (48 mg, 0.6 mmol) and choline chloride chloroformate (110 mg, 0.55 mmol). The mixture was stirred at room temperature for 4 hours and then additional pyridine (32 mg) and choline chloride chloroformate (66 mg) were added. The mixture was stirred for an additional 4 hours. Additional pyridine (50 mg) and choline chloride chloroformate (80 mg) were added and the mixture was stirred at room temperature overnight. The mixture was diluted with dichloromethane (50 ml) and filtered. The filtrate was concentrated to yield a viscous oil which was triturated to yield the crude carbamate salt (240 mg). The crude oil was dissolved in 3% methanol in dichloromethane and was purified by column chromatography (silanized column, 300 ml 25% methanol in dichloromethane, then 4% methanol in dichloromethane) to yield the pure carbamate (98 mg, 77.6%).

5.3 Preparation of deprenyl-N-(morpholine-N-carbonyloxymethyl), iodide salt

To a −78° C. solution of morpholine (4.05 g, 0.046 mol) in dichloromethane (20 ml) was added chloromethyl chloroformate (3 g, 0.023 mol). The reaction mixture was allowed to warm to room temperature and was then diluted with ice water. The dichloromethane layer was separated, dried (sodium sulfate), and concentrated in vacuo to yield the desired carbamate (4.16 g).

To a solution of the carbamate prepared above (4.16 g,, 0.023 mol) in acetone (40 ml) was added sodium iodide (10.3 g, 0.069 mol). The mixture was refluxed for 2 hours, cooled, diluted with dichloromethane, washed with saturated aqueous sodium chloride, aqueous sodium thiosulfate (5%), and saturated aqueous sodium chloride, dried (sodium sulfate) and concentrated invacuo to yield the desired iodo carbamate (1.32 g) which was used without further purification.

To a solution of deprenyl hydrochloride (146 mg, 0.654 mmol) in acetonitrile (10 ml) was added the iodo carbamate prepared above (180 mg, 0.654 mmol). The reaction mixture was stirred at 40° C. for 12 hours and then concentrated in vacuo. Trituration with ether and 10% dichlormethane in hexane yielded the pure salt (260 mg, 87%).

EXAMPLE 6

Ester Linkages 6.1 Preparation Of digitoxigenin-3-(O-acetyl-L-carnitine) ester

A solution of digitoxigenin (300 mg, 0.8 mmol) in dichloromethane (7 ml) was treated with a dichloromethane solution (7 ml) of freshly prepared O-acetyl-carnitine chloride acid chloride (1 mmol) at room temperature. The reaction mixture was kept under an argon atmosphere and was evacuated every five minutes by means of an aspirator in order to remove the evolved hydrogen chloride gas. This process was required to prevent dehydration of digitoxigenin to the 14-anhydro compound. The reaction mixture was stirred at room temperature for 4.5 hours while maintaining a total volume of 3–5 ml by replacement of dichloromethane lost to evaporation during the evacuation procedure. The solvent was then removed in vacuo and the residue was triturated with dry dichloromethane (10 ml). The insoluble portion was mostly O-acetyl-L-carnitine. The filtrate was evaporated to dryness and the solid residue washed with acetone/ether (1 ml/5 ml). The remaining solid was heated with acetonitrile (3.5 ml) and centrifuged to remove a small amount (55 mg) of a solid composed of a mixture of the O-acetyl-L-carnitine and the desired product. The supernatant was treated with ether to precipitate the product (200 mg) whose structure was confirmed by NMR.

6.2 Preparation of 3-hydroxy-17β-(O-acetyl-L-carnitinate) estra-1,3,5(10)triene ester O-Acetyl-L-carnitine chloride acid chloride, prepared from 2.4 g (10 mmol) of O-acetyl-L-carnitine hydrochloride, was dissolved in dry dichloromethane (50 ml) and estradiol (2.72 g, 10 mmol) was added as a solid. The solid appeared to dissolve slowly at first while at the same time being replaced by an oily, milky upper layer in the stirred mixture. Stirring was continued at room temperature for 66 hours during which time the oily layer was replaced by a fine white solid. The solid was removed by filtration and washed with dichloromethane (50 ml). Evaporation of the filtrate and the wash gave a total of 370 mg of gummy residue which TLC (silica gel, ethanol/chloroform/water 10/5/5) indicated to be a mixture of starting estradiol ($R_f$ 0.9) and product ($R_f$ 0.7). The solid was likewise found to contain unreacted estradiol which was removed by trituration with refluxing ethyl acetate (2×50 ml). The NMR of the resulting white solid (3.6 g, 78% yield) agreed with the expected product.

6.3 Preparation of digitoxigenin-3-(O-palmityl-L-carnitine chloride) ester

O-Palmityl-L-carnitine chloride acid chloride (prepared from 436 mg, 1 mmol of O-palmityl-L-carnitine chloride) was dissolved in dichloromethane (7 ml) and added to a solution/suspension of digitoxigenin (311 mg, 0.83 mmol) in dichloromethane (7 ml) to give a clear solution. The hydrogen chloride gas evolved was removed by evacuation every 15–20 minutes over the next five hours during which time the reaction went almost to completion with only a trace of the anhydro compound being formed. The mixture was diluted with dichloromethane (20 ml) and filtered to give 122 mg colorless solid. The filtrate was rotary evaporated, the residue redissolved in acetone (1 ml) and reprecipitated by addition of ether (14 ml) to give an oil. The oil was triturated with ether (3×10 ml), redissolved in acetonitrile (1 ml) and reprecipitated and triturated twice more with ether to give solid product (416 mg) which was shown to be mainly desired compound with a trace of unreacted digitoxigenin by TLC (silica gel, first elution with chloroform/methanol 10/1, second elution with chloroform/methanol/water 7/3/0.5).

6.4 Preparation of indomethacinyl N,N-dimethylaminoethyl ester

A solution of indomethacin acid chloride (prepared from 430 mg, 1.2 mmol indomethacin) in dichloromethane (3 ml) was added to a solution of N,N-dimethylaminoethanol (342 mg, 3.8 mmol) in dichloromethane (10 ml) and the mixture stirred at room temperature for 30 minutes. The solution was diluted with dichloromethane (20 ml), washed with water (3×10 ml), dried over sodium sulfate and filtered. Evaporation of the solvent gave a quantitative yield (520 mg) of the dimethylaminoethyl ester as an oil.

6.5 Preparation of 3-O-(indomethacinoyl)-D,L-norcarnitine methyl ester

Indomethacin acid chloride (430 mg, 1.2 mmol) was dissolved in chloroform (3 ml) and added to a solution of D,L-norcarnitine methyl ester (363 mg, 2.5 mmol) in chloroform (3 ml) at 0° C. with stirring. The ice bath was then removed and stirring continued at room temperature for 2 hours. The reaction mixture was diluted with chloroform and extracted with saturated sodium bicarbonate. The chloroform layer was dried over sodium sulfate, filtered and rotary evaporated to give an oil which was purified by column chromatography on alumina (grade III, elution with 2.5% methanol in chloroform). Fractions containing the desired product were identified by TLC and NMR and combined (total 610 mg).

6.6 Preparation of 2-(4-nitrophenyl)ethanol O-acetyl-L-carnitine ester

A solution of O-acetyl-L-carnitine acid chloride salt, (prepared from 240 mg, 1 mmol, of O-acetyl-L-carnitine chloride) in dichloromethane (6 ml) was added to a solution of 4-nitrophenethyl alcohol 190 mg, 1.14 mmol) in dichloromethane and stirred overnight at room temperature. The solution was evaporated to give an oily residue which was triturated with ether (3×30 ml). The oil was then redissolved in acetonitrile and precipitated by addition of toluene. The precipitate was redissolved in isopropyl alcohol and again precipitated using ether/hexane to give the final product (200 mg, 51% yield).

6.7 Preparation of 3,17β-estradiol 17β-betaine ester

Betaine hydrochloride (282 mg, 1.8 mmol) was suspended in dichloromethane (15 ml) containing a drop of dimethylformamide and oxalyl chloride (157 µl, 1.8 mmol) was added. After stirring at room temperature overnight the fine suspension was evaporated to dryness. The solid was resuspended in dichloromethane (10 ml) and a solution of 3,17β-estradiol (500 mg, 1.8 mmol) in ethyl acetate (10 ml) was added and the mixture stirred overnight at room temperature. The solvents were then removed by evaporation and the residue triturated with ether to give 452 mg (62% yield) of the betaine ester.

6.8 Preparation of 5-fluorouracil-1-(4-trimethylaminobutyroyloxymethyl), chloride salt A suspension of paraformaldehyde (2.492 g, 83 mmol) and 4-chlorobutyryl chloride (11.28 g, 80 mmol) was stirred at 85° C. for 90 minutes. Additional paraformaldehyde (1.65 g) was added and the reaction was heated at 85° C. for an additional 90 minutes. Additional paraformaldehyde (0.74 g) was added and the reaction was heated at 85° C. for 30 minutes. The reaction mixture was then diluted with chloroform (70 ml) and stirred with saturated aqueous sodium bicarbonate (50 ml). The chloroform solution was dried over sodium sulfate and concentrated in vacuo. Vacuum distillation (46°–56° C. at 0.1 mm) yielded the desired 4-chlorobutyryl chloromethyl ester (1.682 g) which could be further purified by column chromatography (flash silica, eluting with ether:hexane 4:6, 500 ml). The NMR of the resulting oil agreed with the expected product.

A solution of 5-fluorouracil (325.2 mg, 2.5 mmol) and DIEA (517 mg, 4 mmol) in DMA (N,N-dimethylacetamide) was treated with 4-chlorobutyryl chloromethyl ester (500 mg, 2.92 mmol). The reaction mixture was stirred at room temperature overnight and was then concentrated in vacuo. The residue was diluted with chloroform (100 ml), washed with saturated aqueous sodium chloride, 105 aqueous citric acid, and saturated aqueous sodium chloride, dried over sodium sulfate, and concentrated in vacuo. Column chromatography (flash silica, eluting with ethyl acetate:dichloromethane, 1:7, 400 ml and then 1:5) yielded the monoester (360 mg, 55% yield) which had a molecular mass of 265.1 by FAB mass spectroscopy.

The monoester prepared above (150 mg) was treated with a solution of trimethylamine in acetonitrile (1.43M, 10 ml). The reaction mixture was stirred on a warm hot plate for 76 hours and was then concentrated in vacuo. The residue was triturated in ether and the solid precipitate was centrifuged, dissolved in methanol:dichloromethane (1:8, 4 ml) and precipitated with ether to yield the desired trimethylammonium salt (114 mg) which had a molecular mass of 288.14 ($M^+$ minus $Cl^-$) by FAB mass spectroscopy.

6.9 Preparation of lorazepam-3-(O-acetylcarnitine) ester chloride salt

L-Carnitine-O-acetate (618 mg) was subjected to vacuum to remove any acetic acid and was then suspended in dichloromethane (15 ml) and DMF (1 drop). To this suspension was added oxalyl chloride (450 µl, 5.1 mmol). The reaction was stirred under argon for one hour, concentrated in vacuo, and then dissolved in dichloromethane (12.5 ml) to yield the acyl chloride which was used without further purification.

A solution of lorazepam (321 mg, 1 mmol) and pyridine (160 mg, 2 mmol) in dichloromethane (10 ml) was cooled to 0° C. To this solution was added a solution of the acyl chloride prepared above (6.5 ml, about 1.3 mmol). The ice bath was removed and the reaction mixture was stirred at room temperature for 90 minutes. Additional acyl chloride (2 ml) was added and the reaction was stirred for an additional hour. Pyridine (56 mg) and additional acyl chloride (0.3 mmol) was added and the reaction was stirred at room temperature until the reaction was complete by TLC. The reaction mixture was concentrated in vacuo and the residue was triturated with ether. The residue was passed through two silanized silica gel columns (eluting with 3% methanol in dichloromethane) and was then dissolved in dichloromethane (10 ml) and filtered. Column chromatography (eluting with dichloromethane (600 ml), followed by 1% methanol in dichloromethane (300 ml), 2% methanol in dichloromethane (300 ml), and 3% methanol in dichloromethane (200 ml) yielded the desired trimethylammonium salt (228 mg), a portion of which was dissolved in dichloromethane (3 ml) and precipitated with ether. The NMR and mass spectra of the salt agreed with those of the expected product.

6.10 Preparation of a charged morphine adduct

To a suspension of morphine sulfate (275 mg, 0.362 mmol) in DMF (4 ml) was added potassium carbonate (284 mg, 2.06 mmol), followed by t-BOC-$N_3$ (78 mg, 0.542 mmol). The slurry was stirred at room temperature for 96 hours and filtered (washing with dichloromethane). The filtrate was concentrated in vacuo. The residue was dissolved in ether, washed with water, 1% aqueous citric acid, 0.1N aqueous sodium hydroxide, and water, dried over sodium sulfate, and concentrated in vacuo. The combined aqueous washes were extracted with dichloromethane and the extracts were dried over sodium sulfate, and concentrated in vacuo. The residues were combined and chromatographed (flash silica, eluting with 10% methanol in dichloromethane) to yield the desired carbonate (210 mg, 86% yield).

To a solution of the carbonate prepared above (100 mg, 0.15 mmol) in dichloromethane (10 ml) was added DCC (140 mg, 6.75 mmol), followed by 4-chlorobutanoic acid (18.4 mg, 0.15 mmol) and DMAP (5 mg). The reaction was stirred for 24 hours and additional DCC (140 mg) and DMAP (5 mg) was added. The reaction was stirred for another 24 hours and filtered. The filtrate was concentrated in vacuo and the residue was chromatographed (flash silica, eluting with 10% methanol in dichloromethane) to give the desired chloro ester (80 mg, 70% yield).

To a solution of the chloro ester prepared above (80 mg, 0.103 mmol) in anhydrous acetonitrile ( 1 ml) was added a solution of trimethylamine in acetonitrile (1.5 ml, 2.1M, 3.1 mmol). The reaction was stirred at 30° C. for 72 hours, however, TLC indicated little product formation. The reaction was concentrated in vacuo. The residue was diluted with a solution of trimethylamine in ethanol (3 ml, 4.3M) and heated at 80° C. for 3 hours. The reaction mixture was concentrated in vacuo. The residue was dissolved in ethanol (2 ml) and added dropwise to ether (30 ml). The cloudy solution was centrifuged and the residue was triturated with ether. Column chromatography (RP2-silanized silica, eluting with 5% methanol in dichloromethane) yielded the desired trimethylammonium salt (15 mg, 25% yield) whose structure was verified by NMR.

To the trimethylammonium salt prepared above (15 mg, 0.026 mmol) was added a solution of acetic acid which had been saturated with hydrochloric acid (1 ml). The reaction mixture was stirred for 5 minutes at room temperature and then concentrated in vacuo to give a light yellow residue. The residue was precipitated with 10% methanol in ether and triturated with ether to yield the desired bis quaternary ammonium salt (8 mg, 67% yield) whose structure was verified by NMR.

6.11 Preparation of digoxin-4'''-[(O-acetyl)-betonicine ester], chloride salt

To a suspension of betonicine (3 g, 22.9 mmol) in methanol (30 ml) was added O-methyl-N,N'-diisopropylisourea (14.49 g, 91.5 mmol). The reaction was stirred at room temperature for 3 days and was then diluted with water (60 ml) and placed in the freezer for 10 minutes. The reaction mixture was filtered and the white solid was dissolved in hot ethanol. Acetone was added until the solution became cloudy. The solution was placed at 0° C. for 3 days and the precipitate was collected by filtration. The quaternary ammonium salt (3.15 g, 86% yield, mp 245°–248° C.) was identified by NMR.

To a solution of the salt prepared above (823 mg, 5.17 mmol) in TFA (5 ml) was added acetyl chloride (1.11 mg, 20.68 mmol). The reaction mixture was heated to 40°–46° C. and stirred under a drying tube overnight. The reaction mixture was cooled to room temperature. The resulting yellow oil was dissolved in acetone (50 ml) and concentrated in vacuo. The residue was dissolved in toluene (25 ml), concentrated in vacuo, dissolved in ethanol (25 ml), and concentrated in vacuo to yield the crude ester (1.56 g, 96% yield) which could be further purified by trituration with ether.

To a suspension of the ester prepared above (500 mg, 1.59 mmol) in anhydrous dichloromethane (5 ml) was slowly added oxalyl chloride (1.01 g, 7.93 mmol). The reaction mixture was stirred for an hour and was then concentrated in vacuo. The resultant acyl chloride was used without further purification.

DIEA (514 mg, 3.98 mmol) and the tin complex of digoxin (supra, 2.10 g, 2.12 mmol) were dissolved in DMF (10 ml). The reaction mixture was diluted with dichloromethane (10 ml). The acyl chloride prepared above (1.59 mmol) and DIEA (5 eq) were dissolved in dichloromethane (5 ml), stirred for 90 minutes, and then concentrated in vacuo. The residue was diluted with dichloromethane (20 ml) and then added to the mixture containing the tin complex which had been chilled to 0° C. The reaction mixture was warmed to room temperature and concentrated in vacuo. The residue was diluted in methanol/dichloromethane and precipitated from ether. The crude product was dissolved in methanol (20 ml). Water (5 ml) was then added. The mixture was left undisturbed for two days and then filtered. The filtrate was concentrated in vacuo to yield a white solid which was purified by column chromatography (flash silica, 20 mg, mp 195°–198° C.). The structure was verified by NMR.

6.12 Preparation of digoxin-12-stachydrine ester-3''',4'''-cyclic carbonate, chloride salt Stachydrine was prepared following the procedure set forth in Rappoport et al. (1977) *J. Org. Chem.* 42:139. To a solution of L-proline (5 g, 43.4 mmol) in methanol (50 ml) was added O-methyl-N,N'-diisopropylisourea (22.89 g, 144.7 mmol). The reaction mixture was stirred for 2 days, diluted with water (100 ml), filtered, and concentrated in vacuo. The residue was dissolved in hot ethanol (50 ml). To this solution was then added isopropyl alcohol (25 ml) and ether (30 ml). The solution was stored in the freezer overnight and was then filtered. The precipitate was washed with ether and dried in a vacuum oven at 60° C. to yield stachydrine (5.66 g, 91%, mp 115°–118° C.) whose structure was verified by NMR.

To a 0° C. suspension of stachydrine (1 g, 6.98 mmol) in dichloromethane (10 ml) and DMF (3 drops) was added oxalyl chloride (3.55 g 27.9 mmol). The reaction was stirred for 90 minutes and then concentrated in vacuo to yield the corresponding acyl chloride which was used immediately without further purification.

To a solution of the tin complex of digoxin (supra, 3 g, 2.96 mmol) in DMF (10 ml) and dichloromethane (10 ml) was added DIEA (766 mg, 5.93 mmol). The reaction mixture was cooled to 0° C. To the reaction mixture was then added a solution of 4-nitrophenyl chloroformate (777 mg, 3.96 mmol) in dichloromethane (2 ml). The reaction was stirred for 2 hours and then filtered. The reaction mixture was extracted with ethyl acetate (2×100 ml), washed with saturated aqueous sodium chloride, saturated aqueous sodium bicarbonate, and saturated aqueous sodium chloride, dried over magnesium sulfate, and concentrated in vacuo to yield a yellow solid. The solid was dissolved in dichloromethane and methanol. Ethyl acetate and ether was added and the solution was placed in the freezer. The mixture was filtered and washed with ether. The filtrate was concentrated in vacuo and the residue was diluted with hot ethyl acetate and filtered. The residues were combined, concentrated in vacuo, and triturated with hot ethyl acetate to yield the desired cyclic carbonate (2.39 g, 77% yield).

To a 0° C. solution of the cyclic carbonate (407 mg, 0.505 mmol) in dichloromethane was added the acyl chloride derivative of stachydrine prepared above (200 mg, 1.01 mmol). The reaction was stirred for 2 hours and concentrated in vacuo to yield a yellow foam. The residue was dissolved in methanol and dichloromethane, precipitated with ether, and dried in vacuo to yield the desired product (414 mg) with some dehydration of the 14-hydroxyl group.

6.13 Preparation of digoxin-12-nicotinate ester-3''',4'''-cyclic carbonate

To a 0° C. suspension of nicotinic acid (2 g, 16.2 mmol) in dichloromethane and DMF (2 drops) was added oxalyl chloride (8.25 g, 65 mmol). The ice bath was removed and the reaction mixture was stirred for 2 hours, filtered, washed with dichloromethane, dried, and concentrated in vacuo to yield the desired acyl chloride which was used immediately without further purification.

To a 0° C. solution of the tin complex of digoxin (supra, 400 mg, 0.496 mmol) in dichloromethane (10 ml) was added DIEA (166.5 mg, 1.29 mmol). To the reaction mixture was added a solution of the acyl chloride prepared above (115 mg, 0.644 mmol) in dichloromethane/DMF/acetonitrile. The reaction mixture was stirred overnight. Additional acyl chloride (54 mg), DIEA (0.9 mmol) and DMAP (121 mg, 0.992 mmol). The reaction was stirred overnight. Additional DIEA (224 μl) and DMAP (121 mg) was added and reaction mixture was cooled to 0° C. Additional acyl chloride (0.7 eq) was added. The reaction mixture was stirred overnight, washed with saturated aqueous sodium chloride, saturated aqueous sodium bicarbonate, and saturated aqueous sodium chloride, dried over magnesium sulfate, and concentrated in vacuo to yield a brown solid. The solid was dissolved in dichloromethane, precipitated from ether, and dried in vacuo to yield the desired ester (279 mg, 62% yield) whose structure was verified by NMR.

6.14 Preparation of theophylline-7-(N,N,N,-trimethylglycyloxymethyl), iodide salt The following procedure is based on the method set forth in Bodor et al. (1982) *Int. J. Pharma.* 12:299.

A mixture of triethylamine (26 g, 0.145 mmol) and formaldehyde (26 g, 24 ml) was stirred for one hour and filtered. The solid white mass was washed with THF, filtered, and dried in vacuo. The solid was added to a mixture of theophylline (14.69 g, 0.145 mmol) and triethylamine (15 ml). The reaction mixture was diluted with THF (250 ml) to mostly suspend the solid. The reaction mixture was stirred overnight and filtered. The solid was washed with ether and dried in vacuo at 70° C. to yield the desired alcohol (25 g, 82% yield).

To a mixture of N,N-dimethylglycine (3 g, 29.9 mmol), the alcohol prepared above (6.12 g, 29.9 mmol), and DCC (6.17 g, 29.9 mmol) was added pyridine (30 ml). The reaction mixture was stirred for 40 hours, diluted with dichloromethane (200 ml), filtered, and concentrated in vacuo. The solid was dissolved in dichloromethane (30 ml), filtered, washed with dichloromethane, diluted with ether, and concentrated in vacuo to yield a white solid (5.65 g, 65% yield). NMR analysis indicated that the reaction had only proceeded to 50% conversion. Additional N,N-dimethylglycine (1.5 g), theophylline (3 g), and DCC was added and the reaction was allowed to stir overnight. The mixture was then concentrated in vacuo, diluted with dichloromethane, filtered, washed with saturated aqueous sodium chloride, saturated aqueous sodium bicarbonate, and saturated aqueous sodium chloride, dried over magnesium sulfate, and concentrated in vacuo. The residue was crystallized from hot isopropanol to yield the desired ester (2.48 g, 29%) whose structure was verified by MS and NMR.

To a mixture of the above ester (500 mg, 1.72 mmol) in acetonitrile (15 ml) was added iodomethane (489 mg, 214 μl, 3.94 mmol). The reaction mixture was stirred for 5 minutes and then allowed to sit for two days. The mixture was then filtered, washed with dichloromethane, and concentrated in vacuo to yield the desired trimethylammonium salt (600 mg, mp 219–220) whose structure was verified by NMR and MS.

6.15 Preparation of haloperidol (D,L)-choline carbonate, bromide salt

To a 0° C. solution of haloperidol (751.76 mg, 2 mmol) in dichloromethane (18 mL) was added pyridine (240 mg, 3 mmol) and 2-bromoethyl chloroformate (520 mg, 90% Aldrich Tech. Grade, ca. 2.6 mmol). The reaction was stirred at 0° C. for one hour and at room temperature for 30 minutes. The reaction mixture was diluted with dichloromethane (30 ml) and washed with saturated aqueous sodium chloride. The pH of the aqueous layer was adjusted to 7.2 with saturated aqueous sodium bicarbonate and the aqueous layer was extracted with dichloromethane (40 ml). This procedure was repeated. The extracts were combined and concentrated in vacuo to yield crude carbonate (1.2 g) which was purified by column chromatography (eluting with 2% methanol in dichloromethane) to yield the pure carbonate (830 mg, 80.3% yield.)

A solution of the carbonate prepared above (810 mg, 1.54 mmol) in acetonitrile (10 ml) was trated with trimethylamine (1.44M in acetonitrile, 31.7 mmol) and was stirred overnight at room temperature. The reaction mixture was concentrated in vacuo to yield the crude salt (840 mg) which was dissolved in dichloromethane:methanol 10:1 and precipitated with ether. The viscous solid was triturated with ether and centrifuged to yield the pure salt (780 mg, 1.33 mmol, 86.4%).

Following the procedure set forth above and substituting 4-bromobutyryl chloride for 2-bromoethyl chloroformate, the corresponding carbonate ester was produced.

6.16 Preparation of other haloperidol esters

To a solution of haloperidol (370 mg, 0.984 mmol) in acetonitrile (15 ml) and dichloromethane (10 ml) was added iodomethyl butyrate (250 mg). The reaction mixture was stirred at room temperature for one hour and at 4° C. for 2 days. The mixture was concentrated invacuo and triturated with hexane to yield the crude salt which was crystallized in acetonitrile/ether to yield the pure salt (455 mg, 76.5% yield).

6.17 Preparation of bumetanide esters

To a solution of bumetanide (100 mg, 0.274 mmol) and 2-bromoethanol (1 ml) was added HCl gas for 3 minutes. The reaction vessel was sealed and left unstirred for 72 hours at room temperatre. The mixture was diluted with dichloromethane (20 ml), washed with saturated aqueous sodium bicarbonate and water, dried (sodium sulfate0 and concentrated in vacuo to yield the corresponding ester (78 mg, 60%) which was used without further purification.

To a solution of the ester prepared above (90 mg, 0.191 mmol) in N,N-dimethylformamide (1 ml) was added a solution of trimethylamine (300 mg) in acetonitrile (1 ml). The mixture was stirred for 12 hours at room temperature and then concentrated in vacuo. The residue was dissolved in methanol and the resulting solution was added dropwise to ether (20 ml). The resulting milky white solution was centrifuged and the resulting pellet was triturated with ether and dried in vacuo to yield the pure salt (91 mg, 90%).

6.18 Preparation of progesterone-3-(4-N,N,N-trimethylammoniobutyrate) enol ester, bromide salt A mixture of 4-chlorobutyric acid (12.3 g, 0.1 mol) and acetic anhydride (11 g, 0.11 mol) in benzene (50 ml) was refluxed for 6 hours and then cooled to room temperature and concentrated in vacuo. The residue was distilled to yield the pure anhydride (10.5 g, 46%).

A mixture of progesterone (1 g, 3.2 mmol), the anhydride prepared above (1.44 g, 6.4 mmol), p-toluenesulfonic acid (100 mg) in benzene (10 ml) was heated at 90° C. for 30 minutes. The mixture was cooled to room temperature, diluted with ethyl acetate, washed with saturated aqueous sodium bicarbonate, dried (sodium sulfate), and concentrated invacuo. The residue was purified by column chromatography (1% ethyl acetate in dichloromethane) to yield the pure ester (800 mg, 60%).

To a solution of the ester prepared above (800 mg, 1.91 mmol) in acetonitrile (2 ml) was added a solution of triethylamine (3 g) in acetonitrile (10 ml) and then sodium iodide (29 mg). The reaction mixture was stirred for 12 hours at room temperature and then concentrated in vacuo. The residue was dissolved in methanol (1 ml) and this solution was added dropwise to ether (20 ml). The mixture was centrifuged and the pellet was dried n vacuo to yield the crude salt (447 mg).

By following the procedure set forth above and substituting bromoacetic anhydride for 4-chlorobutyric anhydride, the corresponding salt was produced.

6.19 Preparation of deprenyl-N-ethoxycarbonyloxymethyl, iodide salt

To a solution of ethanol (360 mg, 0.808 mol) in dichloromethane (10 ml) was added diisopropylethylamine (1 g, 0.008 mol). The mixture was cooled to 0° C. and chloromethyl chloroformate (1 g, 0.008 mol) was added in a dropwise fashion. The mixture was stirred for one hour at room temperature and then was poured into water and separated. The organic layer was washed with aqueous hydrochloric acid (0.1N) and saturated aqueous sodium bicarbonate, dried (sodium sulfate), and concentrated in vacuo. Pure chloromethyl ethyl carbonate (500 mg) was obtained by distillation.

To a solution of deprenyl (424 mg, 2.3 mmol) in acetonitrile (5 ml) was added chloromethyl ethyl carbonate (315 mg, 2.3 mmol) and sodium iodide (340 mg, 2.3 mmol). The reaction mixture was stirred at 40° C. for 12 hours and then concentrated in vacuo. Trituration with 10% methanol in ethanol yielded the pure salt (712 mg).

6.20 Preparation of deprenyl-N-octyloxycarbonyloxymethyl, iodide salt

To a solution of octanol (1.0 g, 0.008 mol) in dichloromethane (30 ml) was added diisopropylethylamine (1 g, 0.008 mol). The mixture was cooled to 0° C. and chloromethyl chloroformate (1 g, 0.008 mol) was added in a dropwise fashion. The mixture was stirred for one hour at room temperature and then was poured into water and separated. The organic layer was washed with aqueous hydrochloric acid (0.1N) and saturated aqueous sodium bicarbonate, dried (sodium sulfate), and concentrated in vacuo. to yield the desired chloromethyl octyl carbonate (1.69 g) which was used without further purification.

To a solution of chloromethyl octyl carbonate (1.14 g, 0.005 mol) in acetone (10 ml) was added sodium iodide (2.3 g, 0.015 mol). The mixture was stirred for 3 hours, concentrated invacuo, and dissolved in dichloromethane (50 ml). This solution was washed with saturated aqueous sodium chloride, aqueous sodium thiosulfate, and saturated aqueous sodium chloride, dried (sodium sulfate) and concentrated invacuo to yield iodomethyl octyl carbonate (1.14 g).

To a solution of deprenyl (170 mg, 0.91 mmol) in acetonitrile (5 ml) was added iodomethyl octyl carbonate (290 mg, 0.91 mmol). The reaction mixture was stirred at 40° C. for 12 hours and then concentrated in vacuo. Trituration with ether and 10% dichlormethane in hexane yielded the pure salt (350 mg, 77%).

6.21 Preparation of deprenyl-N-butyroyloxymethyl, iodide salt

To a solution of butyric acid (3 g, 0.034 mol) in dichloromethane (34 ml) was added sodium bicarbonate (11 g, 0.13 mol), tetrabutylammonium hydrogen sulfate (1.15 g, 0.0034 mol) and water (34 ml). With rapid stirring, chloromethyl chlorosulfate (ClCH$_2$SO$_3$Cl, 6.4 g, 0.04 mol) was added. The mixture was stirred for one hour, diluted with dichloromethane (20 ml), washed with water, dried (sodium sulfate), and concentrated in vacuo to yield chloromethyl butyrate (2.1 g, 41%) which was purified by distillation.

To a solution of chloromethyl butyrate (1.9 g, 0.014 mol) in acetone (15 ml) was added sodium iodide (6.3 g, 0.041 mol). The mixture was refluxed for 2 hours, cooled, diluted with dichloromethane, washed with saturated aqueous sodium chloride, aqueous sodium thiosulfate (5%), and saturated aqueous sodium chloride, dried (sodium sulfate) and concentrated invacuo to yield iodomethyl butyrate (3.2 g).

To a solution of deprenyl (139 mg, 0.743 mmol) in acetonitrile (5 ml) was added iodomethyl butyrate (169 mg, 0.743 mmol). The reaction mixture was stirred at 40° C. for 12 hours and then concentrated in vacuo. Trituration with ether and 10% dichlormethane in hexane yielded the pure salt (300 mg).

6.22 Preparation of deprenyl-N-pivaloyloxymethyl, iodide salt

To a solution of deprenyl (240 mg, 1.28 mmol) in acetonitrile (5 ml) was added chloromethyl 2,2-dimethylpropionate (193 mg, 1.28 mmol) and sodium iodide (192 mg, 1.28 mmol). The reaction mixture was stirred at 40° C. for 12 hours and then concentrated in vacuo. Trituration with ether and 10% dichlormethane in hexane yielded the pure salt (390 mg, 71%).

6.23 Preparation of deprenyl-N-acetoxymethyl, bromide salt

To a solution of deprenyl (100 mg, 0.654 mmol) in acetonitrile (5 ml) was added bromomethyl acetate (146 mg, 0.654 mmol). The reaction mixture was stirred at 40° C. for 12 hours and then concentrated in vacuo. Trituration with ether and 10% dichlormethane in hexane yielded the pure salt (210 mg, 94%).

EXAMPLE 7

Drug-Spacer-Chemical Modifier Complexes 7.1 Preparation of 3-hydroxy-17β-estra-1,3,5(10)-trienyl-6-(O-acetyl-L-carnitinamido)hexyl carbonate The 3-benzyl ether 17β-chloroformate ester of estradiol (297 mg, 0.7 mmol) was added to a solution of N-t-BOC-6-aminohexanol (138 mg, 0.64 mmol) in pyridine (6 ml) at 0° C. After stirring at this temperature for three hours, the solution was diluted with dichloromethane and washed with water and with 0.1N HCl. The organic layer was then dried over sodium sulfate, filtered and evaporated to give, after further purification by column chromatography (silica gel, 10% ethyl acetate in dichloromethane), 240 mg (57% yield) of the desired product).

To a solution of the above t-BOC protected amine (240 mg, 0.4 mmol) in dichloromethane (5 ml) was added trifluoroacetic acid (5 ml). After stirring at room temperature for one hour the solution was rotary evaporated to give an oily product. The material was redissolved in dichloromethane and the solution washed with saturated sodium bicarbonate. The organic layer was dried over sodium sulfate, filtered and the filtrate rotary evaporated to give a yellow oil. This material was dissolved in dichloromethane (5 ml) and triethylamine (80 mg, 0.8 mmol) was added. After cooling to 0° C., a solution of O-acetyl-L-carnitine chloride acid chloride (102 mg, 0.4 mmol) was added and the solution was stirred at room temperature for one hour. The solvent was then removed on the rotary evaporator and the residue was triturated with ether. The crude material was then dissolved in isopropyl alcohol (4 ml) and precipitated with ether (30 ml). The resulting yellow solid was dried in vacuo and first triturated with acetone and then with hexane/ether (1/1). After vacuum drying, 150 mg of yellow solid was obtained and used directly in the following reaction.

The above benzyl ether (150 mg, 0.21 mmol) was dissolved in methanol (10 ml) and 10% palladium-on-carbon catalyst (150 mg) was added. After degassing the mixture, hydrogen gas was added to the flask at slightly above one atmosphere and stirring was continued at room temperature for two hours. The reaction mixture was then filtered through diatomaceous earth and the filtrate rotary evaporated to dryness. The residue was triturated twice with ether/hexane 1/1 and vacuum dried to give 100 mg (76% yield) of the desired product.

7.2 Preparation of Progesterone 3-{2-O-[10-O-(O-acetylcarnitinyl)decanoyl]glycolic acid} enol ester Progesterone (0.5 g, 1.6 mmol) was dissolved in 2 g (7.7 mmol) of bromoacetic anhydride containing p-toluenesulfonic acid (50 mg) and heated at 100° C. for 0.5 hours. After cooling the mixture was dissolved in ethyl acetate, washed with saturated sodium bicarbonate, dried over sodium sulfate and the solvent removed by evaporation. The residue was purified by silica gel column chromatography (elution with 1% ethyl acetate in dichloromethane) to give 310 mg (44%) of the enol acetate.

The above enol ester (100 mg, 0.23 mmol) was added to a mixture of 10-hydroxydecanoic acid (43 mg, 0.23 mmol) and anhydrous potassium fluoride (27 mg, 0.46 mmol) in 4 ml of a 1:1 mixture of acetonitrile and dimethylformamide and stirred at room temperature for 48 hours. The mixture was diluted with ethyl acetate, washed with saturated sodium bicarbonate, dried over sodium sulfate and filtered. The filtrate was evaporated to give 117 mg crude product which was purified by silica gel column chromatography (elution with 20% ethyl acetate in dichloromethane) to give 92 mg of the hydroxyl diester.

The hydroxyl diester (74 mg, 0.14 mmol) was dissolved in dichloromethane (2 ml) containing diisopropylethylamine (35 mg, 0.28 mmol) and stirred at 0° C. while a solution of 3-O-acetyl-L-carnitine acid chloride (prepared from 33 mg of 3-O-acetyl-L-carnitine and oxalyl chloride) in dichloromethane (2 ml) was added. The mixture was stirred at room temperature for 12 hours, decanted from salts and rotary evaporated to dryness. The oily residue was dissolved in toluene (2 ml) and added dropwise to ether/hexane (30 ml, 1/1). The resulting precipitate was separated by centrifugation, washed with hexane and redissolved in toluene, centrifuged to remove a small amount of insoluble salts, and the supernatant was evaporated to give 60 mg of the desired carnitine derivative.

7.3 Preparation of N-[17β-hydroxy-estra-1,3,5(10)-trien-3-yl)oxycarbonyl glycine] (choline iodide) ester To a solution of estradiol-3-acetate (280 mg, 0.89 mmol) in tetrahydrofuran (10 ml) was added a toluene solution of phosgene (5.7 ml, 1M solution). After stirring at room temperature for 2 hours the solvent was evaporated and the resulting solid dried under vacuum. The residue was redissolved in dichloromethane (10 ml) and added dropwise at 0° C. to a solution of benzyl alcohol (95 mg, 0.89 mmol) in pyridine (10 ml). After stirring for one hour at room temperature the mixture was poured into 1N hydrochloric acid and extracted with dichloromethane. The organic layer was dried over sodium sulfate, filtered and evaporated to give the 17β-benzyloxycarbonyl derivative (480 mg crude). The material was purified by column chromatography on silica gel (5% methanol in dichloromethane) to give the desired compound (325 mg, 81% yield).

After removal of the 3-acetate protecting group by base hydrolysis, the 3-hydroxyl group was converted to its chloroformate ester which was further reacted with glycine t-butyl ester. Thus, to a solution of the carbonate (230 mg, 0.57 mmol) in tetrahydrofuran (5 ml) was added diisopropylethylamine (73 mg, 0.57 mmol) and the resulting mixture was stirred at 0°–10° C. while phosgene in toluene (300 μl, 0.57 mmol) was slowly added. After stirring at this temperature for 1.5 hours the mixture was evaporated to dryness. The residue was dissolved in dichloromethane (5 ml) and the solution added slowly at 0° C. to a solution of glycine t-butyl ester hydrochloride (95 mg, 0.57 mmol) and diisopropylethylamine (146 mg, 1.32 mmol) in dichloromethane (3 ml). After stirring at room temperature for 12 hours, the solution was poured into saturated sodium bicarbonate and extracted with dichloromethane. The organic layer was dried over sodium sulfate, filtered and evaporated to give the desired 3-carbamate (320 mg).

The t-butyl ester protecting group of the above crude material was next removed by acid treatment. Thus, the 320 mg (0.57 mmol) was dissolved in dichloromethane (8 ml) and trifluoroacetic acid (2 ml) was added. The mixture was stirred at room temperature for one hour and then evaporated to dryness to give a quantitative yield (285 mg) of the 3-glycine carbamate.

This material was used directly to form an ester with N,N-dimethylaminoethanol. Thus, the carboxy of the glycine moiety was converted to its acyl chloride by reaction with oxalyl chloride by standard methods. The acyl chloride was dissolved in dichloromethane (4 ml) and added dropwise to a solution of N,N-dimethylaminoethanol (100 mg, 1.12 mmol) in dichloromethane (10 ml). After stirring at room temperature for 2 hours, the mixture was extracted with saturated sodium bicarbonate, the organic layer dried over sodium sulfate, filtered and evaporated to give 310 mg of crude product. Purification by column chromatography (silica gel, 10% methanol in dichloromethane) gave the desired ester (200 mg).

The benzyl carbonate protecting group at C-17 was then removed by treatment of 180 mg of material with 5% Pd/C catalyst (100 mg) in ethanol (20 ml) containing one drop of acetic acid. After filtration the solution was washed with saturated sodium bicarbonate, filtered, dried and evaporated to give 17-hydroxyl derivative in 94% yield.

The final step to give the desired compound was accomplished by methylation with methyl iodide. Thus, the dimethylaminoethyl ester (110 mg, 0.25 mmol) was dissolved in tetrahydrofuran (2 ml) and the solution diluted with ether (20 ml). Methyl iodide (50 mg) was then added and the solution stirred at room temperature overnight. The precipitated product was removed by centrifugation, washed twice with ether and dried in vacuo to give the final desired compound (83 mg, 57% yield).

7.4 Preparation of N-[3-hydroxy-estra-1,3,5(10-trien-17β-yl)oxycarbonyl] glycine (choline iodide) ester 3,17β-Estradiol-3-benzyl ether (200 mg, 0.55 mmol) was reacted with 3.5 ml of 1M phosgene in tetrahydrofuran to give the 17-chloroformate derivative. The crude product (234 mg, 0.55 mmol) was dissolved in dichloromethane (2 ml) and added dropwise to a solution of glycine t-butyl ester (73 mg, 0.55 mmol) and diisopropylethylamine (143 mg, 1.1 mmol) in dichloromethane (15 ml). After stirring at room temperature for one hour the reaction mixture was washed with 5% sodium bicarbonate solution and 0.1N hydrochloric acid. The organic solution was dried over sodium sulfate, filtered and evaporated to give 260 mg (91% yield) of TLC-pure carbamate product.

The material was dissolved in dichloromethane (2 ml) and trifluoroacetic acid (2 ml) was added. After stirring for two hours at room temperature to remove the t-butyl ester the solution was evaporated to give 250 mg (100% yield) of the pure glycine carbamate free acid. The acid (233 mg, 0.5 mmol) was suspended in dichloromethane (10 ml) and converted to its acid chloride by addition of oxalyl chloride (63 mg, 0.5 mmol) and one drop of dimethylformamide. After stirring for one hour at room temperature the homogeneous solution was evaporated to dryness. The residue was redissolved in dichloromethane (3 ml) and added dropwise to a solution of N,N-dimethylaminoethanol (116 mg, 1.3 mmol) in dichloromethane (10 ml). After stirring one hour at room temperature the solution was poured into saturated sodium bicarbonate solution and extracted with dichloromethane. The organic layer was dried over sodium sulfate and evaporated to give 256 mg of crude product.

The benzyl ether protecting group of the 3-hydroxyl was next removed by hydrogenolysis. A solution of the material (194 mg, 0.36 mmol) in ethanol (15 ml) containing 4 drops of acetic acid was stirred under hydrogen gas in the presence of 5% Pd/C catalyst (194 mg) for 1.5 hours. The solution was filtered and evaporated to give 140 mg of crude deprotected alcohol which was further purified by flash chromatography on silica gel using 15% methanol in dichloromethane to give 107 mg (66% yield) of the 17-(norcholine glycinate carbamate) of estradiol.

This material (107 mg, 0.24 mmol) was then methylated by treatment of a dimethylformamide/ether (4 ml/4 ml) solution with methyl iodide (34 mg, 0.24 mmol) at room temperature for 12 hours. The reaction mixture was concentrated on the rotary evaporator and the viscous residue was dissolved in methanol (2 ml) and precipitated by dropwise addition to ether (50 ml). Further purification by additional reprecipitation give 100 mg (71% yield) of the desired choline ester of estradiol-17-glycine carbamate.

7.5 Preparation of 3-hydroxy-estra-1,3,5-trien-17β-yl 6-(O-acetyl-L-carnitinato)hexyl carbonate, chloride salt Phosgene in toluene (1.93M, 18 ml, 34.7 mmol) was added to a solution of 3,17β-estradiol-3-benzyl ether (1 g, 2.8 mmol) in tetrahydrofuran (60 ml) and the mixture stirred at room temperature for 4 hours. Solvent was removed by evaporation to give 1.13 g (95% yield) of the solid chloroformate derivative. This material was added in one portion to a solution of mono-dimethoxytrityl (DMT) protected 1,6-hexanediol (1.12 g, 2.6 mmol) in pyridine (20 ml) at 0° C. After stirring at this temperature for one hour the reaction was continued for an additional hour at room temperature. The mixture was then concentrated by evaporation, redissolved in ethyl acetate and washed with water. The solution was dried over sodium sulfate, filtered and solvent evaporated to give 2.1 g of crude product. This material was purified by silica gel column chromatography (elution with dichloromethane) to give 1.57 g (75% yield) of the carbonate ester.

The DMT and benzyl protecting groups were removed by dissolving the material in ethyl acetate/methanol (50 ml/50 ml) containing two drops of acetic acid and 1.5 g of 10% Pd/C and stirring under hydrogen gas for 4 hours. The reaction mixture was filtered through Celite and the solvent evaporated to give 560 mg (69% yield) of the diol product after recrystallization from toluene.

This material was converted to the final desired product by reaction of the primary hydroxyl with O-acetyl-L-carnitine acid chloride (chloride salt). Thus, the diol (353 mg, 0.85 mmol) was dissolved in dichloromethane (15 ml) and the acid chloride (from 203 mg, 0.85 mmol, of O-acetyl-L-carnitine hydrochloride) was added and the mixture stirred at room temperature for 3 hours. The mixture was filtered, the filtrate evaporated and the residue redissolved in isopropyl alcohol (5 ml). This solution was added dropwise to 70 ml of ether and the resulting solid was reprecipitated a second time in the same manner to give 237 mg (43% yield) of the final carnitine derivative.

7.6 Preparation of 2-(4-nitrophenyl)ethanol 6-(O-acetyl-L-carnitinamido)hexanoate ester, chloride salt 2-(4-Nitrophenyl)-ethanol (502 mg, 3 mmol) was dissolved in pyridine (2.5 ml) containing dicyclohexyl carbodiimide (DCC, 619 mg, 3 mmol) and, after stirring at room temperature for 10 minutes, a solution of N-t-BOC-6-aminohexanoic acid (664 mg, 3 mmol) in dichloromethane (5 ml) was added. After stirring for 2 hours an additional 206 mg (1 mmol) of DCC was added and stirring continued another 3 hours. The reaction mixture was filtered to remove the precipitated dicyclohexyl urea and the filtrate evaporated to dryness. The residue was purified by silica gel flash chromatography in 2/1 dichloromethane/ethyl acetate to give 920 mg (83% yield) of the t-BOC protected aminohexanoic ester.

The protecting group was removed by dissolving the ester 712 mg, 1.9 mmol) in trifluoroacetic acid(TFA)/dichloromethane (1 ml, ½) and stirring at room temperature for 3 hours. Addition of another ml of TFA and an additional 1 hour of stirring was required to complete the reaction after which the solvents were removed to give 1.01 g of oily residue. The residue was redissolved in dichloromethane, washed with saturated sodium bicarbonate, dried over sodium sulfate, filtered and evaporated to give 508 mg (98% yield) of the free amine.

The above free amine (340 mg, 1.25 mmol) was dissolved in dichloromethane (8 ml) along with triethylamine (1.55 mmol) and the solution cooled to in an ice bath. A solution of O-acetyl-L-carnitine acid chloride (1.42 mmol) in dichloromethane (7 ml) was then added dropwise with stirring. The ice bath was removed and stirring continued at room temperature for one hour. The mixture was evaporated to dryness and the residue washed with ether (2×20 ml). The material was redissolved in acetone (20 ml) with centrifugation to remove insoluble material. Evaporation of the acetone left an oily residue which was triturated with toluene and then with ether. The resultant product (505 mg) was found by NMR and TLC to consist mainly of the desired carnitine derivative with some triethylamine hydrochloride impurity.

7.7 Preparation of 1-(4-nitrophenyl)-2-propanol 6-(O-acetyl-L-carnitinamido)hexanoate ester 1-(4-Nitrophenyl)-2-propanol (720 mg, 3.97 mmol) and N-t-BOC-6-aminohexanoic acid (885 mg, 4 mmol) were dissolved in pyridine (2 ml). Dicyclohexyl carbodiimide (1.03 g, 5 mmol) was added and the reaction mixture was stirred at room temperature for 10 minutes followed by dilution with dichloromethane (4 ml) and stirring overnight. Some alcohol starting material was still present so dimethylaminopyridine (10 mg) was added and stirring continued for an additional 3 hours. The mixture was filtered to remove the precipitated dicyclohexyl urea and solvents removed by evaporation. The residue was purified by silica gel column chromatography using ethyl acetate/dichloromethane mixtures to give 1.14 g (75% yield) of the N-t-BOC-protected aminohexanoic ester.

The protecting group was removed by dissolving the ester (664 mg, 1.73 mmol) in 1/1 trifluoroacetic acid/dichloromethane (3 ml) and stirring at room temperature for one hour. The solvent was evaporated and the residue redissolved in dichloromethane (50 ml), washed with saturated sodium bicarbonate, filtered, dried over sodium sulfate and evaporated to give the free amine.

The crude amine (500 mg, 1.7 mmol) was dissolved in dichloromethane along with triethylamine (1.6 mmol) and a solution of O-acetyl-L-carnitine acid chloride (from 1.75 mmol of O-acetyl-L-carnitine) in dichloromethane (7 ml) was added dropwise at 0° C. After stirring for 30 minutes the mixture was warmed to room temperature and stirring continued for an additional 30 minutes. The solvent was evaporated and the residue triturated with ether (2×20 ml) and redissolved in acetone (20 ml). The solution/suspension was cooled in the freezer and centrifuged to remove insoluble material and then evaporated to give 750 mg of oily crude product. Further purification was accomplished by redissolving the material in acetonitrile (3 ml) and dropping into ether (50 ml). The precipitate was washed with ether, toluene and ether again and vacuum dried to give the final carnitine derivative.

7.8 Preparation of 2-(4-nitrophenyl)ethyl 3-(O-acetyl-L-carnitinamido)propanoate 2-(4-Nitrophenyl)-ethanol (501 mg, 3 mmol) and N-t-BOC-β-galanine (580 mg, 3.07 mmol) were dissolved in pyridine (1 ml) and dicyclohexyl carbodiimide (800 mg, 3.9 mmol) was added and the mixture stirred at room temperature for 10 minutes. The reaction mixture was then diluted by addition of dichloromethane (2 ml) containing a few milligrams of dimethylaminopyridine catalyst. After stirring for another two hours the mixture was filtered. The filtrate was diluted with dichloromethane, washed with water, 1N HCl, and water, dried over sodium sulfate, filtered and evaporated to give 1.2 g of crude oily residue. This material was purified by flash chromatography (silica gel, 10% ethyl acetate/dichloromethane) to give 0.98 g (97% yield) of the t-BOC-protected amino ester.

This compound (970 mg, 2.87 mmol) was stirred in a 50/50 mixture of TFA/dichloromethane for one hour. The solvent was evaporated, the residue redissolved in dichloromethane, and the solution washed with saturated sodium bicarbonate. The solution was dried (sodium sulfate), filtered and evaporated to give the free amino ester (660 mg, 2.77 mmol).

This material was dissolved in dichloromethane (15 ml) containing triethylamine (0.49 ml) and a solution of O-acetyl-L-carnitine acid chloride (3.2 mmol) in dichloromethane (10 ml) was added with stirring at 0° C. After one hour the mixture was allowed to warm to room temperature and stirring was continued overnight. The solvent was removed and the residue triturated with ether, redissolved in acetone, filtered and evaporated. The residue was redissolved in acetonitrile and precipitated by addition to ether to give the final carnitine conjugate.

7.9 Preparation of 1-(4-nitrophenyl)-2-propanol 6-(O-acetyl-L-carnitinamido)hexanol carbonate, chloride salt A solution of 6-(N-t-BOC-amino)-hexanol (0.9 g, 4.1 mmol) in pyridine (10 ml) was cooled in an ice bath and 1-(4-nitrophenyl)-2-propanol chloroformate (1 g, 4.1 mmol) in dichloromethane was added. After stirring at room temperature for 3 hours the mixture was diluted with dichloromethane, washed with water and 1N HCl, dried over sodium sulfate, filtered and evaporated to give 1.8 g of crude product which was purified by column chromatography (silica gel, 3% methanol/dichloromethane) to give 1.2 g (69% yield) of the t-BOC-amino carbonate.

This compound (600 mg, 1.4 mmol) was dissolved in dichloromethane (5 ml) and 5 ml of TFA was added. After stirring one hour at room temperature the solvent was evaporated and the residue redissolved in dichloromethane. The solution was washed with saturated sodium bicarbonate, dried over sodium sulfate and evaporated to give the free amine.

This material was redissolved in dichloromethane (15 ml) containing triethylamine (283 mg, 2.8 mmol) and the solution cooled in an ice bath. To this was added dropwise a solution of O-acetyl-L-carnitine acid chloride (1.75 mmol) in dichloromethane (5 ml). After warming to room temperature the solution was stirred for one hour and then evaporated. The residue was triturated with ether and then redissolved in acetone, centrifuged to remove insolubles, and the solvent removed to leave an oily residue. This material was redissolved in acetonitrile and reprecipitated in ether and centrifuged to give the final product (300 mg, 39% yield).

7.10 Preparation of 2-[4-(4-methoxyphenyl)butyramido] ethyl O-acetyl-L-carnitinate A solution of dicyclohexyl carbodiimide (1.03 g, 5 mmol) in dichloromethane (10 ml) was added to a solution of 4-methoxyphenylbutyric acid (971 mg, 5 mmol) and N-hydroxysuccinimide (576 mg, 5 mmol) in dichloromethane (40 ml) and the mixture stirred at room temperature for 30 minutes. The mixture was filtered and the filtrate evaporated to give 1.5 g of the NHS ester.

The NHS active ester (291 mg, 1 mmol) was dissolved in dichloromethane (5 ml) and the mixture was added to a solution of 2-aminoethanol (143 mg, 2 mmol) in the same solvent (15 ml). After stirring for 30 minutes a white precipitate had formed. The mixture was diluted with additional solvent, washed with water and saturated sodium bicarbonate, and the organic layer dried over sodium sulfate, filtered and evaporated to give 210 mg (89% yield) of desired amide alcohol.

This material (190 mg, 0.8 mmol) was dissolved in dichloromethane (5 ml) and a solution of O-acetyl-L-carnitine acid chloride (1.2 mmol) in dichloromethane (2 ml) was added with stirring. After 3 hours the reaction mixture was evaporated to dryness, the residue partially redissolved in acetone 915 ml), and insoluble material removed by filtration. The solvent was evaporated and the residue triturated with ether. The residue was again partially redissolved in acetone (2 ml), filtered and evaporated to give 190 mg (53% yield) of the desired carnitine derivative.

7.11 Preparation of 2-[4-(4-methoxyphenyl)butyramido] ethyl O-acetyl-L-carnitinthioate A solution of the NHS active ester of 4-(4-methoxyphenyl)butyric acid (874 mg, 3 mmol) in dichloromethane was added to a solution of cysteamine (376 mg, 4.8 mmol) in the same solvent (5 ml) and the mixture stirred at room temperature for one hour. The mixture was then diluted with dichloromethane (30 ml), washed with 5% citric acid and saturated sodium chloride, dried over sodium sulfate, filtered and evaporated to give 900 mg of crude product. This material was redissolved in dichloromethane/ethyl acetate and flash chromatographed using ethyl acetate for elution to give 560 mg (74% yield) of the thiol amide.

A solution of O-acetyl-L-carnitine acid chloride (2 mmol) in dichloromethane (2 ml) was added to a solution of the thiol amide (435 mg, 1.72 mmol) in the same solvent (3 ml) and the mixture stirred at room temperature for 36 hours. The insoluble material was removed by centrifugation and the supernatant was diluted with acetone. The additional precipitate (mostly O-acetyl-L-carnitine) thus formed was also removed by centrifugation and the supernatant was concentrated to a viscous oil. This material partially redissolved in acetonitrile (5 ml), the insolubles being the disulfide formed from the other starting material. The acetonitrile solution was evaporated to give a viscous oil which was further purified by trituration with toluene, redissolving in acetonitrile and precipitation in ether to give 290 mg (35% yield) of the desired thioester.

7.12 Preparation of testosterone-17-betainoyloxymethylcarbonyloxymethyl carbonate, iodide salt To a solution of testosterone (1.0 g, 3.5 mmol) in tetrahydrofuran (20 ml) and dichloromethane (10 ml) was added pyridine (274 mg, 0.0035 mol) and chloromethyl chloroformate (452 mg, 0.0035 mol). The reaction mixture was stirred at 0° C. for one hour. The reaction mixture was diluted with dichloromethane (100 ml), washed with 10% aqueous citric acid (2×30 ml) and saturated aqueous sodium chloride, dried over sodium sulfate, and concentrated in vacuo. The residue was triturated with 1% toluene in hexane. Column chromatography (flash silica, eluting with 8% methanol in dichloromethane) yielded the desired chloromethyl carbonate (1.08 g, 81% yield).

To a solution of the chloromethyl carbonate prepared above (1.08 g, 2.8 mmol) in acetone (15 ml) was added sodium iodide (853 mg, 5.6 mmol). The reaction mixture was refluxed for 4 hours, cooled and diluted with dichloromethane (40 ml). The solution was then washed with water and aqueous sodium thiosulfate, dried over sodium sulfate, and concentrated in vacuo. Column chromatography (flash silica, eluting with 10% methanol in dichloromethane) yielded the desired iodomethyl carbonate (920 mg, 70% yield).

To a solution of the iodomethyl carbonate prepared above (920 mg, 1.95 mmol) in acetonitrile (20 ml) was added DIEA (251 mg, 1.95 mmol). The reaction mixture was cooled to 0° C. To this solution was then added chloroacetic acid (184 mg, 1.95 mmol). The reaction mixture was stirred at 0° C. for 15 minutes and at room temperature for 30 minutes. The reaction mixture was diluted with dichloromethane (30 ml), washed with 0.1N aqueous hydrochloric acid, saturated aqueous sodium chloride, dried over sodium sulfate, and concentrated in vacuo to yield the chloromethyl ester. Column chromatography yielded the desired chloromethyl ester (800 mg) which was used immediately without further purification. The structure was verified by NMR.

To a solution of the above chloromethyl ester (800 mg, 1.83 mmol) in acetone (20 ml) was added sodium iodide (1.1 g, 7.3 mmol). The reaction was heated to reflux and stirred for 2 hours. The reaction mixture was cooled, filtered, and concentrated in vacuo. The residue was dissolved in dichloromethane, washed with saturated aqueous sodium chloride, and 5% aqueous sodium thiosulfate, dried over sodium sulfate, and concentrated in vacuo to yield the iodomethyl ester (910 mg) which was used immediately without further purification.

A solution of the iodomethyl ester prepared above (910 mg, 1.72 mmol) and trimethylamine (840 mg, 14 mmol) in toluene (20 ml) was stirred at room temperature for 1 hour and then concentrated in vacuo. The residue was triturated with ether and the precipitate was centrifuged to produce the desired trimethylammonium salt as a solid (660 mg). The structure was verified by NMR and mass spectroscopy.

7.13 Preparation of digoxin-12-{N-[6-(N',N',N'-trimethylamino)hexanoyloxymethyl]glycinoyloxymethyl} carbonate-3''',4'''-cyclic carbonate, bromide salt 6-Bromohexanoyl chloride (2 g, 9.37 mmol) was added to t-butanol (6.98 g, 93.7 mmol) under an inert atmosphere. The reaction mixture was stirred overnight and then was concentrated in vacuo, dissolved in ethyl acetate (150 ml), washed with saturated aqueous sodium bicarbonate and 10% aqueous citric acid, and dried over magnesium sulfate to yield t-butyl 6-bromohexanoate (2.02 g, 80% yield).

To a suspension of t-butyl 6-bromohexanoate (500 mg, 1.99 mmol) in hexamethylphosphoramide (10 ml) was added sodium acetate (180 mg, 2.19 mmol). The reaction mixture was stirred overnight, diluted with ether, and washed with 1N aqueous hydrochloric acid (3×100 ml) and water and dried over magnesium sulfate to yield the desired diester (660 mg, 80% yield) whose structure was confirmed by NMR.

The diester prepared above (1.52 g, 6.6 mmol) and ethylenediamine (539 mg, 3.82 mmol) were combined and heated to 100° C. for 2 hours. Additional ethylenediamine was added (1 equivalent) and the reaction was stirred at 100° C. for another 5 hours. The reaction mixture was then cooled to room temperature, diluted with dichloromethane (75 ml), washed with water, saturated aqueous sodium bicarbonate, 10% aqueous citric acid, and water, and dried over magnesium sulfate to yield a clear oil (560 mg). NMR analysis indicated that about 20% of the diester remained. The oil was treated with additional ethylenediamine (600 µl) at 100° C. for 2 hours and at room temperature for 48 hours. The reaction mixture was diluted with dichloromethane (100 ml), washed with saturated aqueous sodium bicarbonate, 10% aqueous citric acid, and water, dried over magnesium sulfate, and concentrated in vacuo to yield the desired t-butyl 6-hydroxyhexanoate (640 mg) in 52% yield. The structure was confirmed by NMR.

To a solution of 6-hydroxyhexanoate t-butyl ester (640 mg, 3.3 mmol) in dichloromethane (8 ml) was added diisopropylethylamine (543 mg, 4.2 mmol) in dichloromethane (2 ml). The reaction mixture was cooled to 0° C. and a solution of 4-bromobutyryl chloride (95% purity, 765 mg, 4.125 mmol) in dichloromethane (2 ml) was added. The ice bath was removed and the reaction mixture was stirred at room temperature for 2.5 hours. The mixture was diluted with dichloromethane (70 ml), washed with water, saturated aqueous sodium bicarbonate, and saturated aqueous sodium chloride, and dried to yield a crude yellow oil (1.21 g). Column chromatography (flash silica, eluting with dichloromethane) yielded the desired diester (656 mg, 60% yield).

The diester prepared above (650 mg, 1.928 mmol) was treated with trifluoroacetic acid (1.5 ml) and dichloromethane (3 ml). The reaction mixture was stirred at room temperature for 3 hours and then concentrated in vacuo to yield the carboxylic acid (about 660 mg) as an oil. The oil was treated with oxalyl chloride (350 µl, 3.94 mmol) in dichloromethane (5 ml) and DMF (1 drop) to form the acyl chloride. The reaction mixture was concentrated in vacuo and the acyl chloride was used immediately.

To a solution of digoxin di-butyltin complex (1.469 g, 1.45 mmol) in DMF (4 ml) and dichloromethane (3 ml) was added a solution of diisopropylethylamine (258 mg, 2.1 mmol) in dichloromethane (1 ml). The reaction mixture was cooled to 0° C. and the acyl chloride prepared above (1.9 mmol) was added. The reaction mixture was stirred at room temperature overnight and then concentrated in vacuo. Chromatography (flash silica, eluting with dichloromethane:isopropyl alcohol 95:5) yielded the desired digoxin ester (750 mg, 50% yield) whose structure was verified by NMR.

To a solution of the digoxin ester prepared above (750 mg, 0.7185 mmol) in acetonitrile (45 ml) was added trimethylamine in ethanol (4.2M, 4 ml). The reaction mixture was stirred at room temperature for 13 hours and then concentrated in vacuo. The residue was triturated with ether and the precipitate was centrifuged. The solid (700 mg) was dissolved in dichloromethane:methanol (20:1, 10 ml) and precipitated with ether (100 ml). The process was repeated twice to produce the desired trimethylammonium salt as a solid (679 mg, 85.7% yield) whose structure was confirmed by NMR.

7.14 Preparation of digoxin-4'''-4-(4-trimethylaminobutyroyloxy)butyrate, bromide salt Following the procedure set forth above, replacing 4-bromobutanoic acid for 6-bromohexanoic acid, the corresponding trimethylammonium salt was prepared. The structure was confirmed by NMR and mass spectroscopy 7.15 Preparation of indomethacin 6-(O-acetyl-L-carnitinamido)hexanoyloxymethyl ester, chloride salt To a suspension of indomethacin (2.56 g, 8 mmol) in dichloromethane (16 ml) was added a solution of sodium bicarbonate (2.55 g, 30 mmol) in water (12 ml) and tetrabutylammonium hydrogen sulfate (272 mg, 0.8 mmol). The reaction mixture was stirred at room temperature. A solution of chloromethanesulfonyl chloride (1.715 g, 9.2 mmol) in dichloromethane (3 ml) was added and the reaction mixture was stirred at room temperature for about 2 hours. The dichloromethane layer was separated, washed with water, concentrated in vacuo and filtered through a 5 cm alumina column (eluting with dichloromethane:methanol 20:1), and again concentrated in vacuo to yield the desired chloromethyl ester (3.09 g, 95% yield). The structure was confirmed by NMR.

A solution of the chloromethyl ester prepared above (2.52 g, 6.20 mmol) in acetone (25 ml) was treated with sodium iodide (1.8 g, 12 mmol). The reaction mixture was stirred at room temperature for 18 hours. The precipitate was removed by centrifugation and washed in acetone (30 ml). The acetone solutions were combined and concentrated in vacuo. Column chromatography (flash silica, dissolving the crude compound in trace dichloromethane and eluting with cyclohexane:ethyl acetate 10:2) to yield the desired iodomethyl ester (2.5 g, 79% yield, mp 98°101° C.) whose structure was confirmed by NMR.

A solution of tBOC-aminocaproic acid (221.3 mg, 1 mmol) and diisopropylethyl amine (175 μl) in acetonitrile (3 ml) was stirred at room temperature for 30 minutes. To this solution was added a solution of the iodomethyl ester prepared above (498 mg, 1 mmol) in acetone (3 ml) and acetonitrile (3 ml). The reaction mixture was stirred at room temperature for 3 hours and then concentrated in vacuo. The residue was dissolved in ethyl acetate (40 ml) and the precipitate was centrifuged out. The supernate was washed with 0.1N aqueous hydrochloric acid, saturated aqueous sodium chloride, saturated aqueous sodium bicarbonate, and saturated aqueous sodium chloride, dried over sodium sulfate, and concentrated in vacuo to yield the desired ester (580 mg).

To a solution of this ester (580 mg) in dichloromethane (1 ml) was added trifluoroacetic acid. The reaction mixture was stirred at room temperature for 3 hours and then concentrated in vacuo. The residue was dissolved in toluene and concentrated in vacuo. The oily residue was dissolved in dichloromethane (40 ml), washed with saturated aqueous sodium chloride, saturated aqueous sodium bicarbonate, and saturated aqueous sodium chloride, dried over sodium sulfate, and concentrated in vacuo to yield the desired amine which was used immediately without further purification.

To a solution of L-carnitine-O-acetate (264 mg, 1.1 mmol) in dichloromethane (7 ml) and DMF (1 drop) was added oxalyl chloride (200 μl, about 2.5 mmol). The reaction mixture was stirred at room temperature for 2.5 hours to yield the acyl chloride. To a 0° C. solution of the amine prepared above (450 mg) in dichloromethane (10 ml) was added diisopropylethylamine (209 μl, about 1.2 mmol). A solution of the acyl chloride in anhydrous dichloromethane (3 ml) was then added. The reaction mixture was stirred at 0° C. for 15 minutes and then warmed to room temperature. The reaction mixture was filtered and concentrated in vacuo. The residue was triturated with acetone:ether (1:3, 40 ml). The oily precipitate was dried in vacuo, dissolved in acetonitrile (3 ml), and centrifuged. The filtrate was diluted with isopropyl ether and the precipitate was centrifuged out. The precipitate was dissolved in acetone (6 ml) and the precipitate was centrifuged out. The supernate was concentrated in vacuo and triturated with ether to yield the desired trimethylammonium salt (160 mg) with a molecular mass of 686 by FAB mass spectrometry.

7.16 Preparation of digoxin-4'''-6-O-palmitoylcarnitinamido)hexyl carbonate, chloride salt To a solution of 6-aminohexanol (660.2 mg, 5.633 mmol) in dichloromethane (50 ml) was added solid FMOC-NHS (1.90 g, 5,633 mmol). The reaction mixture was stirred at room temperature overnight. Additional 6-aminohexanol (330 mg, 2.816 mmol) was added and the reaction was stirred at room temperature for an additional 30 minutes. The solution was diluted with dichloromethane (30 ml), washed with water (2×50 ml), 1N aqueous hydrochloric acid (1×50 ml), and water, dried over sodium sulfate, and concentrated in vacuo to yield FMOC-6-aminohexanol (1.07 g, 46% yield).

A solution of FMOC-6-aminohexanol (617.2 mg, 1.5 mmol) in tetrahydrofuran (6 ml) was heated and then cooled to room temperature. To this solution was then added phosgene (2.9 ml, 1.93M in toluene). The reaction was stirred at room temperature for 15 hours and concentrated in vacuo to yield FMOC-6-aminohexanol chloroformate which was used immediately without further purification.

To a 0° C. solution of digoxin di-butyl tin oxide (1.315 g, 1.3 mmol) in pyridine (1.25 ml) and dichloromethane (2.5 ml) was added the FMOC-6-amino-hexanol chloroformate prepared above in dichloromethane (2 ml). The reaction mixture was stirred at 0° C. for an hour. The ice bath was removed and the reaction mixture was stirred for an additional 5 hours. The reaction mixture was diluted with dichloromethane (70 ml), washed with water (2×20 ml), dried over sodium sulfate, and concentrated in vacuo to yield a solid (2.0 g) which was purified by column chromatography (flash silica, eluting first with dichloromethane:ethyl acetate, 2:1, 500 ml, then dichloromethane:ethyl acetate, 1:1, 450 ml), and finally dichloromethane:methanol, 95:5, 450 ml). The desired carbonate (1.06 g) was produced in 66.9% yield.

A solution of the carbonate prepared above (520 mg, 0.428 mmol) in dichloromethane (16 ml) was treated with a solution of 1,8-diazabicyclo[5.4.0]undec-7-ene (DBU, 41 mg) in dichloromethane (2 ml). The reaction mixture was stirred at room temperature for 20 minutes and then cooled to 0° C. To this solution was added diisopropylethylamine (113 μl) and L-carnitinyl-O-palmitate (253 mg, 0.58 mmol) and the reaction mixture was stirred at 0° C. for 30 minutes. The reaction mixture was then allowed to warm to room temperature and was stirred for an additional 30 minutes. The reaction mixture was concentrated in vacuo and the residue was triturated with acetone (30 ml). The soluble fraction (510 mg) was concentrated in vacuo and was found to contain mostly cyclic carbonate, although some palmitate ester was also present. The precipitate was heated with acetonitrile (10 ml) and then cooled to room temperature. The precipitate was centrifuged and washed with acetonitrile (5 ml). The supernate was concentrated in vacuo to yield precipitate II which was further purified by precipitation from dichloromethane:methanol (10:1, 3 ml), followed by precipitation from ether.

The acetonitrile soluble fraction was dissolved in dichloromethane:methanol (10:1, 2 ml) and precipitated with ether to yield precipitate I (60 mg). Precipitates I and II were combined and chromatographed (flash silica, eluting with 10% methanol in dichloromethane (300 ml) and then 15% methanol in dichloromethane (400 ml), followed by 20% methanol in dichloromethane (20%). The major product was concentrated in vacuo and triturated in ether to yield the desired product (23 mg) whose structure was confirmed by NMR.

7.17 Preparation of digoxin-12-[1-(6-betainoyloxyhexyl)] carbonate-3''',4'''-cyclic carbonate, chloride salt To a solution of 1,6-hexanediol (3.073 g, 26 mmol) in THF (36 ml) was added chloroacetyl chloride (1.13 g, 10 mmol). The reaction mixture was stirred at room temperature overnight and then concentrated in vacuo to yield the crude monoester (4.2 g) which was dissolved in ethyl acetate (75 ml), washed with water (2×100 ml), saturated aqueous sodium bicarbonate (1×100 ml), and water (1×100 ml), dried over sodium sulfate, and concentrated in vacuo. Column chromatography (flash silica, eluting with ethyl acetate:dichloromethane 1:5, then 1:3) yielded the desired monoester (1.233 g, 63.3% yield).

To a solution of the monoester prepared above (400 mg, 2.06 mmol) in THF (5 ml) was added phosgene (3.1 ml, 1.93M in toluene). The reaction mixture was stirred at room temperature for one hour and then concentrated in vacuo to yield the desired chloroformate which was used immediately without further purification.

A solution of digoxin-3''',4'''-cyclocarbonate (733 mg, 0.91 mmol) and diisopropylethylamine (2.84 mg, 2.2 mmol) in dichloromethane (8 ml) was cooled to 0° C. To this solution was added the chloroformate prepared above and 4-dimethylaminopyridine (268.8 mg). The reaction mixture was stirred at room temperature overnight, diluted with dichloromethane (100 ml), washed with water, dried over sodium sulfate, and concentrated in vacuo to yield a crude oil. Column chromatography (flash silica, eluting with methanol:dichloromethane 4:100) yielded the desired chloromethylacetate ester (214 mg, 23% yield). The structure was confirmed by NMR.

To a solution of the chloromethylacetate ester prepared above (214 mg, 0.208 mmol) in acetonitrile (5 ml) was added an ethanolic solution of trimethylamine (4.2M, 0.5 ml, 2.1 mmol). The reaction mixture was stirred at room temperature for 3 hours and then concentrated in vacuo. The residue was triturated with ether to yield a crude solid (208 mg) which was dissolved in chloroform:methanol (10:1, 3 ml) and precipitated with ether. This process was repeated twice to yield the desired trimethylammonium salt (178 mg, 79% yield) whose structure was confirmed by mass spectroscopy and NMR.

7.18 Preparation of digoxin-12-{N-[6-(N',N',N'-trimethylamino)hexanoyloxymethyl]glycinoyloxymethyl} carbonate-3''',4'''-cyclic carbonate, bromide salt Glycine t-butyl ester hydrochloride (2.51 g, 15 mmol) was treated with 10N aqueous sodium hydroxide (1.6 ml) and extracted with dichloromethane (50 ml). The dichloromethane solution was back washed with saturated aqueous sodium chloride (2×5 ml), dried over sodium sulfate, and concentrated in vacuo to yield the glycine t-butyl ester (1.38 g, 70% yield).

To a solution of glycine t-butyl ester (1.38 g, 10.52 mmol) in dichloromethane (30 ml) was added DIEA (1.32 g, 10.52 mmol). The reaction mixture was cooled to 0° C. To this solution was then added chloromethyl chloroformate (1.356 g, 10.52 mmol). The reaction mixture was stirred at 0° C. for 15 minutes and at room temperature for 30 minutes. The reaction mixture was diluted with dichloromethane (30 ml), washed with 0.1N aqueous hydrochloric acid, saturated aqueous sodium chloride, dried over sodium sulfate, and concentrated in vacuo to yield the crude chloromethyl carbamate (2.11 g). Column chromatography (using flash silica on a sinterred glass funnel, eluting with 2% methanol in dichloromethane) yielded the desired chloromethyl carbamate glycine ester (1.82 g, 89% yield) which was used immediately without further purification. The structure of the ester was confirmed by NMR.

To a solution of the above chloromethyl carbamate glycine ester (415 mg, 1.856 mmol) in acetone (30 ml) was added sodium iodide (1.07 g, 1.0 mmol). The reaction was heated to reflux and stirred for 90 minutes. The reaction mixture was cooled, filtered, and concentrated in vacuo. The residue was dissolved in dichloromethane, washed with saturated aqueous sodium chloride, and 0.5% aqueous sodium sulfite, dried over sodium sulfate, and concentrated in vacuo to yield the iodomethyl carbamate (359 mg, 60.5% yield) which was used immediately without further purification. When this reaction was run at room temperature for 5 hours rather than at reflux, the 6-iodohexanoic acid ester was isolated in 85.2% yield.

To a solution of 6-bromohexanoic acid (220.4 mg, 1.13 mmol) and DIEA (145 mg, 1.13 mmol) in acetonitrile (2 ml) was added a solution of the iodomethyl carbamate ester prepared above (359 mg, 1.14 mmol) in acetonitrile (5 ml). The reaction mixture was stirred overnight at room temperature and was then concentrated in vacuo, diluted with dichloromethane (50 ml), washed with saturated aqueous sodium chloride, saturated aqueous sodium bicarbonate, saturated aqueous sodium chloride, 10% aqueous citric acid, and saturated aqueous sodium chloride, dried, and concentrated in vacuo. Column chromatography (flash silica, eluting with 3% methanol in dichloromethane) yielded a mixture of the 6-bromohexanoic acid ester and the 6-iodohexanoic acid ester (60:40 by NMR spectroscopy, 254 mg total).

To a solution of the 6-bromohexanoic acid ester prepared above (250 mg, 0.654 mmol) in dichloromethane (1.6 ml) was added trifluoroacetic acid (0.4 ml). The reaction mixture was stirred at room temperature for one hour. Additional trifluoroacetic acid (0.4 ml) was then added and the reaction mixture was stirred for an additional hour. The reaction mixture was concentrated in vacuo to yield the desired carboxylic acid $Br(CH_2)_5CO_2CH_2OCONHCH_2COOH$ (209 mg, 98% yield).

To a 0° C. solution of the 3''',4'''-cyclocarbonate of digoxin, prepared as above, (700 mg, 0.87 mmol) in DMF (3 ml) and dichloromethane (2 ml) was added pyridine (87 mg, 1.1 mmol) and chloromethylchloroformate (141.9 mg, 1.1 mmol). The reaction mixture was stirred at 0° C. for one hour. Additional pyridine (79 mg, 1.0 mmol) and a 0° C. solution of chloromethylchloroformate (128.9 mg, 1.0 mmol) in dichloromethane (2 ml) was added. The reaction mixture was stirred for 15 minutes. TLC showed that only trace amounts of digoxin-3''',4'''-cyclocarbonate remained. The reaction mixture was diluted with dichloromethane (100 ml), washed with 10% aqueous citric acid (2×30 ml) and saturated aqueous sodium chloride, dried over sodium sulfate, and concentrated in vacuo. Column chromatography (flash silica, eluting with 2% methanol in dichloromethane) yielded the desired chloromethyl carbonate (650 mg, 83% yield).

A solution of the digoxin 12-chloromethyl carbonate-3''',4'''-cyclic carbonate (600 mg, 0.74 mmol) in acetonitrile (10 ml) was stirred with potassium bicarbonate powder (30 mg) and sodium iodide (320 mg) in the dark overnight. The reaction mixture was concentrated in vacuo, extracted with dichloromethane (100 ml), filtered, and concentrated in vacuo to yield the desired iodomethyl carbonate (648 mg, 98% yield) which was used immediately without further purification.

To a solution of iodomethyl carbonate (324 mg, 0.326 mmol) in acetonitrile (5 ml) was added a solution of the 6-bromohexanoate ester $Br(CH_2)_5CO_2CH_2OCONHCH_2COOH$ (0.33 mmol) and DIEA (430 mg, 0.33 mmol) in acetonitrile (2.5 ml). The reaction mixture was stirred at room temperature for two hours, diluted with dichloromethane (70 ml), washed with saturated aqueous sodium bicarbonate, saturated aqueous sodium chloride, 10% aqueous citric acid, and saturated aqueous sodium chloride, dried over sodium sulfate, and concentrated in vacuo to yield crude carbamate (300 mg). Column chromatography (flash silica, eluting with 2% methanol in dichloromethane (500 ml) and 2.5% methanol in dichloromethane yielded the desired product (165 mg, 43% yield).

Trimethylamine was bubbled into a solution of the bromo carbamate prepared above (165 mg, 0.137 mmol) in acetonitrile (10 ml) for four minutes. The reaction flask was then closed and the reaction mixture was stirred at room temperature for 2 hours. The reaction mixture was concentrated in vacuo and then triturated with ether. The precipitate was centrifuged out and then redissolved in methanol:dichloromethane (1:8, 1.5 ml) and then precipitated out with ether to yield the desired trimethylammonium salt (103 mg). The solid was dissolved in methanol:dichloromethane (1:8, 5 ml) and precipitated out with ether (40 ml) to yield the pure salt (103 mg, 85.4% yield) with a molecular mass of 1167.7 by FAB mass spectrometry.

7.19 Preparation of 4-fluorouracil-1-N-(4-trimethylaminobutyroyloxy-1-ethyl), iodide salt 4-Chlorobutyryl chloride (12.69 g, 90 mmol) was mixed with paraldehyde (3.964 g, 30 mmol) and heated at 85° C. for 90 minutes. Additional paraldehyde (1.35 g) was added and the reaction mixture was stirred at 85° C. for an additional hour. The reaction mixture as cooled to room temperature, diluted with dichloromethane (100 ml) and stirred with saturated aqueous sodium bicarbonate (50 ml) at room temperature for 10 minutes. The dichloromethane layer was separated, dried over sodium sulfate and concentrated in vacuo to yield $Cl(CH_2)_3CO_2CHClCH_3$ which was vacuum distilled (55°–58° C. at 0.1 mm, 9.65 g, 58.6% yield) whose structure was confirmed by NMR.

5-Fluorouracil (390.25 mg, 3 mmol) in DMA (4 ml) was treated with DIEA (517 mg) and the 1-chloroethyl ester prepared above (714 mg, 3.9 mmol). The reaction mixture was stirred at room temperature overnight, diluted with water (40 ml), and extracted with ethyl acetate (2×60 ml). The ethyl acetate layers were combined, dried over sodium sulfate, and concentrated in vacuo to yield the crude ester which was dissolved in chloroform (50 ml) and filtered. The filtrate was concentrated in vacuo and dissolved in methanol:dichloromethane (1:10). Column chromatography (flash silica, eluting with ethyl acetate:dichloromethane, 1:1, 500 ml, and then 1:4) yielded the desired ester (555 mg, 66.4% yield, mp 190°–191° C.).

A solution of the ester prepared above (132 mg, 0.473 mmol) in acetone (40 ml) was heated at reflux with sodium iodide (280 mg) for 15–16 hours. Additional sodium iodide (280 mg) was then added and the reaction mixture was heated at reflux for an additional 24 hours. The reaction mixture was then concentrated in vacuo, diluted with ethyl acetate (50 ml), washed with water, 5% aqueous sodium thiosulfate, and saturated aqueous sodium chloride, dried over sodium sulfate, and concentrated in vacuo to yield the desired iodo compound (153 mg, 87.4% yield), which was used immediately without further purification.

The iodo compound prepared above (153 mg, 0.413 mmol) was dissolved in a solution of trimethylamine in acetonitrile (1.02M, 10 ml). The reaction mixture was stirred at room temperature for 6 hours and was then concentrated in vacuo. The residue was triturated with acetonitrile (2 ml) and ether (10 ml). The insoluble material was centrifuged out and dried in vacuo to yield the desired trimethylammonium salt (145 mg, 81% yield, mp 206°–208° C.) whose structure was confirmed by NMR.

7.20 Preparation of digoxin 12-(6-trimethylaminohexanoyloxymethyl carbonate)-3′′′,4′′′-cyclic carbonate, bromide salt To a 0° C. solution of digoxin di-butyltin complex (1.518 g, 1.5 mmol) in DMF (5 ml) and dichloromethane (3 ml) was added a solution of diisopropylethylamine (389 mg, 3 mmol) in dichloromethane (1 ml). To the reaction mixture was added a solution of 4-nitrophenyl chloroformate (423.3 mg, 2.1 mmol) in dichloromethane (3 ml). The ice bath was removed and the reaction mixture was stirred at room temperature for one hour. Thin layer chromatography showed that only trace amounts of digoxin remained with 95% of the digoxin converted to digoxin-3′′′,4′′′-cyclocarbonate. The reaction mixture was concentrated in vacuo at a temperature <30° C. and diluted with saturated aqueous sodium chloride. The white precipitate was extracted with dichloromethane (75 ml). The dichloromethane solution was washed saturated aqueous sodium bicarbonate (3×30 ml), saturated aqueous sodium chloride (2×30 ml), saturated aqueous sodium carbonate (2×30 ml), and saturated aqueous sodium chloride (2×30 ml). The dichloromethane solution was concentrated in vacuo to yield a yellowish solid (1.60 g). Column chromatography (3.1 cm×45.7 cm, flash silica, eluting with 1 liter of 4% methanol in dichloromethane followed by 400 ml of 6% methanol in dichloromethane) yielded the cyclic carbonate (1.15 g, 95% yield). The structure of the cyclic carbonate was confirmed by NMR.

To a 0° C. solution of the 3′′′,4′′′-cyclocarbonate of digoxin, prepared as above, (700 mg, 0.87 mmol) in DMF (3 ml) and dichloromethane (2 ml) was added pyridine (87 mg, 1.1 mmol) and chloromethyl chloroformate (141.9 mg, 1.1 mmol). The reaction mixture was stirred at 0° C. for one hour. Additional pyridine (79 mg, 1.0 mmol) and a 0° C. solution of chloromethylchloroformate (128.9 mg, 1.0 mmol) in dichloromethane (2 ml) was added. The reaction mixture was stirred for 15 minutes. TLC showed that only trace amounts of digoxin-3′′′,4′′′-cyclocarbonate remained. The reaction mixture was diluted with dichloromethane (100 ml), washed with 10% aqueous citric acid (2×30 ml) and saturated aqueous sodium chloride, dried over sodium sulfate, and concentrated in vacuo. Column chromatography (flash silica, eluting with 2% methanol in dichloromethane) yielded the desired digoxin cyclic carbonate ester (650 mg, 83% yield). This 12-chloromethyl carbonate ester was converted to the corresponding iodomethyl ester using sodium iodide in acetonitrile. Supra.

A solution of digoxin-3′′′,4′′′-cyclocarbonate-12-carbonate iodomethyl ester (200 mg, 0.202 mmol) in anhydrous acetonitrile (5 ml) was treated with a mixture of diisopropylethylamine (32 mg, 0.25 mmol) and 6-bromohexanoic acid (48.9 mg, 0.25 mmol) in anhydrous acetonitrile (1 ml). The reaction mixture was stirred at room temperature for 5 hours. After about 2.5 hours, a small sample was removed and concentrated under a stream of nitrogen. NMR spectroscopy (examining the doublet of doublets at $\partial 6.0$) showed that most of the starting material had been converted. The reaction mixture was concentrated in vacuo and dissolved in dichloromethane. The dichloromethane solution was washed with saturated aqueous sodium chloride, saturated aqueous sodium bicarbonate, saturated aqueous sodium chloride buffered to pH 4, and saturated aqueous sodium chloride, dried, and concentrated in vacuo to yield the desired carbonate (167 mg, 78% yield) whose structure was confirmed by NMR.

To a solution of the above carbonate (167 mg, 0.158 mmol) in acetonitrile (10 ml) was added a solution of trimethylamine (0.74 ml, 4.2 mmol) in ethanol. The reaction mixture was stirred at room temperature for 7 hours. TLC analysis indicated a trace of starting material. The reaction mixture was concentrated in vacuo and dissolved in dichloromethane:methanol (10:0.8, 2–3 ml) and added to rapidly stirring ether. The precipitate was removed using a centrifuge. The process was repeated twice to yield the crude trimethylammonium salt (129 mg). NMR and TLC analyses indicated a trace of digoxin-3''',4'''-cyclocarbonate (_5%). The precipitate was dissolved in dichloromethane:methanol (95:5, 5 ml) and precipitated out in ether (50 ml). This procedure was repeated. TLC indicated only a small trace of the cyclocarbonate impurity. The desired salt (117 mg) was obtained in 67% yield.

EXAMPLE 8

Negatively Charged Chemical Modifiers 8.1 Preparation of digitoxigenin-3-sulfate, triethylammonium salt Solid triethylamine-sulfur trioxide (181.3 mg, 1.0 mmol) was added to a solution of digitoxigenin (299.6 mg, 0.8 mmol) in pyridine (1.5 ml). The reaction mixture was stirred at room temperature for 1.5 hours and then diluted with ether (30 ml) to precipitate an oily gum. The ether layer was decanted and the residue triturated several times with fresh ether to give a solid which, after drying in vacuo, weighed 425 mg (96% yield, mp 158°–163° C., NMR and mass spec. agreed with assigned structure).

8.2 Preparation of digitoxin-4'''-sulfate, triethylammonium salt

Solid triethylamine-sulfur trioxide (99.7 mg, 0.55 mmol) was added to a solution of digitoxin (382.5 mg, 0.5 mmol) in pyridine (1.5 ml) and the reaction mixture stirred at room temperature for 2.5 hours. The solution was then added slowly to ether to precipitate an oil which solidified on trituration with ether (3×30 ml). The solid (244 mg) was purified by flash chromatography on silica gel with elution by 10% methanol in chloroform (200 ml) to remove unreacted digitoxin. Further elution using 20% methanol in chloroform gave several fractions containing a single spot on TLC. These were pooled and evaporated to give the product (90 mg, 19% yield, NMR and mass spectroscopy agreed with assigned structure).

EXAMPLE 9

Preparation of Bis Adducts 9.1 Preparation of piroxicam bis(choline chloride) adduct Piroxicam (221 mg, 0.67 mmol) was dissolved in dimethylformamide (2 ml) and diisopropylethylamine (250 μl, 1.4 mmol) was added. The solution was stirred at room temperature while solid choline chloride chloroformate (290 mg, 1.44 mmol) was added in portions over 10 minutes. The bright yellow solution turned reddish-brown with overnight stirring and a small amount of precipitate formed. Addition of dichloromethane (20 ml) resulted in formation of more precipitate which was removed by centrifugation. The supernatant was concentrated on the rotary evaporator to about 2 ml and then diluted with toluene (30 ml) to give a second precipitate. The first precipitate was triturated with dichloromethane (3×10 ml) and acetone (3×10 ml) and the residue was partially dissolved in warm acetonitrile (5 ml). After filtration, the solvent was evaporated and the residue further triturated with acetone and ether. The remaining solid (30 mg) was shown by NMR to be a bis adduct of choline chloride to the piroxicam which may be the carbonate ester of the phenolic hydroxyl along with an acyl derivative of either the nitrogen or the oxygen of the amide group. Treatment of this compound with saturated sodium carbonate at room temperature for 10 minutes resulted in total conversion back to piroxicam. Trituration of the second precipitate with acetone followed by dissolution in methanol/dichloromethane, concentration and further trituration with dichloromethane, acetone and ether gave finally 45 mg of another solid composed primarily of the bis adduct with a minor amount of possibly a mono adduct. Several other solid fractions obtained from evaporation of the various triturants were all impure, being contaminated with differing amounts of free choline.

9.2 Preparation of the bis-ketal of progesterone with glycerol-1-(3-O-lauryl)-D,L-carnitinate Progesterone (2 g, 6.4 mmol) and monoacetin (13 g, 99.5 mmol) were added to toluene (100 ml) along with p-toluenesulfonic acid (200 mg) and the mixture was refluxed in a Dean-Stark apparatus for four hours. The mixture was cooled to room temperature and washed with saturated sodium bicarbonate, dried over sodium sulfate and filtered. The solvent was removed and the residue was purified by silica gel column chromatography (elution with 30% ethyl acetate in dichloromethane) to give 1.57 g (45% yield) of the desired bis-ketal.

The bis-ketal diacetate (1.56 g, 2.86 mmol) was hydrolyzed by stirring its methanol solution (50 ml) containing two drops of 10N sodium hydroxide at room temperature for one hour. The mixture was then diluted with ethyl acetate, washed with saturated sodium chloride solution, dried over sodium sulfate and filtered. Evaporation of the solvent gave 674 mg of crude product which was further purified by precipitation from an acetone with hexane. This material (140 mg, 0.3 mmol) was then esterified by reaction with 3-O-lauryl-D,L-carnitine (230 mg, 0.6 mmol) in dichloromethane solution using oxalyl chloride (0.6 mmol) and triethylamine (0.6 mmol) to give 53 mg of the desired product as a mixture of isomers.

9.3 Preparation of methotrexate-bis-choline ester, dibromide salt

A solution of methotrexate (233 mg, 0.512 mmol) and cerium carbonate (171 mg, 0.523 mmol) in anhydrous DMSO (8 ml) was sonicated and stirred at room temperature for 1.5 hours. To this reaction mixture was then added a solution of 1,2-dibromoethane (188 mg, 1 mmol) in DMSO (2 ml). The reaction mixture was stirred at room temperature for 39 hours and concentrated in vacuo. The residue was triturated with pH 4 acetate buffer and the resulting yellow solid was filtered and dried in an vacuum oven. The yellow solid (255 mg) was dissolved in methanol:chloroform (1:10, 20 ml) and filtered. The filtrate was concentrated in vacuo to yield a light yellow solid (130 mg) which was dissolved in 5% methanol in dichloromethane and chromatographed (dry column, silica gel) to yield the desired diester (69 mg, 20% yield) whose structure was confirmed by NMR.

Alternatively, the desired diester can be prepared in higher yield by the following procedure. Thus, to a solution of methotrexate (100 mg, 0.22 mmol) in 2-bromoethanol (5 ml) was added concentrated hydrochloric acid (25 μl). The reaction was stirred in the dark for two days and then concentrated in vacuo. The residue was triturated with aqueous sodium bicarbonate and extracted with chloroform 93×25 ml). The organic layer was washed with 50 mM pH 7.3 phosphate buffer, dried over sodium sulfate, and concentrated in vacuo to yield crude diester (160 mg). Column chromatography (flash silica, eluting with 2% methanol in dichloromethane (100 ml), followed by 4% methanol in dichloromethane (200 ml), 6% methanol in dichloromethane (200 ml), and finally 8% methanol in dichloromethane (200 ml) yielded pure diester (70 mg, 47.7% yield) whose structure was confirmed by NMR.

A solution of the diester prepared above (65 mg, 0.1 mmol) in acetonitrile (16 ml) containing trimethyl amine (1 g, 16.9 mmol) was stirred at room temperature until complete and then concentrated in vacuo. The residue was triturated with acetonitrile and then with ether. The supernate was concentrated in vacuo and then dissolved in methanol:dichloromethane (1:4, 3 ml) and precipitated with ether to yield the desired bis trimethylammonium salt (27 mg, 34% yield, mp dec. 166° C.) whose structure was confirmed by NMR and mass spectroscopy.

9.4 Preparation of 5-fluorouracil-1,3-bis-(2-trimethylaminoethoxycarbonyloxymethyl), diiodide salt To a 0° C. solution of 2-bromoethanol (2.25 g, 18 mmol) in dichloromethane (50 ml) was added pyridine (1.503 g, 19 mmol), followed by chloromethyl chloroformate (2.34 g, 18 mmol). The reaction mixture was stirred at 0° C. for one hour, diluted with dichloromethane (80 ml), washed with saturated aqueous sodium chloride, 10% aqueous citric acid, and saturated aqueous sodium chloride, dried over sodium sulfate, and concentrated in vacuo to yield the desired carbonate (3.42 g, 73.6% yield) which was used without further purification.

A solution of the carbonate prepared above (1.88 g, 8.66 mmol) and sodium iodide (4.05 g, 27 mmol) in acetone (60 ml) was heated at 60°–67° C. for one hour. Additional sodium iodide (2.0 g) was heated and the reaction was heated at 60°–67° C. for an additional hour. The reaction mixture was filtered, concentrated in vacuo, and dissolved in dichloromethane (100 ml). The dichloromethane solution was washed with 5% aqueous sodium thiosulfate and saturated aqueous sodium chloride, dried over sodium sulfate, and concentrated in vacuo to yield the desired diiodo carbonate (2.56 g, 83% yield) which was used without further purification. The structure of the carbonate was confirmed by NMR.

A solution of 5-fluorouracil (209 mg, 1.607 mmol), DIEA (517 mg, 4 mmol) in DMA (3 ml) was treated with the diiodo carbonate prepared above (1.07 g, 3 mmol). The reaction mixture was stirred at room temperature for 4 hours and concentrated in vacuo. The residue was dissolved in dichloromethane (90 ml), washed with saturated aqueous sodium chloride, 10% aqueous citric acid, 5% aqueous sodium thiosulfate, and saturated aqueous sodium chloride, dried over sodium sulfate, and concentrated in vacuo. Column chromatography (flash silica, eluting with ethyl acetate:dichloromethane 1:8) yielded the desired carbonate (714 mg, 76% yield, mp 115°–116° C.).

The carbonate prepared above (710 mg, 1.212 mmol) was treated with a solution of trimethylamine in acetonitrile (1.43M, 16 ml). The reaction mixture was stirred at room temperature for 4 hours and at 40° C. overnight and was then concentrated in vacuo. The residue was triturated with acetonitrile and ether. The precipitate was dried in vacuo to yield the desired trimethylammonium salt (860 mg, quantitative yield, mp 142° C., dec. 184°–192° C.). The structure of the salt was confirmed by NMR and mass spectroscopy.

9.5 Preparation of 6-mercaptopurine-S,9-bis-[6-(N,N,N-trmethylamino)hexanolyoxymethyl], diiodide salt and 6-mercaptopurine-S-[6-(N,N,N-trmethylamino)hexanoyloxymethyl], iodide salt To a solution of 6-bromohexanoic acid (2.94 g, 15 mmol) and tetrabutylammonium hydrogen sulfate (509 mg, 1.5 mmol) in dichloromethane (25 ml) was added an aqueous solution (30 ml) of potassium bicarbonate (6 g). To the reaction mixture was then added a solution chloromethanesulfonyl chloride (2.73 g, 16.5 mmol) in dichloromethane (9 ml). The reaction mixture was stirred at room temperature for one hour and the organic layer was separated. The aqueous layer was diluted with water (20 ml) and extracted with dichloromethane (2×30 ml). The organic layers were combined, dried over sodium sulfate, and concentrated in vacuo to yield crude chloromethyl ester (4.2 g) which was filtered through silica gel (eluting with 5% methanol in dichloromethane, 45 ml) to yield pure ester (3.27 g, 89.5% yield) whose structure was confirmed by NMR.

A solution of the chloromethyl ester prepared above (2.00 g, 8.5 mmol) and sodium iodide (3.75 g, 25 mmol) in acetone (80 ml) was heated to reflux for one hour. The reaction mixture was cooled and filtered. The filtrate was concentrated in vacuo and dissolved in dichloromethane (60 ml). This solution was washed with saturated aqueous sodium chloride and 5% aqueous sodium thiosulfate, dried over sodium sulfate, and concentrated in vacuo to yield the desired diiodo compound (2.99 g, 92% yield) which was used immediately without further purification.

To a solution of 6-mercaptopurine (340 mg, 2 mmol) and potassium carbonate (330 mg) in acetone (6 ml) was added a solution of the diiodo ester prepared above (764 mg, 2 mmol) in acetone (3 ml). The reaction mixture was sonicated for 2 to 3 minutes and then stirred vigorously for 3.5 hours at room temperature. The reaction mixture was filtered and the filtrate was rinsed with acetone. The acetone solutions were combined and concentrated in vacuo. The residue was extracted with chloroform (3×40 ml). The precipitate was dissolved in water, extracted with chloroform, and dried over sodium sulfate. The chloroform solutions were combined and concentrated in vacuo. Column chromatography (flash silica, eluting with ethyl acetate:dichloromethane 1:4) yielded the desired bis 6-iodohexanoic acid ester (148 mg, 11.2% yield) and the mono ester (237 mg, 29.2% yield).

The bis ester prepared above (148 mg, 0.224 mmol) was treated with a solution of trimethylamine in acetonitrile (1.15M, 6 ml) at room temperature for 22 hours. The reaction mixture was concentrated in vacuo. The residue was dissolved in dichloromethane:methanol (8:1) and precipitated out with ether. The precipitate was separated by centrifuge and dried in vacuo to yield the desired bis-trimethylammonium salt (185 mg, quantitative yield, mp foam at 86° C., clear at 150° C.).

Likewise, the monoester (240 mg, 0.58 mmol) was treated with a solution of trimethylamine in acetonitrile (1.15M, 7 ml) at room temperature. The reaction mixture was concentrated in vacuo. The residue was dissolved in acetonitrile and precipitated with ether to yield the desired mono-trimethylammonium salt (268 mg, 95% yield, mp foam at 89° C., clear at 150° C.).

EXAMPLE 10

Preparation of Quaternary Ammonium Salts 10.1 Preparation of 3-hydroxy-17β-estra-trienyl N,N,N-trimethylaminoethyl carbonate, iodide salt (3,17β-estradiol choline iodide carbonate)

Estradiol dimethylaminoethyl carbonate ester (500 mg, 1.29 mmol) was dissolved in tetrahydrofuran (10 ml) and iodomethane (200 mg) was added with stirring at room temperature. After 5 hours the precipitated product was separated by centrifugation and vacuum dried at 40° C. for 2 hours to give 390 mg (68% yield) of desired product whose structure was confirmed by NMR.

10.2 Preparation of 3-O-(indomethacinyl)-D,L-carnitine methyl ester

3-O-(indomethacinyl)-D,L-norcarnitine methyl ester (530 mg, 1.09 mmol) was dissolved in 5 ml ether and treated with iodomethane (330 mg, 2.33 mmol). Stirring overnight at room temperature led to formation of a precipitate which was separated by filtration, washed with ether and dried in vacuo to give the desired compound (490 mg, 70% yield, FAB mass spec. 515.4 (M+-I), NMR agrees with structure).

10.3 Preparation of indomethacinylcholine iodide

The N,N-dimethylaminoethyl ester of indomethacin (455 mg, 1.06 mmol) was dissolved in ether (5 ml) and iodomethane (300 mg, 2.11 mmol) was added. After stirring at room temperature for one hour a large amount of precipitate had formed so the reaction mixture was diluted with additional ether (20 ml) and stirring continued overnight. The solid was removed by filtration, washed with ether (50 ml), and dried in vacuo to give the desired product as a white solid (390 mg, 0.68 mmol, 57% yield, mp 207°–209° C.). Further concentration of the filtrate gave a second crop of 32 mg, mp 210° C. NMR confirmed the structure of the compound.

EXAMPLE 11

Preparation of Charged Complexes From Pharmaceutical Agents Having Tertiary Amino Groups To a solution of deprenyl (424 mg, 2.3 mmol) in acetonitrile (5 ml) was added chloromethyl ethyl carbonate (315 mg, 2.3 mmol), followed by sodium iodide (340 mg, 2.3 mmol). The reaction was stirred at 40° C. for 12 hours, filtered, and concentrated in vacuo to yield the crude quaternary ammonium salt (810 mg) which could be purified by trituration with 10% methanol in ethanol. The structure of the salt was verified by NMR and mass spectrometry.

In a similar fashion, replacing chloromethyl ethyl carbonate with chloromethyl octyl carbonate, there is produced the corresponding quaternary ammonium salt.

Likewise, replacing chloromethyl ethyl carbonate with chloromethyl acetate, results in the formation of the corresponding quaternary ammonium salt.

EXAMPLE 12

Preparation of Nucleotide-Based Chemical Modifiers

Collections of radioactively-labeled, single-stranded oligonucleotides and nucleic acids of random sizes can be generated using techniques well known in the art. For example, multiple rounds of DNA synthesis from a DNA template using Taq DNA polymerase, dideoxynucleotide triphosphates, and either $^{32}P$-labeled oligonucleotide primers or $^{32}P$, $^{33}$, or $^{35}S$-labeled deoxynucleosides can be performed. See *Promega Protocols and Applications Guide*, 2nd Ed., Promega Corp., Madison, Wis. (1991).

Shorter oligonucleotides (less than 15–20 residues in length) can be prepared on a commercially-available oligonucleotide synthesizer (e.g., Applied Biosystems Model 394 Oligonucleotide Synthesizer), using radioactive end-labeling with $^{32}P$ and T4 polynucleotide kinase.

In addition, any of a variety of other methodologies can be used, including Bal 31 nuclease digestion of DNA followed by radioactive labeling, "nick translation" or "random primer synthesis", which uses Dnase 1 or random oligonucleotide primers, respectively, to create primer-template junctions for the incorporation of radioactively-labeled deoxynucleosides by DNA polymerases, etc. The labeled DNA's should be in sufficient molar excess over their templates, as well as devoid of detectable secondary structures (unless engineered into the template sequence), to ensure that no higher order, macromolecular structures are formed.

The size distribution of a sample of a mixture of labeled fragments can be assessed by electrophoresis using a standard DNA sequencing gel and autoradiography. See, e.g., Sambrook et al. *Molecular Cloning*. Typically, a distribution of uniformly labeled fragments extending from approximately 5–200 nucleotides is created.

EXAMPLE 13

In Vitro Assay

General procedure for serum hydrolysis of pharmaceutical agent-modifier complexes Stock solutions (6 mM) of the pharmaceutical agent-modifier complexes were prepared in ethanol (by vortexing, sonication or warming at 37° C. if necessary). If required for solubility, a drop of dimethylsulfoxide, dimethylformamide or methanol may be added. (Acetonitrile cannot be used because it deactivates the serum enzymes.)

HPLC separation methods were established for each study by dilution of the above stock solution (6 µl) in acetonitrile (1 ml) to give a 36 µM solution. Samples (10 µl) were injected onto a Nucleosil 5C8 (250×4 mmID) and guard column (11×4 mm ID) and eluted with a mobile phase of approximately 65% HPLC grade water and 35% of a solution of 0.1% trifluoroacetic acid in acetonitrile, the exact proportions being adjusted in each case to give optimum separation and run times.

Freshly defrosted human serum (3 ml, Sigma) was warmed at 37° C. for five minutes and then 60 µl of the agent-modifier complex stock solution was added with vortexing. Incubation at 37° C. was continued and aliquots (400 µl) were removed at six appropriate time points based on $t_{1/2}$ estimated from a preliminary one-point study. The aliquots were added to 800 µl of 2% zinc sulfate solution in a 1.5 ml disposable microcentrifuge tube, vortexed immediately and centrifuged at 14,000 RPM for 3 minutes. The supernatants (10 µl) were then injected onto the HPLC and peak areas were used to determine the % remaining. Serum blanks were prepared similarly by addition of serum to the zinc sulfate solution followed by centrifugation, and time=0 samples were also prepared by adding serum to the zinc sulfate solution followed by addition of the complex and separation by centrifugation. The time=0 samples, as well as the original stock solutions, were also used to study the stability of the complex in the absence of enzyme. Half-lives were calculated using the equation $$y - \ln 50 = 3.912 = mx + b$$

by plotting time (x) vs. ln % remaining (y) to obtain the slope (m) and the y intercept (b). Results are given in Table 5.

TABLE 5

| Pharmaceutical Agent-Chemical Modifier Complex* | Serum Half-life |
|---|---|
| digitoxigenin-3-(O-acetyl-D,L-carnitine) ester, (D isomer), chloride salt | ~50 min |
| digitoxigenin-3-(O-acetyl-L-carnitine) ester, chloride salt | 5.4 hr |
| digitoxigenin-3-(O-palmityl-L-carnitine) ester, chloride salt | ~3 hr |
| digitoxigenin-3-(6-morpholino-hexanoate) | 248 hr |
| digitoxin-4′″-(6-morpholino-hexanoate), may be mixture with 3′″- or other isomers | 47 hr |
| 2-(4-nitrophenyl)ethanol 6-morpholino-hexanoate | 27.8 sec |
| 2-(4-nitrophenyl)ethanol 4-morpholinomethyl-benzoate | 45.7 sec |
| 2-(4-nitrophenyl)ethanol O-acetyl-L-carnitine ester, chloride salt | 210 or 455 min |
| 17β-estradiol-17β-(O-acetyl-L-carnitine) ester | 4 hr |
| digitoxigenin-3-(O-choline chloride carbonate) ester | 13.6 (12.2) min |
| 2-(4-nitrophenyl)ethanol 6-(O-acetyl-L-carnitinamido))-hexanoate ester, chloride salt | 7.9 sec |
| 1-(4-nitrophenyl)-2-propanol 6-(O-acetyl-L-carnitinamido))-hexanoate ester, chloride salt | 21.4 (30.2) min |
| 2-(4-nitrophenyl)ethanol 3-(N—O-acetyl-L-carnitinamido))-propanoate ester, chloride salt | 5.5 min |
| 2-(4-nitrophenyl)ethanol choline carbonate ester, chloride salt | <2 sec |
| 1-(4-nitrophenyl)-2-propanol 6-(O-acetyl-L-carnitinamido))-hexanol carbonate ester, chloride salt | 3.5 min |
| 4-(4-nitrophenyl)cyclohexanol choline carbonate ester, iodide salt | 19.6 sec |
| digitoxin-4′″-(choline chloride) carbonate ester | 5.3 min |
| digoxin-4′″-[6-(O-palmitoylcarnitinamido-hexyl carbonate, chloride salt | 21 min |
| O-(indomethacinyl)-(D,L)-norcarnitine, methyl ester | 257 min |
| (indomethacinyl)choline iodide | <1 min |
| indomethacin ethyl ester | >>4 day |
| indomethacin (N,N-diethylglycolamide) ester | 22.8 min |
| O-indomethacinyl-(D,L-carnitine methyl ester), iodide salt | 11 hr |
| O-indomethacinyl-(L-carnitine hydrochloride) | >>30 min |
| progesterone 3-{2-O-[6-O—(O-acetylcarnitinyl)-decanoyl]-glycolic acid} enol ester | 28.9 min |
| 3,17β-estradiol-17β-choline carbonate, iodide salt | 16 min |
| indomethacin 2-(N-(1-butyl)-N,N-dimethylamino-ethylester, bromide salt | 38 sec |
| indomethacin 2-(N-(2-hydroxyethyl)-N,N-dimethyl)aminoethyl ester, bromide salt | 58.6 sec |
| digitoxin-4′″-6-[O-(acetylcarnitinamido)hexyl] carbonate ester | 34.8 min |
| 2-(4-nitrophenyl)ethylamine choline carbamate, chloride salt | 86 hr |
| indomethacin 2-[N-(6'-N',N'-dimethylamino)-hexanamido]ethyl ester | 13.6 hr |
| indomethacin 2-[N-methyl-N-(6'-N',N'-dimethylamino)hexanamido]ethyl ester | 13.5 min |
| indomethacin 2-[N-(6'-N',N',N'-trimethylamino)-hexanamido]ethyl ester, iodide salt | 22.6 hr |
| indomethacin 2-[N-methyl-N-(6'-N',N',N'-trimethylamino)hexanamido]ethyl ester, iodide salt | 3.4 hr |
| 2-(4-nitrophenyl)ethylamine 3-(O-acetyl)-L-carnitine amide, chloride salt | 26.1 hr |
| 3,17β-estradiol-17β-betaine ester, chloride salt | 4.5 hr |
| 3-hydroxy-estra-1,3,5(10)-trien-17β-yl-2-(N,N,N-trimethylamino)ethoxycarbonylmethyl carbamate, iodide salt | 97 sec |
| 3,17β-estradiol-3-choline carbonate, iodide salt | 92 sec |
| 17β-estradiol-3-(O-acetyl-L-carnitine) ester | 8 min |
| 17β-estradiol-17β-(O-acetyl-L-carnitine) ester | 4 hr |
| digoxin-4′″-(choline chloride) carbonate ester | 79 sec |
| digoxin-4′″-(O-acetylcarnitinate) chloride salt | 5 min |
| digoxin-4′″-(4-trimethylamino)butyrate bromide | 7 hr |
| digoxin-4′″-4-(dimethylamino)butyrate | 1.4 hr |
| digoxin-4′″-(O-palmitoylcarnitinate) chloride salt | 19 min |
| indomethacin hydroxymethyl ketone choline iodide carbonate | 65 sec |
| indomethacin 6-(O-acetyl-L-carnitinamido)-hexanoyloxymethyl ester, chloride salt | 30 min |
| O-indomethacinyl-(D,L-norcarnitine methyl ester | 4.3 hr |
| indomethacin hydroxymethyl ketone | 15 hr |
| indomethacin methyl ester | 144 hr |
| theophylline-7-(N,N-dimethylglycyloxymethyl | 28 hr |
| methotrexate-bis-choline ester, dibromide salt | 14 hr |
| theophylline-7-(N,N-trimethylglycyloxy-methyl), iodide salt | 30 sec |
| theophylline-7-[4-(N,N,N-trimethylamino)-butyroyloxymethyl], bromide salt | 2.4 hr |
| nalidixic acid, choline ester, bromide salt | 66 min |
| nalidixic acid 6-(N,N,N-trimethylamino)-hexanoyloxymethyl ester, iodide salt | 4.8 min |
| formestane-4-choline carbonate, bromide salt | 26 min |
| melatonin-1-choline carbamate, bromide salt | 15 hr |
| digoxin-4′″-[(O-acetyl)-betonicine ester], chloride salt | 1.8 min |
| betonicine-O-acetate 4-nitrophenethyl ester | 6 min |
| digoxin-3',3″,12-tris-(6-trimethylaminohexanoyl-oxymethyl carbonate)-3′″,4′″-cyclic carbonate, tribromide salt | 14 hr |
| digoxin-3',3″-bis-(choline carbonate)-3′″,4′″-cyclic carbonate, dibromide salt | 34 hr |
| digoxin-3′″-(choline carbonate)-3′″,4′″-cyclic carbonate, dibromide salt | 22 hr |
| digoxin-12-[5-(4-trimethylaminobutyroyloxy)-hexanoate]-3′″,4′″-cyclic carbonate | 21 days |
| digoxin-3',3″-bis-(6-trimethylaminohexanoyloxy-methyl carbonate)-3′″,4′″-cyclic carbonate, bromide salt | 10 hr |
| digoxin-3'-(choline carbonate)-3′″,4′″-cyclic carbonate, dibromide salt | 22 hr |
| digoxin-4′″-stachydrine ester, chloride salt | 5.1 min |
| digoxin-12-[4-(N,N-dimethylamino)butyrate]-3′″,4′″-cyclic carbonate, hydrochloride salt | 24 hr |
| digoxin-12-[6-(N,N,N-trimethylamino)hexanoate]-3′″-4′″-cyclic carbonate, bromide salt | 14 days |
| digoxin-12-[6-(N,N-dimethylamino)hexanoate]-3′″,4′″-cyclic carbonate | 3.6 wk |
| digoxin-12-[1-(6-betainoyloxyhexyl)] carbonate-3′″,4′″-cyclic carbonate, chloride salt | 2.8 wk |
| digoxin-12-(6-trimethylaminohexanoyloxymethyl carbonate)-3′″,4′″-cyclic carbonate, bromide salt | 2.8 hr |
| digoxin-4′″-[4-(4-trimethylaminobutyroyloxy)-butyrate]bromide | 7 hr |
| digoxin-12-(choline carbonate)-3′″,4′″-cyclic carbonate, bromide salt | 29 hr |
| digoxin-12-(4-trimethylaminobutyrate)-3′″,4′″- | 4 days |

TABLE 5-continued

| Pharmaceutical Agent-Chemical Modifier Complex* | Serum Half-life |
|---|---|
| cyclic carbonate, bromide salt | |
| digoxin-4'''-[5-(4-trimethylaminobutyroyloxy)-hexanoate] bromide salt | 14 hr |
| digoxin-4'''-[1-(6-betainoyloxyhexyl)]carbonate, chloride salt | 21 min |
| digoxin-12-[N-(5-carboxypentyl)-N,N-dimethyl-aminomethyl] carbonate-3''',4'''-cyclic carbonate, bromide salt | 48 min |
| nalidixic acid, cholinecarbonato methyl ester, iodide salt | 76 sec |
| digoxin-12-(N,N,N-trimethylaminomethyl)-carbonate 3''',4'''-cyclic carbonate, chloride salt | 42 min |
| digoxin-4'''(3''')-(6-trimethylaminohexanoyloxy-methyl ether iodide salt (1:1 mixture) | 10 hr |
| digoxin-12-(N-[6-(N',N',N'-trimethylamino)-hexanoyloxymethyl]glycinoyloxymethyl)carbonate-3''',4'''-cyclic carbonate, bromide salt | 7 min |
| digoxin-12-stachydrine ester, 3''',4'''-cyclic carbonate, chloride salt | 4.9 hr |
| lorazepam-3-(O-acetylcarnitine) ester, chloride salt | 5.2 hr |
| lorazepam-3-choline carbonate, chloride salt | 2.2 hr |
| threonine, L-isomer, HO-(O-acetyl-L-carnitine ester), N-CBZ, benzyl ester | 40 min |
| serine, L-isomer, HO-trigonellate ester, N-CBZ, benzyl ester | 5 min |
| threonine, L-isomer, HO-trigonellate ester, N-CBZ benzyl ester | 40 min |
| serine, L-isomer, HO-(O-acetyl-L-carnitine ester) N-CBZ, benzyl ester | 21 min |
| testosterone-17-choline carbonate, bromide salt | 29 min |
| testosterone-17-betainoyloxymethyl carbonate, iodide salt | 38 sec |
| digoxin-12-nicotinate ester, 3''',4'''-cyclic carbonate | 13.8 days |
| digoxin-3''',4'''-cyclic carbonate | 9 sec |
| p-nitrophenylethyl alcohol nicotinate ester | 26 sec |
| p-nitrophenylethyl alcohol trigonelline ester | 28 min |
| testosterone-17-betainoyloxymethylcarbonyloxy-methyl carbonate, iodide salt | 8.5 min |
| testosterone-17-(L-carnitine ethyl ester) carbonate, iodide salt | 49 min |
| testosterone-17-(6-trimethylammoniohexanoyl-oxymethyl) carbonate, bromide salt | 19 min |
| testosterone-17-(O-palmityl-L-carnitinate), chloride salt | 4.9 days |
| testosterone-17-(O-acetyl-L-carnitinate), chloride salt | 4 days |
| 5-fluorouracil-1-(4-trimethylammoniobutyroyl-oxymethyl)-3-(butyroyloxymethyl), iodide salt | 3.4 hr |
| 5-fluorouracil-1-(4-trimethylammoniobutyroyl-1-oxyethyl)-3-(butyroyloxymethyl), iodide salt | 9.7 min |
| 5-fluorouracil-1-(lauroyloxmethyl) | 3.23 min |
| 5-fluorouracil-1-(lauroyloxymethyl)-3-(4-tri-methylammoniobutyroxyoxymethyl), iodide salt | 7 hr |
| 5-fluorouracil-1-(lauroyloxymethyl)-3-(choline-carbonyloxymethyl), iodide salt | 27 min |
| 5-fluorouracil-1-(N-(4-trimethylammonio-butyroyloxymethyl)-3-(N-lauroxyoxymethyl), iodide salt | 3.2 hr |
| 5-fluorouracil-1-(N-(4-trimethylammonio-butyroyloxy-1-ethyl)-3-(N-lauroyloxymethyl), iodide salt | 13 min |
| cisapride choline carbamate, chloride salt | 2.5 hr |
| cisapride-(N-(1-methylpyridinium-3-carboxamide), chloride salt | 1 hr |
| cisapride-N-(6-trimethylammoniohexanoyl-oxymethylammonio), diiodide salt | 1 hr |
| cisapride-N-acetoxymethylammonio, iodide salt | 6.5 min |
| cisapride-N-butyroyloxymethylammonio, iodide salt | 7.6 min |
| cisapride-N-ethyoxycarbonyloxymethylammonio, iodide salt | 4.4 min |
| cisapride-N-lauroyloxymethylammonio, iodide salt | 5.4 min |

TABLE 5-continued

| Pharmaceutical Agent-Chemical Modifier Complex* | Serum Half-life |
|---|---|
| deprenyl-N-acetoxymethyl, bromide salt | 4.2 min |
| deprenyl-N-benzoyloxymethyl, iodide salt | 5 min |
| deprenyl-N-butyroyloxy-1-ethyl, bromide salt | 28 min |
| deprenyl-N-butyroyloxymethyl, iodide salt | 17 sec |
| deprenyl-N-ethoxycarbonyloxymethyl, iodide salt | 71 sec |
| deprenyl-N-octyloxycarbonyloxymethyl, iodide salt | 26 sec |
| deprenyl-N-pivaloyloxymethyl, iodide salt | 20 min |
| methotrexate-bis-(4-trimethylammoniobutyroyl-oxymethyl ester), diiodide salt | 1.8 hr |
| morphine-6-O-(trimethylammoniobutyrate chloride, hydrochloride salt | 26 hr |
| progesterone-3-(4-N,N,N-trimethylammonio-butyrate enol ester, bromide salt | 3 hr |
| progesterone-3-betainoyl enol ester, bromide salt | 1.6 min |

*As noted above, several compounds in Table 5 are model compounds, useful in assessing the optimal spacer for a desired improvement of a specific pharmaceutical agent.

EXAMPLE 14

In Vivo Assay

Synthetic membrane, hairless guinea pig, hairless mouse, or human (either living or cadaverous) skin can be prepared by techniques known in the art. The skin or membrane is inserted into a standard electrotransport cell between two chambers. The compound to be tested is placed in an appropriate buffer in a "donor" chamber on the exterior side of the skin or membrane, along with a negative electrode. A "counter" chamber containing suitable buffer and the positive electrode is placed on the interior side of the skin or membrane.

Following application of electric current, a sample is withdrawn from the counter chamber and analyzed. The transdermal delivery of a labeled-test compound can be assessed by electrophoresis analysis of the sample using standard DNA sequencing followed by autoradiography. Transport can also be assessed using an antibody-mediated reaction, an activity assay, or by radioactively prelabeling the test compound, either enzymatically or metabolically, and monitoring the radioactivity.

EXAMPLE 15

Alternate In Vivo Assay

The in vivo iontophoretic delivery of pharmaceutical agent from the pharmaceutical agent-chemical modifier complexes may be accomplished with a battery-powered control module and two hydrogel-electrode patches. The power source is a one-channel constant-current device compliant to within 5% of the set point value and can contain a current of up to 2 mA into a resistive load of 10 kiloohms.

The hydrogel-electrode patches consist of a conductive polyvinyl acetate (PVA) hydrogel matrix that is in contact with a metallic electrode mesh and is housed in a circular section of polyethylene foam tape. The hydrogel contact area with the skin is 25 cm$^2$. The "active" patch has a silver electrode and a hydrogel composed of 26% pharmaceutical agent-chemical modifier complex, 15% PVA and 59% water by weight. The other patch has a silver chloride electrode and a hydrogel composed of 2% sodium chloride, 15% PVA and 83% water by weight. The hydrogel formulations are prepared by dissolving PVA in water at 90° C., adding the appropriate substrate, pouring the solution in electrode housings, and freezing at −20° C. for a minimum of 4 hr.

Using electric clippers, hair is removed from the dorsal surface of weaning pigs weighing between 6 and 12 kg. The clipped regions are cleaned with wet gauze and dried. The hydrogel patches are then pressed into place. The appropriate lead wires from the control module are connected to the two patches and the control module is taped securely to the back of the pig.

Iontophoretic delivery of the pharmaceutical agent-chemical modifier complex is performed at currents of up to 1 mA for a duration of 24 hr. After initiating iontophoresis, blood samples are collected every 2 hr by means of an indwelling jugular catheter. Each pig is utilized on consecutive days for two iontophoretic studies at two different currents. New skin sites and new patches are used for each experiment.

Blood samples are heparinized and centrifuged, and the plasma is stored at −80° C. Plasma concentrations of the pharmaceutical agent, chemical modifier, spacer group, and pharmaceutical agent-chemical modifier complex are determined using an HPLC method. The area under the plasma concentration versus time curve is used to estimate the value of the systemic clearance for each pig.

The disclosures of all articles and references, including patents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. An iontophoretic drug delivery system for administering a pharmaceutical agent to a patient comprising:

(a) a pharmaceutical agent-chemical modifier complex comprising:

a pharmaceutical agent, suitable for transdermal transport at therapeutically effective doses of less than 50 milligrams per day, having a derivatizable chemical functionality; and a charged, naturally-occurring chemical modifier, conjugated to the agent's derivatizable chemical functionality by a covalent, physiologically cleavable bond, wherein said chemical modifier is selected from the group consisting of taurine, betaine, L carnitine, choline, norcholine, lysine, N-methylated amino acids, trigonelline, stachydrine, betonicine, cytochrome c, squalamine, chonemorphine, and conessine;

where said pharmaceutical agent-chemical modifier complex has a charge-to-mass ratio of at least one charge per 1000 daltons, and wherein upon iontophoretic delivery of said composition and cleavage of said covalent bond, said chemical modifier is present at a non-toxic level and said pharmaceutical agent is delivered to said subject at said therapeutically effective dose; and (b) a means for iontophoretically delivering said composition at a selected skin site whereby said chemical modifier is cleaved from the complex by a physiological process and said pharmaceutical agent is released within the patient.

2. The device of claim 1 wherein the complex is selected from the group consisting of O-(indomethacinyl)norcholine; (indomethacinyl)choline iodide; 3,17β-estradiol-3-choline carbonate, iodide salt; piroxicam-N,O-bis(choline chloride) carbonate ester; digitoxin-4'''-(choline chloride) carbonate ester; 3,17β-estradiol-17β-betaine ester, chloride salt; and indomethacin hydroxymethyl ketone choline iodide carbonate.

3. The device of claim 1 wherein the transdermal delivery of the complex is enhanced over the transdermal delivery of the agent alone.

4. The device of claim 1 wherein one or more chemical modifiers are covalently bonded to the pharmaceutical agent.

5. The device of claim 1 wherein the pharmaceutical is selected from the group consisting of digitalis drugs, steroidal compounds, non-steroidal anti-inflammatories, protein and peptide drugs, and nitrogen heterocycles.

* * * * *